United States Patent
Cals et al.

(10) Patent No.: US 9,738,600 B2
(45) Date of Patent: Aug. 22, 2017

(54) ROR GAMMA (RORγ) MODULATORS

(71) Applicant: LEAD PHARMA CEL MODELS IP B.V., Oss (NL)

(72) Inventors: Joseph Maria Gerardus Barbara Cals, Oss (NL); Sander Bernardus Nabuurs, Oss (NL)

(73) Assignee: LEAD PHARMA CEL MODELS IP B.V., Oss (NL)

( * ) Notice: Subject to any disclaimer, the term of this patent is extended or adjusted under 35 U.S.C. 154(b) by 0 days.

(21) Appl. No.: 15/102,098

(22) PCT Filed: Dec. 3, 2014

(86) PCT No.: PCT/EP2014/076390
§ 371 (c)(1),
(2) Date: Jun. 6, 2016

(87) PCT Pub. No.: WO2015/082533
PCT Pub. Date: Jun. 11, 2015

(65) Prior Publication Data
US 2016/0304448 A1    Oct. 20, 2016

(30) Foreign Application Priority Data

Dec. 5, 2013 (EP) .................................... 13195813
Sep. 2, 2014 (EP) .................................... 14183274

(51) Int. Cl.
| | |
|---|---|
| *C07C 317/44* | (2006.01) |
| *A61K 31/167* | (2006.01) |
| *C07D 213/75* | (2006.01) |
| *A61K 31/18* | (2006.01) |
| *A61K 31/44* | (2006.01) |
| *C07C 311/16* | (2006.01) |
| *C07C 311/20* | (2006.01) |
| *C07C 317/46* | (2006.01) |
| *A61K 45/06* | (2006.01) |

(52) U.S. Cl.
CPC .......... *C07C 317/44* (2013.01); *A61K 31/167* (2013.01); *A61K 31/18* (2013.01);
(Continued)

(58) Field of Classification Search
None
See application file for complete search history.

(56) References Cited

FOREIGN PATENT DOCUMENTS

| WO | 2011/115892 A1 | 9/2011 |
| WO | 2013/029338 A1 | 3/2013 |
| WO | 2013/171729 A2 | 11/2013 |

OTHER PUBLICATIONS

Aggarwal et al. "Interleukin-23 Promotes a Distinct CD4 T Cell Activation State Characterized by the Production of Interleukin-17", The Journal of Biological Chemistry, vol. 278, No. 3, pp. 1910-1914, 2003.

Bahrami et al. "Direct Conversion of Thiols to Sulfonyl Chlorides and Sulfonamides", Journal of Organic Chemistry, vol. 74, No. 24, pp. 9287-9291, 2009.

Cua et al. "Interlukin-23 Rather Than Interlukin-12 is the Critical Cytokine for Autoimmune Inflammation of the Brain", Letter to Nature, vol. 421, pp. 744-748, 2003.

(Continued)

*Primary Examiner* — Bong-Sook Baek
(74) *Attorney, Agent, or Firm* — Oliff PLC

(57) ABSTRACT

$A_{11-14}$ are N or $CR_{11-14}$, respectively, maximum two of the four positions $A_{11-14}$ simultaneously N; $R_1$ is C(1-6)alkyl, C(3-6)cycloalkyl, C(3-6)cycloalkylC(1-3)alkyl, (di)C(1-6)alkylamino, (di)C(3-6)cycloalkylamino or (di)(C(3-6)cycloalkylC(1-3)alkyl)amino, all alkyl and cycloalkyl group carbon atoms optionally substituted with F and F or methyl, respectively; $R_2$ and $R_3$ independently H, F, methyl, ethyl, hydroxy, methoxy or $R_2$ and $R_3$ together is carbonyl, all present alkyl groups optionally substituted with F; $R_4$ is H or C(1-6)alkyl; $R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, C(3-6)cycloalkylC(1-3)alkyl, C(2-5)heterocycloalkyl or C(2-5)heterocycloalkylC(1-3)alkyl, all groups optionally substituted with F, Cl, C(1-2)alkyl, C(1-2)alkoxy or cyano; the sulfonyl group with $R_1$ represented by one of $R_{7-9}$; the remaining $R_{6-14}$ are independently H, halogen, C(1-3)alkoxy, (di)C(1-3)alkylamino or C(1-6)alkyl, all alkyl groups optionally substituted with F; and $R_{15-16}$ are independently H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkylC(1-3)alkyl, all groups optionally substituted with F, Cl, C(1-2)alkyl, C(1-2)alkoxy or cyano.

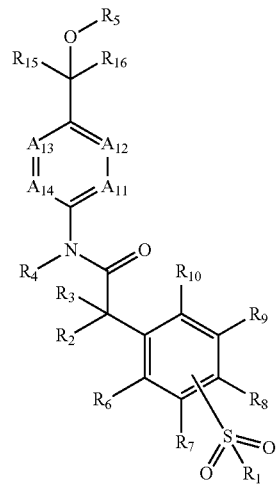

26 Claims, No Drawings

(52) U.S. Cl.
CPC ............... *A61K 31/44* (2013.01); *A61K 45/06* (2013.01); *C07C 311/16* (2013.01); *C07C 311/20* (2013.01); *C07C 317/46* (2013.01); *C07D 213/75* (2013.01); *C07C 2101/02* (2013.01); *C07C 2101/04* (2013.01); *C07C 2101/08* (2013.01); *C07C 2101/14* (2013.01)

(56) References Cited

OTHER PUBLICATIONS

Harrington et al. "Interlukin 17-producing CD4+ Effector T Cells Develop Via a Lineage Distinct From the T Helper Type 1 and 2 Lineages", Nature Immunology, vol. 6, No. 11, pp. 1123-1132, 2005.

Ivanov et al. "The Orphan Nuclear Receptor RORgammat Directs the Differentiation Program of Proinflammatory IL-17+ T Helper Cells", vol. 126, Cell, pp. 1121-1133, 2006.

Littman et al. "Th17 and Regulatory Cells in Mediating and Restraining Inflammation", Cell, vol. 140, pp. 845-858, 2010.

Park et al. A Distinct Lineage of CD4 T Cells Regulates Tissue Inflammation by Producing Interlukin 17, Nature Immunology, vol. 6, No. 11, pp. 1133-1141, 2005.

Singh et al. "Cesium Flouride Catalyzed Triflouoromethylation of Esters, Aldehydes, and Ketones with (Triflouoromethyl)trimethylsilane", Journal of Organic Chemistry, vol. 64, pp. 2873-2876, 1999.

Solt et al. "Suppresion of TH17 Differentiation and Autoimmunity by a Synthetic ROR Ligand", Nature, vol. 472, pp. 491-494, 2011.

Weaver et al. "IL-17 Family Cytokines and the Expanding Diversity of Effector T Cells Lineages", Annual Reviews Immunology, vol. 25, pp. 821-852, 2007.

Feb. 2, 2015 International Search Report issued in International Patent Application No. PCT/EP2014/076390.

Feb. 2, 2015 Written Opinion Issued in International Patent Application No. PCT/EP2014/076390.

ROR GAMMA (RORγ) MODULATORS

The present invention relates to modulators of RORγ, to pharmaceutical compositions comprising the same and to the use of said compounds for the treatment of RORγ-mediated diseases or conditions, in particular autoimmune diseases and inflammatory diseases.

T helper ($T_H$) cells play a crucial role in the adaptive immune system as they coordinate defense against specific pathogens. The interleukin 17 (IL-17) producing lineages of $T_H$ cells, amongst which $T_H17$ cells, have been directly implicated in the pathology of a multitude of autoimmune and inflammatory diseases, including, but not limited to, psoriasis, multiple sclerosis, rheumatoid arthritis, Crohn's disease, asthma, chronic obstructive pulmonary disease, and irritable bowel disease (Harrington et al, Nature Immunology 6, 1123-1132, 2005; Park et al, Nature Immunology 6, 1133-1141, 2005; Weaver et al, Annual Reviews Immunology 25, 821-852, 2007; Littman et al, Cell 140, 845-858, 2010).

Interleukin 17 and interleukin 23 (IL-23) are two pivotal cytokines in $T_H17$ biology. IL-17 is secreted by $T_H17$ cells and is a potent inducer of tissue inflammation; IL-23 has been shown to be a key participant in amplifying and stabilizing the proliferation of the $T_H17$ cell type via the IL-23 receptor (IL-23R) (Cua et al, Nature 421, 744-748, 2003; Aggarwal et al, J Biol Chem 278, 1910-1914, 2003). These findings highlight the therapeutic potential of targeting the IL-17/IL-23 axis.

The retinoic-acid-receptor-related orphan receptor γt (RORγt) acts as a master regulator of the development of $T_H17$ cells (Ivanov et al, Cell 126, 1121-1133, 2006), but also as a critical component in non-$T_H17$ IL-17 producing cells, such as for example γδ T-cells. The ROR gene family is part of the nuclear hormone receptor superfamily, and consists of three members (RORα, RORβ, and RORγ). Each gene is expressed in different isoforms, differing foremost in their N-terminal sequence (Jetten, Nuclear Receptor Signaling 7, e003, 2009). Two isoforms of RORγ have been identified: RORγ1 and RORγ2 (also known as RORγt). The term RORγ is used here to describe both RORγ1 and/or RORγ2.

Deficiency in, or inhibition of, RORγt results in, for example, decreased levels of IL-17 and IL-23R gene expression and amelioration of disease score in an experimental autoimmune encephalomyelitis (EAE) mouse model, highlighting the critical role of RORγt in IL-17/IL-23 mediated pathogenic responses (Ivanov et al, Cell 126, 1121-1133, 2006; Solt et al, Nature 472, 491-494, 2011).

Given the important role of RORγ in immune and inflammatory disorders it is desirable to prepare modulators of RORγ (as for example described in WO2011115892A1, WO2013029338A1 and WO2013171729A2), which can be used in the treatment of RORγ mediated diseases.

The present invention provides such novel RORγ modulator compounds.

The present invention relates to novel compounds according to Formula I

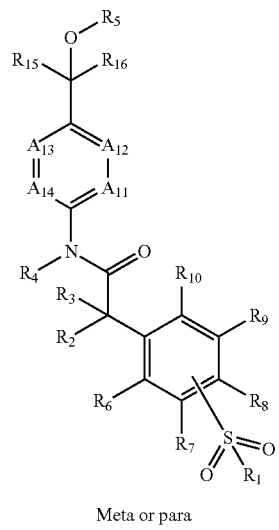

(Formula I)

Meta or para or a pharmaceutically acceptable salt thereof wherein $A_{11}$-$A_{14}$ are N or $CR_{11}$, $CR_{12}$, $CR_{13}$, $CR_{14}$, respectively, with the proviso that no more than two of the four positions A can be simultaneously N;

$R_1$ is C(1-6)alkyl, C(3-6)cycloalkyl, C(3-6)cycloalkylC(1-3)alkyl, (di)C(1-6)alkylamino, (di)C(3-6)cycloalkylamino or (di)(C(3-6)cycloalkylC(1-3)alkyl)amino, with all carbon atoms of alkyl groups optionally substituted with one or more F and all carbon atoms of cycloalkyl groups optionally substituted with one or more F or methyl;

$R_2$ and $R_3$ are independently H, F, methyl, ethyl, hydroxy, methoxy or $R_2$ and $R_3$ together is carbonyl, all alkyl groups, if present, optionally being substituted with one or more F;

$R_4$ is H or C(1-6)alkyl;

$R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, C(3-6)cycloalkylC(1-3)alkyl, C(2-5)heterocycloalkyl or C(2-5)heterocycloalkyl-C(1-3)alkyl, all groups optionally substituted with one or more F, Cl, C(1-2)alkyl, C(1-2)alkoxy or cyano;

the sulfonyl group with $R_1$ is represented by one of $R_7$, $R_8$ or $R_9$;

the remaining $R_6$-$R_{14}$ are independently H, halogen, C(1-3)alkoxy, (di)C(1-3)alkylamino or C(1-6)alkyl, all of the alkyl groups optionally being substituted with one or more F;

and $R_{15}$ and $R_{16}$ are independently H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkyl-C(1-3)alkyl, all groups optionally substituted with one or more F, Cl, C(1-2)alkyl, C(1-2)alkoxy or cyano.

The term C(1-6)alkyl as used herein means a branched or unbranched alkyl group having 1-6 carbon atoms, for example methyl, ethyl, propyl, isopropyl, butyl, tert-butyl, n-pentyl and n-hexyl. All carbon atoms may optionally be substituted with one or more halogen.

The term C(1-4)alkyl as used herein means an alkyl group having 1-4 carbon atoms, i.e. methyl, ethyl, propyl, isopropyl, butyl, isobutyl, sec-butyl, or tert-butyl. All carbon atoms may optionally be substituted with one or more halogen.

The term C(1-3)alkyl as used herein means an alkyl group having 1-3 carbon atoms, i.e. methyl, ethyl, propyl or isopropyl. All carbon atoms may optionally be substituted with one or more halogen.

The term C(1-2)alkyl as used herein means an alkyl group having 1-2 carbon atoms i.e. methyl or ethyl. All carbon atoms may optionally be substituted with one or more halogen.

The term C(6-10)aryl as used herein means an aromatic hydrocarbon group having 6-10 carbon atoms, for example phenyl or naphthyl. The preferred aromatic hydrocarbon group is phenyl. All carbon atoms may optionally be substituted with one or more halogen.

The term C(6-10)arylC(1-3)alkyl as used herein means an C(6-10)aryl group attached to a C(1-3)alkyl group, both with the same meaning as previously defined.

The term C(6)aryl as used herein means an aromatic hydrocarbon group having 6 carbon atoms, i.e. phenyl. All carbon atoms may optionally be substituted with one or more halogen.

The term C(6)arylC(1-3)alkyl as used herein means an C(6)aryl group attached to a C(1-3)alkyl group, both with the same meaning as previously defined.

The term heteroatom as used herein refers to a nitrogen, sulphur or oxygen atom.

The term C(1-9)heteroaryl as used herein means an aromatic group having 1-9 carbon atoms and 1-4 heteroatoms, which may be attached via a nitrogen atom if feasible, or a carbon atom. Examples include imidazolyl, thiadiazolyl, pyridinyl, pyrimidinyl, furyl, pyrazolyl, isoxazolyl, tetrazolyl and quinolyl. All carbon atoms may optionally be substituted with one or more halogen or methyl.

The term C(1-9)heteroarylC(1-3)alkyl as used herein means an C(1-9)heteroaryl group attached to a C(1-3)alkyl group, both with the same meaning as previously defined.

The term C(3-6)cycloalkyl as used herein means a saturated cyclic hydrocarbon having 3-6 carbon atoms, i.e. cyclopropyl, cyclobutyl, cyclopentyl or cyclohexyl. All carbon atoms may optionally be substituted with one or more halogen or methyl.

The term C(3-5)cycloalkyl as used herein means a saturated cyclic hydrocarbon having 3-5 carbon atoms, i.e. cyclopropyl, cyclobutyl or cyclopentyl. All carbon atoms may optionally be substituted with one or more halogen or methyl.

The term C(3-4)cycloalkyl as used herein means a saturated cyclic hydrocarbon having 3-4 carbon atoms, i.e. cyclopropyl or cyclobutyl. All carbon atoms may optionally be substituted with one or more halogen or methyl.

The term C(3-6)cycloalkylC(1-3)alkyl as used herein means an C(3-6)cycloalkyl group attached to an C(1-3)alkyl group, both with the same meaning as previously defined. An example is cyclopropylmethyl.

The term C(3-5)cycloalkylC(1-3)alkyl as used herein means an C(3-5)cycloalkyl group attached to an C(1-3)alkyl group, both with the same meaning as previously defined.

The term cyclopropylmethyl as used herein means a methyl group substituted with cyclopropyl. All carbon atoms are optionally substituted with one or more halogen or methyl.

The term C(2-5)heterocycloalkyl as used herein means a saturated cyclic hydrocarbon having 2-5 carbon atoms and 1-3 heteroatoms, which may be attached via a nitrogen atom if feasible, or a carbon atom. Examples include piperazinyl, pyrazolidilyl, piperidinyl, morpholinyl and pyrrolidinyl. All carbon atoms may optionally be substituted with one or more halogen or methyl.

The term C(2-5)heterocycloalkylC(1-3)alkyl as used herein means an C(2-5)heterocycloalkyl group attached to an C(1-3)alkyl group, both with the same meaning as previously defined.

The term (di)C(1-6)alkylamino as used herein means an amino group, which is monosubstituted or disubstituted independently with H or C(1-6)alkyl group(s), having the same meaning as previously defined.

It is to be understood that in the (di)C(1-6)alkylamino groups containing two C(1-6)alkyl groups, one of the C(1-6)alkyl groups can be replaced by a C(3-6)cycloalkyl group as previously defined.

The term (di)C(1-2)alkylamino as used herein means an amino group, which is monosubstituted or disubstituted independently with H or C(1-2)alkyl group(s), having the same meaning as previously defined.

The term (di)C(3-6)cycloalkylamino as used herein means an amino group, which is monosubstituted or disubstituted independently with H or C(3-6)cycloalkyl group(s), having the same meaning as previously defined. An example is cyclopropylamino.

It is to be understood that in the (di)C(3-6)cycloalkylamino groups containing two C(3-6)cycloalkyl groups, one of the C(3-6)cycloalkyl groups can be replaced by a C(1-6)alkyl group as previously defined.

The term (di)C(3-4)cycloalkylamino as used herein means an amino group, which is monosubstituted or disubstituted independently with H or C(3-4)cycloalkyl group(s), having the same meaning as previously defined.

It is to be understood that in the (di)C(3-4)cycloalkylamino groups containing two C(3-4)cycloalkyl groups, one of the C(3-4)cycloalkyl groups can be replaced by a C(1-6)alkyl group as previously defined.

The term cyclopropylamino means an amino group substituted with cyclopropyl. All carbon atoms may optionally be substituted with one or more halogen or methyl.

The term (di)(C(3-6)cycloalkylC(1-3)alkyl)amino as used herein means an amino group, which is monosubstituted or disubstituted independently with H or C(3-6)cycloalkylC(1-3)alkyl group(s) as previously defined.

It is to be understood that in the (di)(C(3-6)cycloalkylC(1-3)alkyl)amino groups containing two C(3-6)cycloalkylC(1-3)alkyl groups, one of the C(3-6)cycloalkylC(1-3)alkyl groups can be replaced by a C(1-6)alkyl or a C(3-6)cycloalkyl group, both as previously defined.

The term (di)C(1-3)alkylamino as used herein means an amino group, which is monosubstituted or disubstituted independently with H or C(1-3)alkyl group(s), having the same meaning as previously defined.

The term C(1-3)alkoxy means an alkoxy group having 1-3 carbon atoms, the alkyl moiety being branched or unbranched. All carbon atoms are optionally substituted with one or more F.

The term C(1-2)alkoxy means an alkoxy group having 1-2 carbon atoms. Preferred is methoxy. All carbon atoms may optionally be substituted with one or more F.

The term halogen as used herein means Cl or F.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt represents those salts which are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one embodiment the invention also relates to a compound according to Formula I wherein R1 is C(1-4)alkyl, C(3-5)cycloalkyl, C(3-5)cycloalkylC(1-3)alkyl, (di)C(1-2)alkylamino or (di)C(3-4)cycloalkylamino.

In another embodiment the invention relates to a compound according to Formula I wherein R1 is C(1-2)alkyl, C(3-4)cycloalkylC(1-3)alkyl, cyclopropyl, methylamino or C(3-4)cycloalkylamino.

In another embodiment the invention relates to a compound according to Formula I wherein R1 is ethyl, cyclopropylamino or cyclopropylmethyl.

In another embodiment the invention relates to a compound according to Formula I wherein R1 is ethyl.

In yet another embodiment the invention relates to a compound according to Formula I wherein $R_1$ is cyclopropylamino.

In again another embodiment the invention relates to a compound according to Formula I wherein $R_1$ is cyclopropylmethyl.

In yet another embodiment the invention relates to a compound according to Formula I wherein $R_2$ and $R_3$ independently are H, methyl or hydroxy, H being the most preferred.

The invention also relates to a compound according to Formula I wherein $R_4$ is H or C(1-2)alkyl, H being the most preferred.

In yet another embodiment $R_5$ is H, hydroxyethyl, methoxyethyl or C(1-6)alkyl, all alkyl groups optionally being substituted with one or more F.

In again another embodiment $R_5$ in Formula I is H or C(1-3)alkyl, H being the most preferred.

In another embodiment $R_5$ in Formula I is C(6-10)arylC(1-3)alkyl or C(3-6)cycloalkylC(1-3)alkyl.

In again another embodiment $R_5$ in Formula I is C(6)arylC(1-3)alkyl or C(3-6)cycloalkylC(1-3)alkyl.

In again another embodiment $R_5$ in Formula I is benzyl.

In another embodiment the invention relates to a compound according to Formula I wherein $R_6$-$R_{10}$ are H. In this case, however, one of the groups $R_7$, $R_5$ or $R_9$ is the sulfonyl group with $R_1$ attached to it.

In yet another embodiment the sulfonyl group is represented by $R_8$, i.e. the sulfonyl group is attached at the para position of the aryl ring.

In yet another embodiment the sulfonyl group is represented by $R_8$, i.e. the sulfonyl group is attached at the para position of the aryl ring, $R_{10}$ is methyl and the remaining $R_6$-$R_9$ are H.

In yet another embodiment the sulfonyl group is represented by $R_7$ or $R_9$, i.e. the sulfonyl group is attached at the meta position of the aryl ring.

In yet another embodiment the invention relates to a compound according to Formula I wherein $R_{11}$-$R_{14}$ are independently H, halogen, methyl or methoxy, H being preferred.

In yet another embodiment the invention relates to a compound according to Formula I wherein $A_{11}$-$A_{14}$ are carbon atoms.

In yet another embodiment the invention relates to a compound according to Formula I wherein $A_{11}$ is nitrogen.

In yet another embodiment the invention relates to a compound according to Formula I wherein $A_{12}$ is nitrogen.

In one embodiment the invention relates to a compound according to Formulae I wherein $R_{15}$ and $R_{16}$ are independently C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkyl-C(1-3)alkyl, all groups optionally substituted with one or more F, Cl, C(1-2)alkyl, C(1-2)alkoxy or cyano.

In one embodiment the invention relates to a compound according to Formula I wherein either $R_{15}$ or $R_{16}$ is $CF_3$.

In another embodiment the invention relates to a compound according to Formula I wherein $R_{15}$ is $CF_3$ and $R_{16}$ is C(1-6)alkyl, C(3-6)cycloalkyl, C(3-6)cycloalkylC(1-3)alkyl, C(6)aryl or C(6)arylC(1-3)alkyl.

In another embodiment the invention relates to a compound according to Formula I wherein $R_{15}$ is $CF_3$ and $R_{16}$ is H, C(1-6)alkyl, C(3-6)cycloalkyl or C(3-6)cyclo-alkylC(1-3)alkyl, C(1-6)alkyl being the most preferred.

In another embodiment the invention relates to a compound according to Formula I wherein $R_{15}$ is $CF_3$ and $R_{16}$ is C(1-6)alkyl, C(3-6)cycloalkyl or C(3-6)cyclo-alkylC(1-3)alkyl, C(1-6)alkyl being the most preferred.

In yet another embodiment the invention relates to a compound according to Formula I wherein $R_{15}$ is $CF_3$ and $R_{16}$ is cyclopropyl, cyclopentyl or cyclohexylmethyl.

In yet another embodiment the invention also relates to a compound according to Formula I wherein $R_{15}$ is $CF_3$ and Rib is $CF_3$, propyl, isopropyl, 2-methylpropyl or 2,2-dimethylpropyl.

In another embodiment the invention also relates to a compound according to Formula I wherein both $R_{15}$ and $R_{16}$ are $CF_3$.

In yet another embodiment the invention also relates to a compound according to Formula I wherein both $R_{15}$ and $R_{16}$ are cyclopropyl.

The invention also relates to those compounds wherein all specific definitions for $A_{11}$ through $A_{14}$, $R_1$ through $R_{16}$, and all substituent groups in the various aspects of the inventions defined here above occur in any combination within the definition of the compound of Formula I.

In another aspect the invention relates to compounds of Formula I which have a pIC50 of 5 or higher. In yet another aspect the invention relates to compounds according to Formula I with a pIC50 of more than 6. In yet another aspect the invention relates to compounds according to Formula I with a pIC50 of more than 7. In yet another aspect the invention relates to compounds according to Formula I with a pIC50 of more than 8.

In yet another aspect the invention resides in the compounds according to Formula I selected as described in examples 1-114.

In yet another aspect the invention resides in the compounds according to Formula I selected as described in examples 1-41 and example 112.

The compounds of Formula I can form salts, which are also within the scope of this invention. Reference to a compound of Formula I herein is understood to include reference to salts thereof, unless otherwise indicated.

The compounds of Formula I may contain asymmetric or chiral centers and, therefore, exist in different stereoisomeric forms. It is intended that all stereoisomeric forms of the compounds of Formula I as well as mixtures thereof, including racemic mixtures, form part of the present invention.

Diastereomeric mixtures can be separated into their individual diastereomers on the basis of their physical chemical differences by methods well known to those skilled in the art, such as, for example, chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Enantiomers can also be separated by use of chiral HPLC column.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds.

The skilled artisan will recognize that desirable IC50 values are dependent on the compound tested. For example, a compound with an IC50 value less than $10^{-5}$ M is generally considered a candidate for drug selection. Preferably, this value is lower than $10^{-6}$ M. However, a compound which has a higher IC50 value, but is selective for the particular receptor, may be even a better candidate.

The compounds of the invention inhibit RORγ activity. Modulation of RORγ activity can be measured using for example biophysical (natural) ligand displacement studies, biochemical AlphaScreen or FRET assays, cellular GAL4 reporter gene assays, cellular IL-17 promotor reporter assay or functional IL-17 ELISA assays using for example mouse splenocytes or human peripheral blood mononuclear cells (PBMCs) cultured under $T_H17$ polarizing conditions (Solt et al, Nature 472, 491-494, 2011).

In such assays, the interaction of a ligand with RORγ can be determined by measuring, for example, the ligand modulated interaction of cofactor-derived peptides with the RORγ ligand binding domain, or measuring the gene products of ligand modulated RORγ mediated transcription using, for example, luciferase reporter assays or IL-17 ELISA assays.

The present invention also relates to a pharmaceutical composition comprising compounds or pharmaceutically acceptable salts thereof having the general Formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a compound of Formula I in combination with one or more other drug(s).

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: The Science and Practice of Pharmacy (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple sub-doses administered at appropriate intervals throughout the day.

The compounds according to the invention can be used in therapy.

A further aspect of the invention resides in the use of compounds according to the invention or a pharmaceutically acceptable salt thereof for the treatment of RORγ-mediated diseases or RORγ mediated conditions.

Another aspect of the invention resides in the use of compounds having the general Formula I or a pharmaceutically acceptable salt thereof for the treatment of autoimmune diseases, in particular those diseases in which Th17 cells and non-Th17 cells, which express Th17 hallmark cytokines play a prominent role. These include, but are not limited to, the treatment of rheumatoid arthritis, psoriasis, inflammatory bowel disease, Crohn's disease and multiple sclerosis.

In another aspect, compounds having the general Formula I or a pharmaceutically acceptable salt thereof can be used for treatment of inflammatory diseases in which Th17 cells and/or non-Th17 cells, which express Th17 hallmark cytokines play a prominent role such as, but not limited to respiratory diseases, osteoarthritis and asthma. Also, compounds or a pharmaceutically acceptable salt thereof having the general Formula I can be used for treatment of infectious diseases in which Th17 cells and/or non-Th17 cells, which express Th17 hallmark cytokines play a prominent role such as, but not limited to mucosal leishmaniasis.

Compounds having the general Formula I or a pharmaceutically acceptable salt thereof can also be used for treatment of other diseases in which Th17 cells and/or non-Th17 cells, which express Th17 hallmark cytokines play a prominent role such as, but not limited to Kawaski disease and Hashimoto's thyroiditis.

In yet another aspect the invention resides in the use of compounds having the general Formula I for the treatment of multiple sclerosis, inflammatory bowel disease. Crohn's disease, psoriasis, rheumatoid arthritis, asthma, osteoarthritis. Kawaski disease, Hashimoto's thyroiditis, cancer and mucosal leishmaniasis.

In another aspect, the compounds according to the invention can be used in therapies to treat or prevent multiple sclerosis, inflammatory bowel disease. Crohn's disease, psoriasis and rheumatoid arthritis, asthma, osteoarthritis. Kawaski disease, Hashimoto's thyroiditis, cancer and mucosal leishmaniasis.

In another aspect the compounds according to the invention can be used to treat or prevent psoriasis.

In yet another aspect the compounds according to the invention can be used to treat inflammatory bowel disease.

The invention is illustrated by the following examples,

EXAMPLES

General Methods of Preparation.

The compounds described herein, including compounds of general Formula I, building block II and building block III are prepared by the reaction schemes depicted below. Furthermore, in the following schemes, where specific acids, bases, reagents, coupling agents, solvents, etc. are mentioned, it is understood that other suitable acids, bases, reagents, coupling agents, solvents etc. may be used and are included within the scope of the present invention. Modifications to the reaction conditions, for example, temperature, duration of the reaction or combinations thereof, are envisioned as part of the present invention. The compounds obtained by using the general reaction sequences may be of insufficient purity. The compounds can be purified by using any of the methods for purification of organic compounds, for example, crystallization or silica gel or alumina column chromatography using different solvents in suitable ratios. All possible stereoisomers are envisioned within the scope of the invention.

Chemical names are preferred IUPAC names, generated using ChemBioDraw, version 12.0.

If a chemical compound is referred to using both a chemical structure and a chemical name, and an ambiguity exists between the structure and the name, the structure predominates.

Abbreviations used herein are as follow: HATU: 2-(7-Aza-1 H-benzotriazole-1-yl)-1,1,3,3-tetramethyluronium hexafluorophosphate; DMF: Dimethylformamide; DiPEA: Diisopropylethylamine; DMAP: 4-(dimethylamino)pyridine; DCC: N,N'-Dicyclohexylcarbodiimide; mCPBA: 3-chloroperoxybenzoic acid; TFA: Trifluoroacetic acid; TFAA: Trifluoroacetic anhydride; THF: Tetrahydrofuran; DMSO: Dimethylsulfoxide; PTSA: p-Toluenesulfonic acid; PyBOP: (Benzotriazol-1-yloxy)tripyrrolidinophosphonium hexafluorophosphate; EtOH: Ethanol; DIAD: Diisopropyl azodicarboxylate; TLC: Thin Layer Chromatography; Pd(dba)$_2$: Bis(dibenzylideneacetone)palladium(0); PPh3: Triphenyl phosphine; NMP; N-Methyl-2-pyrrolidinone; EDCI: 1-Ethyl-3-(3-dimethylaminopropyl)carbodiimide; BuLi: n-Butyl lithium; TBAF: Tetra-N-butylammonium fluoride; TMS: Trimethylsilyl.

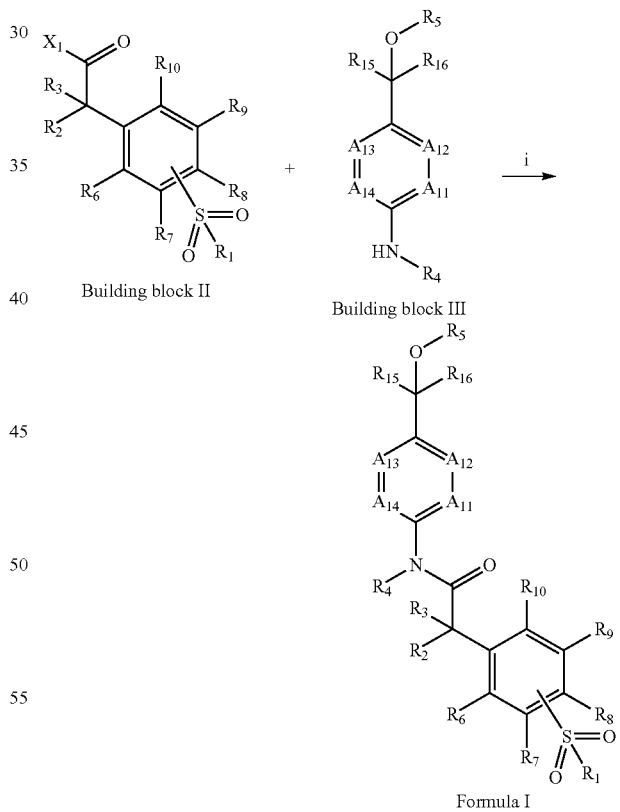

Conditions: i) DCC, DMAP, CH$_2$Cl$_2$.

As depicted in scheme 1, the derivatives of the invention having Formula I can be prepared by methods known in the art of organic chemistry. Compounds of the invention can for example be obtained by an amide coupling reaction between a phenylacetic acid derivative of building block II ($X_1$ is OH), wherein $R_1$, $R_2$, $R_3$, $R_6$, $R_7$, $R_8$, $R_9$ and $R_{10}$ have the meaning as previously described, and an aniline derivative of building block III, wherein $R_4$, $R_5$, $R_{15}$, $R_{16}$, $A_{11}$, $A_{12}$, $A_{13}$ and $A_{14}$ have the meaning as previously described, using a coupling reagent such as EDCI, HATU, DCC, or PyBOP or the like, in the presence of a suitable base such as DiPEA or DMAP.

Alternatively, the phenylacetic acid derivative of building block II ($X_1$=OH) can be converted into an acid chloride derivative of building block II ($X_1$=Cl), using for example $SOCl_2$ or oxalyl chloride. The obtained acid chloride derivative of building block II ($X_1$=Cl), wherein $R_1$, $R_2$, $R_3$, $R_6$, $R_7$, $R_8$, $R_9$ and $R_{10}$ have the meaning as previously described, can be coupled with an aniline derivative of building block III, wherein $R_4$, $R_5$, $R_{15}$, $R_{16}$, $A_{11}$, $A_{12}$, $A_{13}$ and $A_{14}$ have the meaning as previously described in the presentce of a suitable base such as $Et_3N$ or the like.

acid derivatives of building block II wherein $R_1$, $R_2$, $R_3$, $R_6$, $R_7$, $R_9$ and $R_{10}$ have the meaning as previously described.

Scheme 3

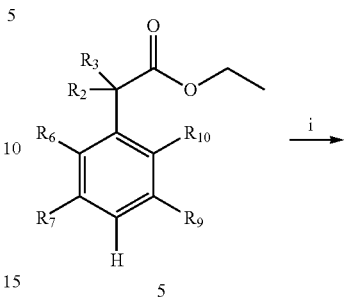

5

Scheme 2

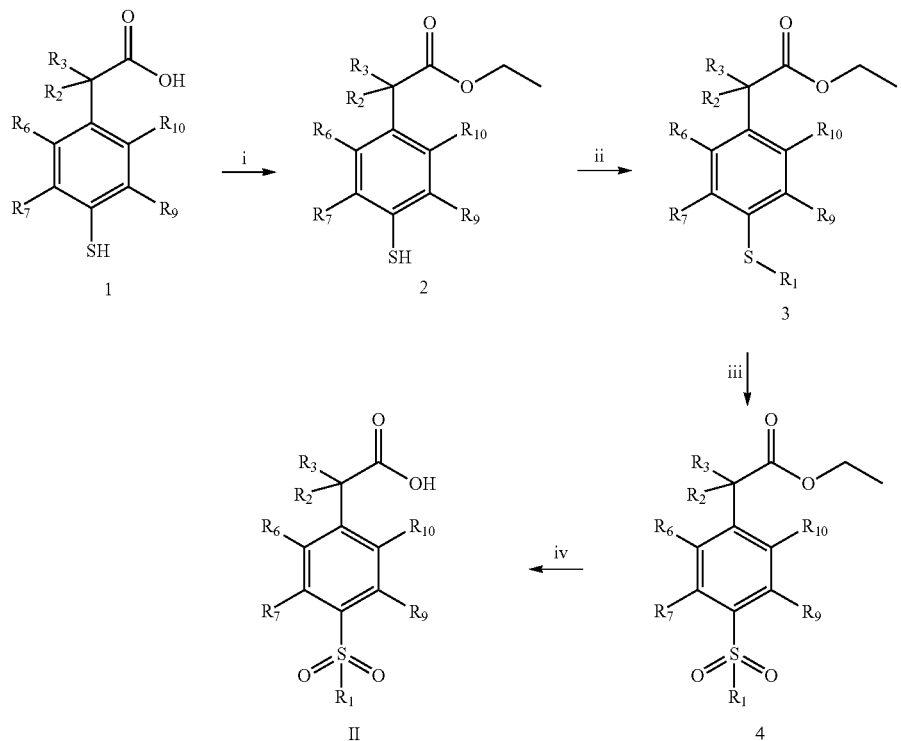

Conditions: i) $H_2SO_4$, EtOH; ii) R1-halide, $K_2CO_3$; iii) mCPBA; iv) 2N NaOH, EtOH Scheme 2 illustrates a general method for preparing sulfonylphenylacetic acid derivatives of building block II wherein $R_1$, $R_2$, $R_3$, $R_6$, $R_7$, $R_9$ and $R_{10}$ have the meaning as previously described.

Esterification of 4-mercatophenylacetic acid derivatives 1 under acidic conditions, using for example $H_2SO_4$ in EtOH provides 4-mercaptophenylacetic acid ethylester 2. Alkylation of the sulfur group using an alkylhalide in the presence of a base, such as $K_2CO_3$, gives the corresponding sulfanylphenylacetate derivatives 3 ($R_1$=e.g. Alkyl, cycloalkyl, cycloalkyl alkyl). Oxidation, using e.g. mCPBA, gives sulfonylphenylacetate derivatives 4 which after saponification of the ester moiety under basic conditions, e.g. NaOH in EtOH, gives the corresponding phenylacetic -continued

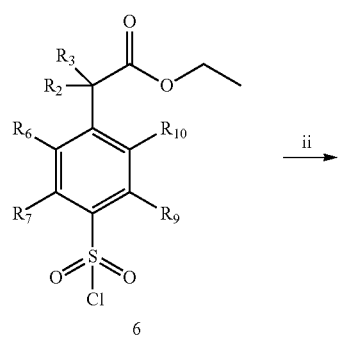

6

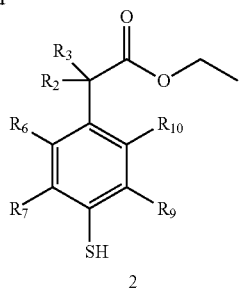

Conditions: i) Chlorosulfonic acid, $CH_2Cl_2$; ii) Tin, 5N HCl in 2-propanol or dioxane.

Scheme 3 illustrates an alternative route for the synthesis of mercaptophenyl acetate derivatives 2 wherein $R_2$, $R_3$, $R_6$, $R_7$, $R_9$ and $R_{10}$ have the meaning as previously described.

Reaction of 2-phenylacetic acid ethylester derivatives 5 with chlorosulfonic acid at 0° C. to room temperature, provides sulfonylchloride derivatives 6, (J. Med. Chem., 2009, 52, 19, 6142-6152). The chlorosulfone moiety can be reduced by using tin in the presence of HCl in a suitable solvent such as dioxane or 2-propanol to give the desired mercaptophenyl acetate derivatives 2.

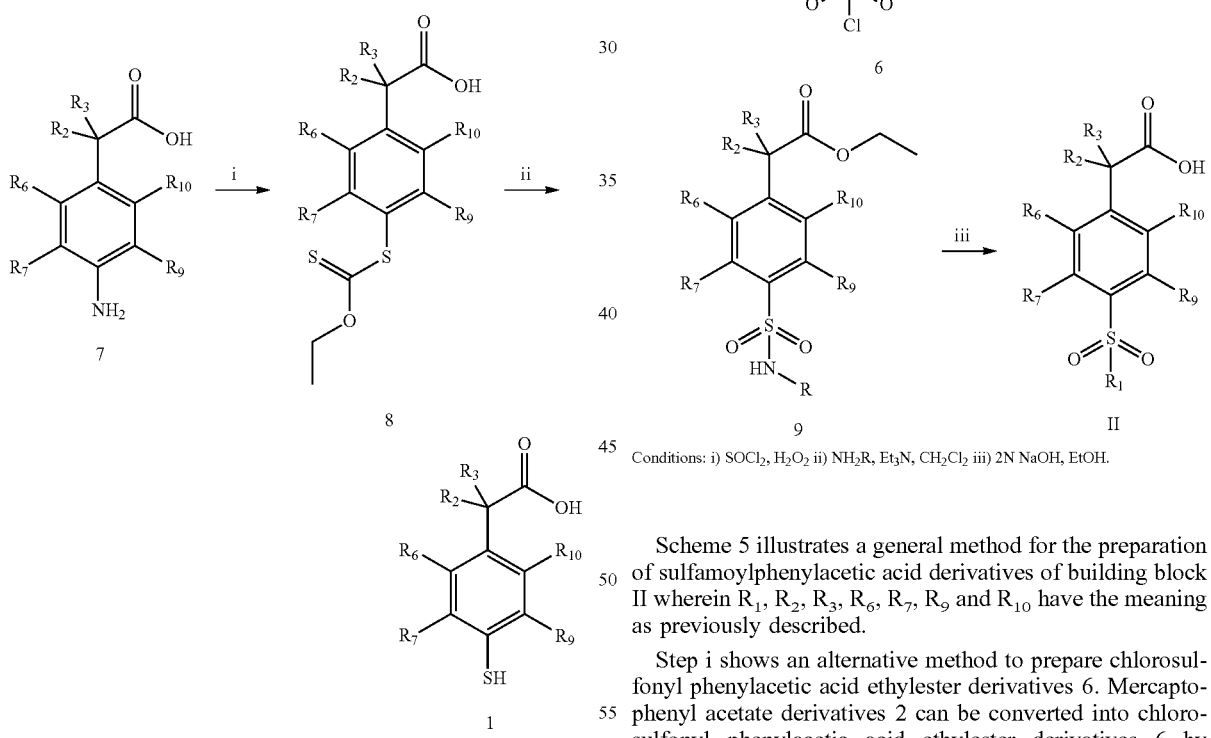

Conditions: i) $NaNO_2$, HCl $_{(conc)}$, Potassium ethylxanthate, 2N $Na_2CO_3$; ii) KOH, EtOH Scheme 4 illustrates a general method for the synthesis of 4-mercatophenylacetic acid derivatives 1 wherein $R_2$, $R_3$, $R_6$, $R_7$, $R_9$ and $R_{10}$ have the meaning as previously described.

Aminophenylacetic acid derivatives 7 can be converted into their corresponding diazonium salts by using methods well known in organic chemistry, which then, after treatment with potassium ethylxanthate in the presence of a base, e.g. $Na_2CO_3$, are converted in-situ into the 2-(4-(((ethoxymethanethioyl)sulfanyl)phenyl)acetic acid derivatives 8. Treating compound 8 with for example KOH in EtOH gives the desired 4-mercatophenylacetic acid derivatives 1.

Scheme 5

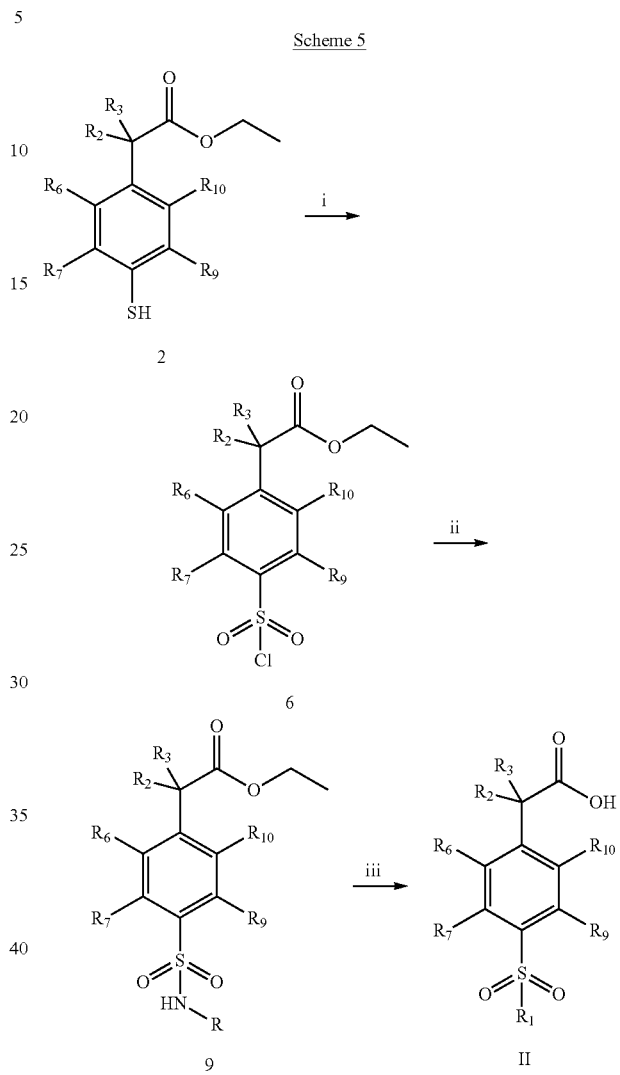

Conditions: i) $SOCl_2$, $H_2O_2$ ii) $NH_2R$, $Et_3N$, $CH_2Cl_2$ iii) 2N NaOH, EtOH.

Scheme 5 illustrates a general method for the preparation of sulfamoylphenylacetic acid derivatives of building block II wherein $R_1$, $R_2$, $R_3$, $R_6$, $R_7$, $R_9$ and $R_{10}$ have the meaning as previously described.

Step i shows an alternative method to prepare chlorosulfonyl phenylacetic acid ethylester derivatives 6. Mercaptophenyl acetate derivatives 2 can be converted into chlorosulfonyl phenylacetic acid ethylester derivatives 6 by oxidative chlorination using a mixture of $H_2O_2$ and $SOCl_2$ in a suitable solvent such as $CH_3CN$, (Bahrami et al., J. Org. Chem. 2009, 74, 9287-9291).

Substitution of the chlorine with a suitable amine, wherein R is e.g. alkyl, cycloalkyl or cycloalkylalkyl, in the presence of a base, e.g. $Et_3N$, provides the sulfamoylphenylacetic acid ethyl ester derivatives 9. Saponification of the ethylester under basic conditions, e.g. NaOH in EtOH, gives the desired sulfamoylphenylacetic acid derivatives of building block II wherein $R_1$, $R_2$, $R_3$, $R_6$, $R_7$, $R_9$ and $R_{10}$ have the meaning as previously described.

Scheme 6:

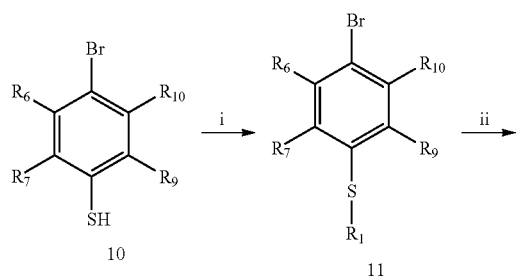

Scheme 6 illustrates an alternative route for the synthesis of sulfanyl acetate derivatives 3 wherein $R_1$, $R_2$, $R_3$, $R_6$, $R_7$, $R_9$ and $R_{10}$ have the meaning as previously described.

Alkylation of 4-bromobenzethiol derivatives 10, using an alkylhalide in the presence of a base, such as $K_2CO_3$, gives the corresponding 4-bromophenylsulfane derivatives 11 ($R_1$=e.g. alkyl, cycloalkyl, cycloalkyl alkyl).

Derivatives 11 can be converted into the corresponding sulfanyl acetate derivatives 3 by a palladium catalyzed coupling with dietyl malonate.

Scheme 7:

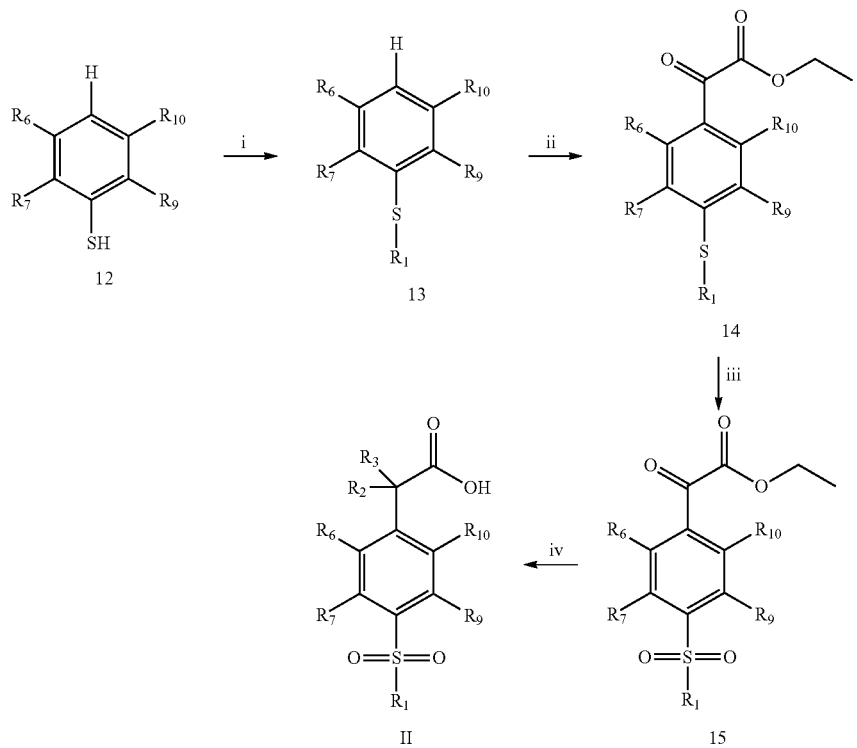

Conditions: ($R_2$ and $R_3$ together is carbonyl): i) $K_2CO_3$, Alkylhalide, $CH_3CN$; ii) ethyl oxalylchloride, $AlCl_3$, $CH_2Cl_2$; iii) mCPBA, $CH_2Cl_2$; iv) 2N NaOH, ethanol.

-continued

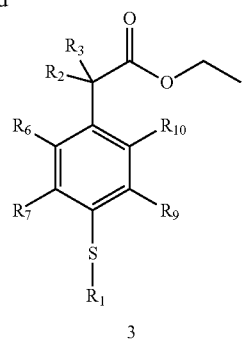

Conditions: i) R1-halide, $K_2CO_3$; ii) Diethyl malonate, Pd(dba)$_2$, 18-crown-6, P(tBu)$_3$·xHBF$_4$, $K_3PO_4$.

Scheme 7 illustrates a route for the synthesis of sulfonylphenyl-2-oxoacetic acid derivatives ($R_2$ and $R_3$ together is carbonyl) of building block II wherein $R_1$, $R_6$, $R_7$, $R_9$ and $R_{10}$ have the meaning as previously described.

Alkylation of thiophenol derivatives 12, using an alkyihalide in the presence of a base, such as $K_2CO_3$, gives the corresponding phenylsulfane derivatives 13 ($R_1$=e.g. alkyl, cycloalkyl, cycloalkylalkyl) which, under Friedel-Craft acylation conditions, in the presence of $AlCl_3$ and ethyl oxalylchloride, can be converted to the corresponding ethyl thiophenyl-2-oxoacetate derivatives 14. Oxidation, using e.g. mCPBA gives ethyl sulfonylphenyl-2-oxopropanoate derivatives 15 which after saponification of the ester moiety under basic conditions, e.g. NaOH in EtOH, give the corresponding sulfonylphenyl-2-oxopropanoic acid derivatives ($R_2$ and $R_3$ together is carbonyl) of building block II wherein $R_1$, $R_6$, $R_7$, $R_9$ and $R_{10}$ have the meaning as previously described.

Scheme 8

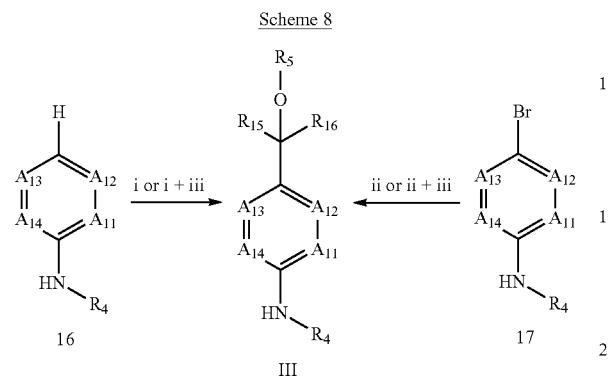

Conditions: i) ($R_{15}$, $R_{16}$ = $CF_3$, $R_5$ = H), Hexafluoroacetone hydrate; ii) BuLi, ketone; iii) DIAD, PPh$_3$, DMAP, $R_5$OH.

Scheme 8 shows two general methods for the preparation of (4-aminophenyl) methanol derivatives of building block III, wherein $R_4$, $R_5$, $R_{15}$, $R_{16}$, $A_{11}$, $A_{12}$, $A_{13}$ and $A_{14}$ have the meaning as previously described.

If $R_{15}$ and $R_{16}$ are both $CF_3$, then heating the aniline derivatives 16 in 1,1,1,3,3,3-hexafluoroacetone hydrate as the solvent in a sealed tube in a microwave, provides in one step 2-(4-aminophenyl)-1,1,1,3,3,3-hexafluoropropan-2-ol derivatives ($R_5$=H) of building block III.

Alternatively, the 1,1,1,3,3,3-hexafluoropropan-2-ol moiety can be introduced by treating suitable (N-protected) bromoaniline derivatives 17 with n-butyl lithium to form the corresponding lithiated intermediate, which then can be converted by treatment with 1,1,1,3,3,3-hexafluoroacetone gas to the desired 2-(4-aminophenyl)-1,1,1,3,3,3-hexafluoropropan-2-ol derivatives ($R_5$=H) of building block III. This method can also be used for the introduction of other tertiary alcohols, by using e.g. dry acetone, dry dicyclopropylmethanone or the like, as the corresponding ketone.

The alcohol derivatives of building block III ($R_5$=H) can, for example, be converted under Mitsunobu conditions, using e.g. DIAD, PPh$_3$, DMAP and a suitable alcohol, to the corresponding ether derivatives of building block III ($R_5$=e.g. alkyl, cycloalkyl).

Scheme 9

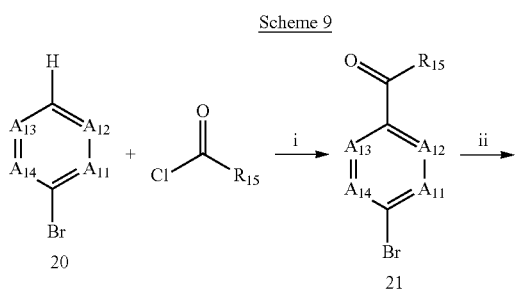

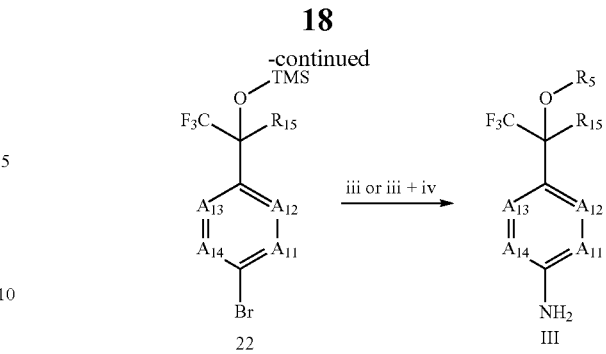

Conditions: i) AlCl$_3$, CH$_2$Cl$_2$; ii) TMSCF$_3$, CsF, Toluene/CH$_2$Cl$_2$; iii) NH$_4$OH, Cu$_2$O, NMP, 80° C., microwave; iv) DIAD, PPh$_3$, DMAP, R$_5$OH.

Scheme 9 shows a general method for the preparation of 1-(4-aminophenyl)-2,2,2-trifluoroethanol derivatives of building block III, wherein $R_5$, $R_{15}$, $A_{11}$, $A_{12}$, $A_{13}$ and $A_{14}$ have the meaning as previously described.

(Hetero)aryl bromides 20 can be converted under Friedel-Crafts acylation conditions, using AlCl$_3$ and a suitable acid chloride in e.g. CH$_2$Cl$_2$, to the corresponding 1-(4-bromophenyl)ketone derivatives 21, which can, e.g. via a cesium fluoride or TBAF catalyzed trifluoromethylation, be converted to the corresponding TMS protected 1-(4-aminophenyl)-2,2,2-trifluoroethanol derivatives 22 (Sing et al., J. Org. Chem., 64, p 2873 (1999). Copper catalyzed amination, using Cu$_2$O in the presence of ammonia (Wolf and Xu, Chem. Comm., p. 3035 (2009), results in the formation of 1-(4-aminophenyl)-2,2,2-trifluoroethanol derivatives III ($R_5$=H). These alcohol derivatives of building block III can, for example, be converted under Mitsunobu conditions, using e.g. DIAD, PPh$_3$, DMAP and a suitable alcohol, to the corresponding ether derivatives of building block III ($R_5$=e.g. alkyl, cycloalkyl).

Scheme 10

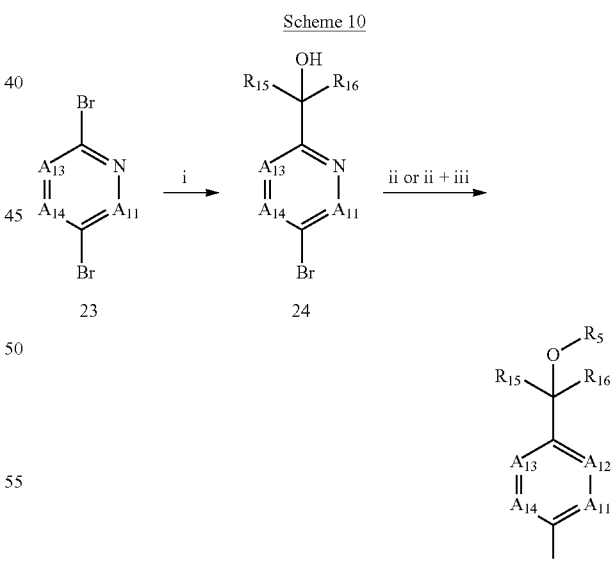

Conditions: ($A_{12}$ = N): i) BuLi, hexafluoroacetone, toluene; ii) NH$_4$OH, Cu$_2$O, NMP, 80° C., microwave; iii) DIAD, PPh$_3$, DMAP, R$_5$OH.

Scheme 10 depicts a general method for the preparation of (5-aminopyridin-2-yl)methanol derivatives of building block III ($A_{12}$=N), wherein $R_5$, $R_{15}$, $R_{16}$, $A_{11}$, $A_{13}$ and $A_{14}$ have the meaning as previously described.

The $R_{15}$, $R_{16}$-alcohol moiety can be introduced by treating suitable dibromopyridine derivatives 23 with n-butyl lithium to form the corresponding lithiated intermediate, which then can be converted by treatment with the corresponding ketone, e.g. 1,1,1,3,3,3-hexafluoroacetone gas, dry acetone or the like, to the corresponding (5-bromopyridin-2-yl)methanol derivatives 24. Copper catalyzed amination, using $Cu_2O$ in the presence of ammonia, results in the formation of (5-aminopyridin-2-yl)methanol derivatives of building block III ($A_{12}$=N, $R_5$=H). These alcohol derivatives of building block III can, for example, be converted under Mitsunobu conditions, using e.g. DIAD, $PPh_3$, DMAP and a suitable alcohol, to the corresponding ether derivatives of building block III ($A_{12}$=N, $R_5$=e.g. alkyl, cycloalkyl).

Synthesis of Building Blocks II

Building Blocks II-1-II-6

II-1: 2-(4-(isopropylsulfonyl)phenyl)acetic acid.

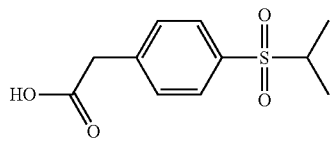 [SMILES: CC(C)S(=O)(=O)c1ccc(CC(=O)O)cc1]

i) To a solution of 2-(4-mercaptophenyl)acetic acid (10.0 g) in ethanol (120 mL) was added drop wise concentrated sulfuric acid (3.4 mL). The reaction mixture was stirred for 3 hours at 60° C. After cooling to room temperature, the reaction mixture was concentrated under reduced pressure and the remaining oil was neutralized with a saturated aqueous $NaHCO_3$ solution. The product was extracted into ethyl acetate and the combined organic phases were washed with water, brine, dried over magnesium sulfate, and after filtration, concentrated under reduced pressure. The residue was purified on $SiO_2$ using 10% ethyl acetate in heptane as the eluent to give ethyl 2-(4-mercaptophenyl)acetate (10.2 g) as colourless liquid.

ii) To a suspension of the product obtained in the previous step (5.0 g) and potassium carbonate (8.6 g) in acetonitrile (50 mL) was added 2-bromopropane (2.8 mL). After stirring overnight at room temperature, the reaction mixture was filtered and concentrated under reduced pressure. The residue was purified on $SiO_2$ using 10% ethyl acetate in heptane as the eluent to give ethyl 2-(4-(isopropylthio)phenyl)acetate (5.34 g) as a colourless liquid.

iii) To a cooled (0° C.) solution of the product obtained in the previous step (5.3 g) in $CH_2Cl_2$ (50 mL), was added portion wise mCPBA (11.5 g). After stirring overnight at room temperature, the reaction mixture was filtered and the organic phase was washed with a saturated aqueous $NaHCO_3$ solution, water, brine, dried over magnesium sulfate and concentrated under reduced pressure. The residue was purified on $SiO_2$ using 10% ethyl acetate in heptane as the eluent. To give ethyl 2-(4-(isopropylsulfonyl)phenyl) acetate (4.4 g) as a clear oil.

iv) To a solution of the product obtained in the previous step (4.4 g) in ethanol (50 mL), was added an aqueous 2N NaOH solution. After stirring overnight at room temperature, ethanol was removed under reduced pressure and 100 mL water was added. The aqueous solution was washed with $CH_2Cl_2$, acidified to pH=1 with an aqueous 6N HCl solution and the product was then extracted into ethyl acetate. The combined organic layers were washed with water, brine, dried over magnesium sulfate and concentrated under reduced pressure to give the title compound 2-(4-(isopropylsulfonyl)phenyl)acetic acid (3.6 g) as a white solid. $MS(ES^+)$ m/z 243.2 $[M+H]^+$.

Following a procedure analogous to that described for compound II-1, using a suitable alkylating reagent (step ii), the following compounds were prepared.

II-2: 2-(4-(methylsulfonyl)phenyl)acetic acid.

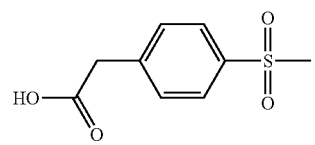

$MS(ES^+)$ m/z 215.2 $[M+H]^+$.

II-3: 2-(4-(ethylsulfonyl)phenyl)acetic acid.

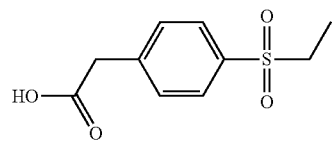

$MS(ES^+)$ m/z 229.1 $[M+H]^+$.

II-4: 2-(4-(propylsulfonyl)phenyl)acetic acid.

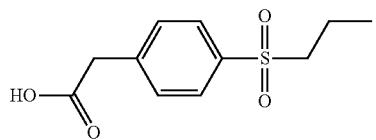 [SMILES: CCCS(=O)(=O)c1ccc(CC(=O)O)cc1]

$MS(ES^+)$ m/z 243.2 $[M+H]^+$.

II-5: 2-(4-(isobutylsulfonyl)phenyl)acetic acid.

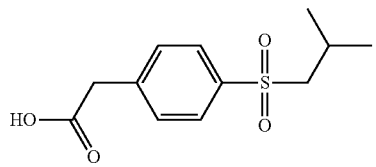 [SMILES: CC(C)CS(=O)(=O)c1ccc(CC(=O)O)cc1]

$MS(ES^+)$ m/z 257.2 $[M+H]^+$.

II-6: 2-(4-((cyclopropylmethyl)sulfonyl)phenyl)acetic acid.

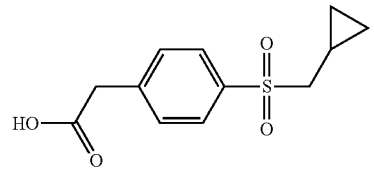 [SMILES: O=C(O)Cc1ccc(S(=O)(=O)CC2CC2)cc1]

MS(ES$^+$) m/z 255.2 [M+H]$^+$.
Building Blocks II-7 and II-8
II-7: 2-(4-(ethylsulfonyl)phenyl)propanoic acid

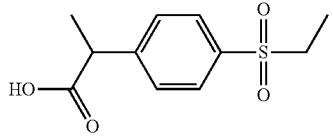 [SMILES: CCS(=O)(=O)c1ccc(C(C)C(=O)O)cc1]

i) Following a procedure described for compound II-1, step i, 2-phenylpropanoic acid (5.0 g) was converted to ethyl 2-phenylpropanoate (4.4 g).

ii) A solution of the product obtained in the previous step (4.4 g) in CH$_2$Cl$_2$ (30 mL) was added drop wise at 0° C. to chlorosulfonic acid (21.7 mL). After stirring for 3 hours at room temperature the reaction mixture was quenched by carefully pouring it onto crushed ice. The product was extracted into ethyl acetate and the combined organic layers were washed with water, brine and dried over magnesium sulfate. After filtration, the solvent was removed under reduced pressure to give ethyl 2-(4-(chlorosulfonyl)phenyl)propanoate (5.3 g) as a brown solid. The crude product was used in the next step without purification.

iii) To a suspension of the product obtained in the previous step (5.3 g) and tin powder (12.0 g) in ethanol (50 mL), was added a 4N solution of HCl in dioxane (27 mL). The reaction mixture was stirred at 65° C. for 3 hours under a nitrogen atmosphere. The reaction mixture was quenched by pouring it onto crushed ice. The product was extracted into CH$_2$Cl$_2$ and the organic layer was washed with water and dried over magnesium sulfate. After filtration, the solvent was removed under reduced pressure. The residue was purified on SiO$_2$, using 10% ethyl acetate in heptane as the eluent to give ethyl 2-(4-mercaptophenyl)propanoate (2.8 g) as a colourless liquid.

iv) Following a procedure described for compound II-1, step ii to iv, the product obtained in the previous step (1.0 g), using iodoethane (0.46 mL) as the alkylating reagent, was converted to the title compound 2-(4-(ethylsulfonyl)phenyl)propanoic acid (0.82 g). MS(ES$^+$) m/z 243.2 [M+H]$^+$.

Following a procedure analogous to that described for compound II-7, using a suitable alkylating reagent (step iv), the following compound was prepared.

II-8: 2-(4-((cyclopropylmethyl)sulfonyl)phenyl)propanoic acid.

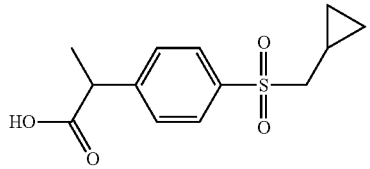 [SMILES: CC(C(=O)O)c1ccc(S(=O)(=O)CC2CC2)cc1]

MS(ES$^+$) m/z 268.1 [M+H]$^+$.
Building Blocks II-9-II-17
II-9: 2-(4-(N-methylsulfamoyl)phenyl)acetic acid.

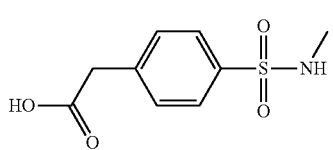

i) Following a procedure described for compound II-7, step ii, ethyl 2-phenylacetate (1.87 g) was converted to ethyl 2-(4-(chlorosulfonyl)phenyl)acetate.

ii) To a solution of the product obtained in the previous step (1 g) in CH$_2$Cl$_2$ was added methylamine hydrochloride (0.31 g mmol). After stirring for 17 hours at room temperature, the reaction mixture was washed with water, dried over magnesium sulfate and concentrated under reduced pressure. The residue was purified on SiO$_2$ using 10% to 20% ethyl acetate in heptane as the eluent to give ethyl 2-(4-(N-methylsulfamoyl)phenyl)acetate as a solid (0.41 g).

iii) Following a procedure described for compound II-1, step iv, the product obtained in the previous step (0.41 g) was converted to the title compound 2-(4-(N-methylsulfamoyl)phenyl)acetic acid. (0.35 g). MS(ES$^+$) m/z 230.2 [M+H]$^+$.

Following a procedure analogous to that described for compound II-9, the following compounds were prepared.

II-10: 2-(4-(N,N-dimethylsulfamoyl)phenyl)acetic acid.

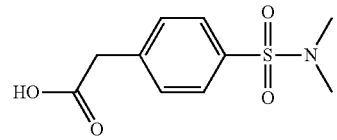 [SMILES: CN(C)S(=O)(=O)c1ccc(CC(=O)O)cc1]

MS(ES$^+$) m/z 244.1 [M+H]$^+$.
II-11: 2-(4-(N-ethylsulfamoyl)phenyl)acetic acid.

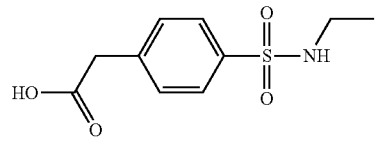

MS(ES$^+$) m/z 244.1 [M+H]$^+$.
II-12: 2-(4-(N-propylsulfamoyl)phenyl)acetic acid.

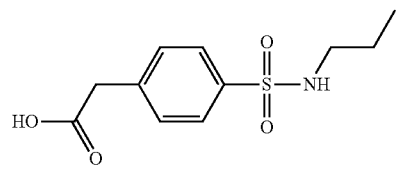

MS(ES$^+$) m/z 258.2 [M+H]$^+$.
II-13: 2-(4-(N-isobutylsulfamoyl)phenyl)acetic acid.

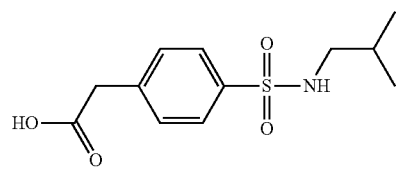 [SMILES: CC(C)CNS(=O)(=O)c1ccc(CC(=O)O)cc1]

MS(ES$^+$) m/z 272.2 [M+H]$^+$.

II-14: 2-(4-(N-isopropylsulfamoyl)phenyl)acetic acid.

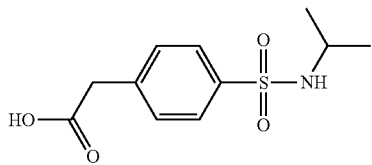

MS(ES+) m/z 258.2 [M+H]+.
II-15: 2-(4-(N-cyclopropylsulfamoyl)phenyl)acetic acid.

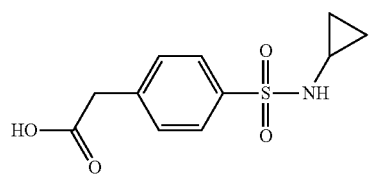 [SMILES: O=C(O)Cc1ccc(S(=O)(=O)NC2CC2)cc1]

MS(ES+) m/z 256.2 [M+H]+.
II-16: 2-(4-(N-(cyclopropylmethyl)sulfamoyl)phenyl)acetic acid.

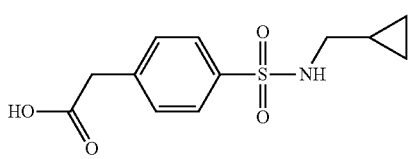 [SMILES: O=C(O)Cc1ccc(S(=O)(=O)NCC2CC2)cc1]

MS(ES+) m/z 270.2 [M+H]+.
II-17: 2-(4-(N-cyclobutylsulfamoyl)phenyl)acetic acid.

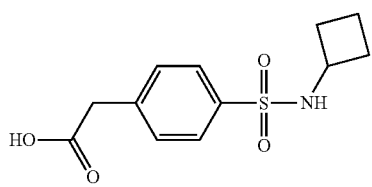 [SMILES: O=C(O)Cc1ccc(S(=O)(=O)NC2CCC2)cc1]

MS(ES+) m/z 270.1 [M+H]+.
Building Blocks II-18-II-22
II-18: 2-(3-(ethylsulfonyl)phenyl)acetic acid.

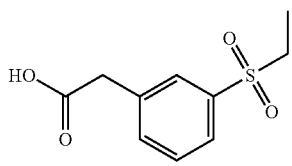

i) A solution of sodium nitrite (0.916 g) in 20 mL of water was added drop wise to a suspension of 2-(3-aminophenyl)acetic acid (2 g) in 20 mL of water and 2.7 mL of concentrated hydrochloric acid cooled to 0° C. After the addition was complete, the reaction mixture was stirred at the same temperature for a further 45 minutes. This cold diazonium salt solution was then added drop wise to a mixture of potassium O-ethyl carbonodithioate (2.456 g), 20 mL of water and 10 mL of a 2N Na$_2$CO$_3$ solution at room temperature. The reaction mixture was heated at 45° C. until gas evolution stopped. The mixture was subsequently cooled to room temperature, the pH was adjusted to 1 with concentrated HCl. The oily product was extracted into diethyl ether and the organic layer was washed with water, brine, dried over magnesium sulfate and concentrated under reduced pressure to give 2-(3-((ethoxycarbonothioyl)thio)phenyl)acetic acid (4.8 g) as a dark red liquid which was used in the next step without purification.

ii) To a solution of the product obtained in the previous step (4.8 g) in ethanol (50 mL) was added an aqueous solution of KOH (1.05 g). The reaction mixture was heated at reflux for 20 hours. The organic solvent was removed under reduced pressure and the remaining aqueous phase was cooled with ice and acidified with concentrated HCl. The product was extracted into diethyl ether and the organic phase was washed with water, brine, dried over magnesium sulfate and concentrated under reduced pressure to give the 2-(3-mercaptophenyl)acetic acid (3.3 g) as a brown solid which was used in the next step without purification.

iii) Following a procedure described for compound II-1, step i to iv, the product obtained in the previous step (0.97 g), using iodoethane (0.42 mL) as the alkylating reagent, was converted to the title compound 2-(3-(ethylsulfonyl)phenyl)acetic acid. MS(ES+) m/z 229.2 [M+H]+.

Following a procedure analogous to that described for compound II-18, the following compounds were prepared.

II-19: 2-(3-(isopropylsulfonyl)phenyl)acetic acid.

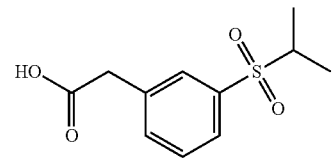 [SMILES: CC(C)S(=O)(=O)c1cccc(CC(=O)O)c1]

MS(ES+) m/z 243.2 [M+H]+.
II-20: 2-(3-(propylsulfonyl)phenyl)acetic acid.

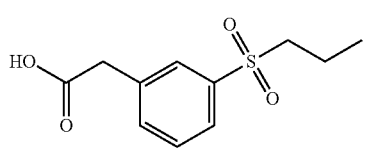 [SMILES: CCCS(=O)(=O)c1cccc(CC(=O)O)c1]

MS(ES+) m/z 243.1 [M+H]+.
II-21: 2-(3-(isobutylsulfonyl)phenyl)acetic acid.

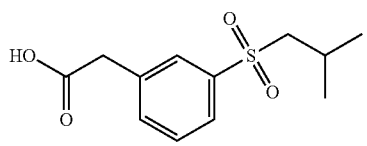 [SMILES: CC(C)CS(=O)(=O)c1cccc(CC(=O)O)c1]

MS(ES+) m/z 257.2 [M+H]+.

II-22: 2-(3-((cyclopropylmethyl)sulfonyl)phenyl)acetic acid.

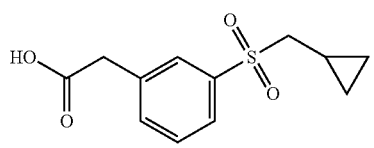 [SMILES: O=C(O)Cc1cccc(S(=O)(=O)CC2CC2)c1]

MS(ES+) m/z 255.2 [M+H]+.

Building Blocks II-23-II-29

II-23: 2-(3-(N-methylsulfamoyl)phenyl)acetic acid.

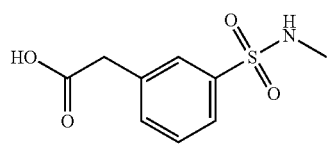

i) A mixture of ethyl 2-(3-mercaptophenyl)acetate (compound II-18, step ii, 0.1 g), 30% $H_2O_2$ in water (155 uL) and $SOCl_2$ (61 uL) was stirred in $CH_3CN$ at 25° C. for 10 minutes. After completion as indicated by TLC, a solution of methylamine hydrochloride (0.04 g) in pyridine (0.5 ml) was added to the reaction mixture. After stirring for 15 minutes at room temperature, the reaction mixture was acidified with an aqueous 2N HCl solution, and the product was extracted into ethyl acetate. The organic layer was washed with water, brine, dried over magnesium sulfate and concentrated under reduced pressure to give ethyl 2-(3-(N-methylsulfamoyl) phenyl) acetate (0.21 g) as a yellow oil which was used in the next step without purification.

ii) Following a procedure described for compound II-1, step iv, the product obtained in the previous step (0.2 g) was converted to the title compound 2-(3-(N-methylsulfamoyl) phenyl)acetic acid (0.083 g). MS(ES+) m/z 230.2 [M+H]+.

Following a procedure analogous to that described for compound II-23, the following compounds were prepared.

II-24: 2-(3-(N,Ndimethylsulfamoyl)phenyl)acetic acid.

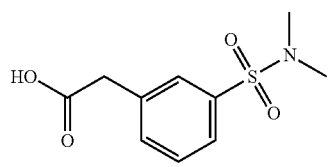 [SMILES: CN(C)S(=O)(=O)c1cccc(CC(=O)O)c1]

MS(ES+) m/z 244.2 [M+H]+.

II-25: 2-(3-(N-ethylsulfamoyl)phenyl)acetic acid.

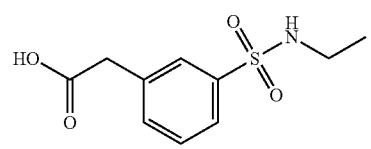 [SMILES: CCNS(=O)(=O)c1cccc(CC(=O)O)c1]

MS(ES+) m/z 244.2 [M+H]+.

II-26: 2-(3-N-cyclopropylsulfamoyl)phenyl)acetic acid.

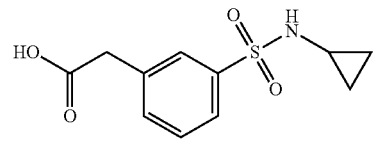 [SMILES: O=C(O)Cc1cccc(S(=O)(=O)NC2CC2)c1]

MS(ES+) m/z 256.1 [M+H]+

II-27: 2-(3-(N-(cyclopropylmethyl)sulfamoyl)phenyl) acetic acid.

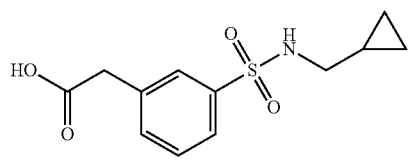 [SMILES: O=C(O)Cc1cccc(S(=O)(=O)NCC2CC2)c1]

MS(ES+) m/z 270.1 [M+H]+.

II-28: 2-(3-(N-propylsulfamoyl)phenyl)acetic acid.

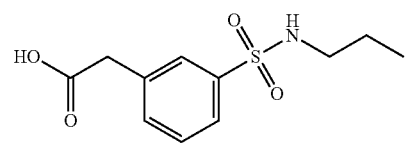 [SMILES: CCCNS(=O)(=O)c1cccc(CC(=O)O)c1]

MS(ES+) m/z 258.1 [M+H]+.

II-29: 2-(3-(N-cyclobutylsulfamoyl)phenyl)acetic acid.

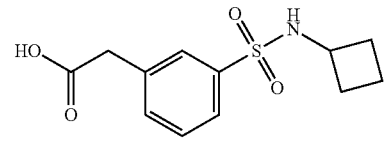 [SMILES: O=C(O)Cc1cccc(S(=O)(=O)NC2CCC2)c1]

MS(ES+) m/z 270.2 [M+H]+.

II-30: 2-(4-((cyclopropylmethyl)sulfonyl)phenyl)-2-oxoacetic acid.

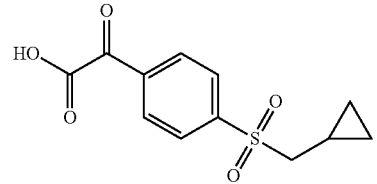 [SMILES: O=C(O)C(=O)c1ccc(S(=O)(=O)CC2CC2)cc1]

i) Following a procedure analogous to that described for compound II-1, step ii, benzenethiol (4.0 g) was converted to (cyclopropylmethyl)(phenyl)sulfane (5.68 g).

ii) To a cold (0° C.) suspension of $AlCl_3$ (6.44 g) in $CH_2Cl_2$ was added drop wise, under a nitrogen atmosphere, ethyl oxalyl chloride (4.25 mL). After stirring for 30 minutes at 0° C., the product obtained in the previous step (5.68 g), was added drop wise. The purple solution was allowed to warm to room temperature. After stirring for another 2 hours at ambient temperature, the reaction mixture was quenched by pouring it onto ice water. CH$_2$Cl$_2$ was added and the layers were separated. The aqueous phase was washed twice with CH$_2$Cl$_2$ and the combined organic phases were washed with brine, dried over magnesium sulfate and concentrated under reduced pressure. The residue was purified on SiO$_2$, using 0% to 100% ethyl acetate in heptane as the eluent to give ethyl 2-(4-((cyclopropylmethyl)thio)phenyl)-2-oxoacetate (5.57 g) as a yellow oil.

iii) To a cold solution (0° C.) of the product obtained in the previous step (1.0 g) in CH$_2$Cl$_2$ (25 mL) was added portion wise mCPBA (1.95 g). After stirring for 17 hours at room temperature the reaction mixture was filtered. The filtrate was washed with a saturated aqueous NaHCO$_3$ solution, water, brine, dried over magnesium sulfate and concentrated under reduced pressure. The residue was purified on SiO$_2$, using 0% to 90% ethyl acetate in heptane as the eluent to give ethyl 2-(4-((cyclopropylmethyl)sulfonyl)phenyl)-2-oxoacetate (0.3 g).

iv) To a solution of the product obtained in the previous step (0.3 g) in ethanol (10 mL) was added an aqueous 2N NaOH solution (1.80 mL) and the reaction mixture was stirred for 17 hours at room temperature. The solvent was removed under reduced pressure and water was added (100 mL). The aqueous solution was washed with CH$_2$Cl$_2$ and then acidified with an aqueous 6N HCl solution to pH=1. This aqueous phase was washed with ethyl acetate and the organic phase was washed brine, dried over magnesium sulfate and concentrated under reduced pressure to give the title compound 2-(4-((cyclopropylmethyl)sulfonyl)phenyl)-2-oxoacetic acid (0.25 g) as a clear oil.

MS(ES$^+$) m/z 268.2 [M+H]$^+$.

II-31: 2-(4-((cyclopropylmethyl)sulfonyl)-2-methylphenyl)acetic acid.

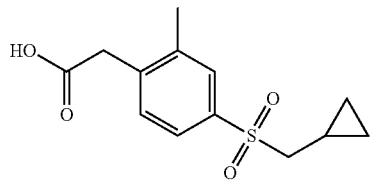 [SMILES: Cc1cc(S(=O)(=O)CC2CC2)ccc1CC(=O)O]

i) (Bromomethyl)cyclopropane (170 uL) was added to a mixture of 4-bromo-3-methylbenzenethiol (300 mg) and K$_2$CO$_3$ (511 mg) in CH$_3$CN (15 mL) and the reaction mixture was stirred at room temperature for 3.5 hours. The reaction mixture was filtered and the filtrate was concentrated under reduced pressure. The residue was purified on SiO$_2$, using 5% ethyl acetate in heptane as the eluent to give (4-bromo-3-methylphenyl)(cyclopropylmethyl)sulfane (95 mg).

ii) A mixture of the product obtained in the previous step (95 mg), diethylmalonate (390 mg), K$_3$PO$_4$ (220 mg) and 18-crown-6 (49 mg) in a microwave tube was purged with nitrogen for 10 minutes. Pd(dba)$_2$ (1 mg) and P(tBu)$_3$.xHBF$_4$ (1 mg) were added and the reaction was heated, in a sealed tube, in a microwave for 3 hours at 160° C. After cooling to room temperature the reaction mixture was diluted with ethyl acetate and the solution was washed with water. The organic phase was washed with water and the combined organic layers were washed with brine, dried over magnesium sulfate and concentrated under reduced pressure. The residue was purified on SiO$_2$, using 10% ethyl acetate in heptane as the eluent to give ethyl 2-(4-((cyclopropylmethyl)thio)-2-methylphenyl)acetate (60 mg).

iii) Following a procedure described for compound II-1, step iii to iv, the product obtained in the previous step (60 mg), was converted to the title compound 2-(4-((cyclopropylmethyl)sulfonyl)-2-methylphenyl)acetic acid (28 mg) as a white solid.

MS(ES$^+$) m/z 296.4 [M+H]$^+$.

Synthesis of Building Blocks III

Building Blocks III-1-III-8

III-1: 2-(4-aminophenyl)-1,1,1,3,3,3-hexafluoropropan-2-ol.

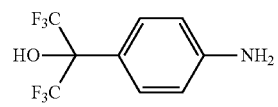

i) A mixture of aniline (392 uL) and hexafluoroacetone trihydrate (600 uL) were heated, in a sealed tube, in a microwave at 150° C. for 2 hours. The crude product was crystallized from heptane with 20% ethyl acetate to give the title compound 2-(4-aminophenyl)-1,1,1,3,3,3-hexafluoropropan-2-ol (490 mg) as a white solid. MS(ES$^+$) m/z 260.2 [M+H]$^+$.

Following a procedure analogous to that described for compound III-1, the following compounds were prepared.

III-2: 1,1,1,3,3,3-hexafluoro-2-(4-(methylamino)phenyl)propan-2-ol.

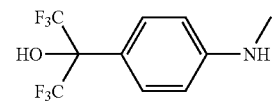

MS(ES$^+$) m/z 274.2 [M+H]$^+$.

III-3: 2-(4-amino-2-fluoro-3-methylphenyl)-1,1,1,3,3,3-hexafluoropropan-2-ol.

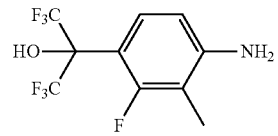 [SMILES: Cc1c(N)ccc(C(O)(C(F)(F)F)C(F)(F)F)c1F]

MS(ES$^+$) m/z 292.1 [M+H]$^+$.

III-4: 2-(4-amino-2-fluoro-5-methoxyphenyl)-1,1,1,3,3,3-hexafluoropropan-2-ol.

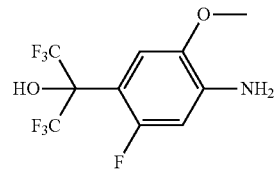 [SMILES: COc1cc(C(O)(C(F)(F)F)C(F)(F)F)c(F)cc1N]

MS(ES$^+$) m/z 308.2 [M+H]$^+$.

III-5: 2-(4-amino-2-chloro-5-methoxyphenyl)-1,1,1,3,3,3-hexafluoropropan-2-ol.

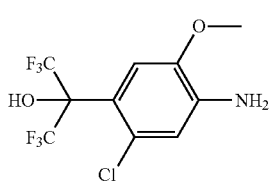 [SMILES: COc1cc(C(O)(C(F)(F)F)C(F)(F)F)c(Cl)cc1N]

MS(ES+) m/z 324.6 [M+H]+.

III-6: 2-(4-(ethylamino)phenyl)-1,1,1,3,3,3-hexafluoropropan-2-ol.

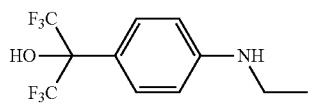

MS(ES+) m/z 288.2 [M+H]+.

III-7: 2-(4-amino-3,5-dimethylphenyl)-1,1,1,3,3,3-hexafluoropropan-2-ol.

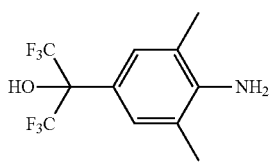

MS(ES+) m/z 288.2 [M+H]+.

II-8: 2-(6-aminopyridin-3-yl)-1,1,1,3,3,3-hexafluoropropan-2-ol.

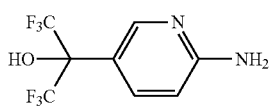

MS(ES+) m/z 261.2 [M+H]+.

Building Blocks III-9-III-12

The following compounds were purchased from Parkway Scientific:

III-9: 2-(4-amino-2-methylphenyl)-1,1,1,3,3,3-hexafluoropropan-2-ol.

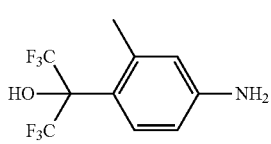

III-10: 2-(4-amino-2-fluorophenyl)-1,1,1,3,3,3-hexafluoropropan-2-ol.

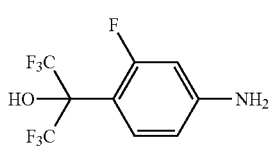

III-11: 2-(4-amino-3-methylphenyl)-1,1,1,3,3,3-hexafluoropropan-2-ol.

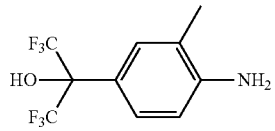

III-12: 2-(4-amino-3-fluorophenyl)-1,1,1,3,3,3-hexafluoropropan-2-ol.

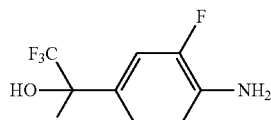

Building Blocks III-13-III-19

III-13: 4-(1,1,1,3,3,3-hexafluoro-2-methoxypropan-2-yl)aniline.

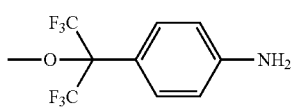

i) A solution of DIAD (141 uL) in THF (1 mL) was added drop wise to a solution of 2-(4-aminophenyl)-1,1,1,3,3,3-hexafluoropropan-2-ol (III-1) (100 mg), PPh3 (152 mg) and methanol (32 uL) in THF (1 mL) at 0° C. After stirring for 2 hours at room temperature the solvent was removed under reduced pressure and the remaining yellow oil was purified on a preparative HPLC using 5 to 90% CH3CN in water as the eluent to give the title compound 4-(1,1,1,3,3,3-hexafluoro-2-methoxypropan-2-yl)aniline (50 mg) as a white solid. MS(ES+) m/z 274.1 [M+H]+.

Following a procedure analogous to that described for compound III-13, the following compounds were prepared.

III-14: 4-(2-ethoxy-1,1,1,3,3,3-hexafluoropropan-2-yl)aniline.

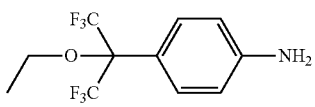

MS(ES+) m/z 288.1 [M+H]+.

III-15: 4-(1,1,1,3,3,3-hexafluoro-2-propoxypropan-2-yl)aniline.

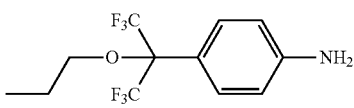

MS(ES+) m/z 302.1 [M+H]+.

III-16: 4-(2-butoxy-1,1,1,3,3,3-hexafluoropropan-2-yl)aniline.

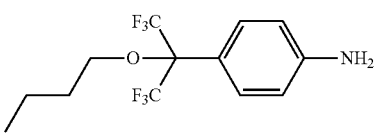 [SMILES: CCCCOC(c1ccc(N)cc1)(C(F)(F)F)C(F)(F)F]

MS(ES+) m/z 316.2 [M+H]+.

III-17: 4-(1,1,1,3,3,3-hexafluoro-2-isopropoxypropan-2-yl)aniline.

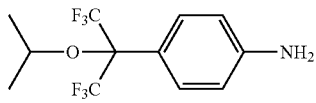

MS(ES⁺) m/z 302.1 [M+H]⁺.

III-18: 4-(2-(2-cyclopropylethoxy)-1,1,1,3,3,3-hexafluoropropan-2-yl)aniline.

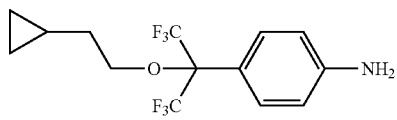

MS(ES⁺) m/z 328.1 [M+H]⁺.

III-19: 4-(2-(benzyloxy)-1,1,1,3,3,3-hexafluoropropan-2-yl)aniline.

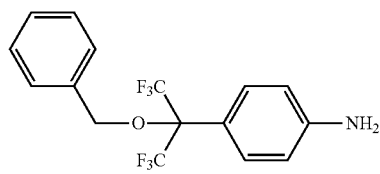

MS(ES⁺) m/z 350.1 [M+H]⁺.

Building Blocks III-20-III-32

III-20: 2-(4-aminophenyl)-1,1,1-trifluoropentan-2-ol.

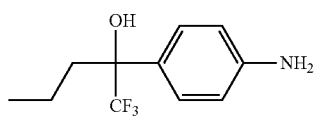 [SMILES: CCCC(O)(c1ccc(N)cc1)C(F)(F)F]

i) To a suspension of AlCl₃ (4.06 g) in bromobenzene (2.72 mL) was added drop wise butyrylchloride (2.66 mL). After addition was complete the reaction mixture was stirred at 50° C. for 2 hours under a nitrogen atmosphere. The reaction mixture was quenched by pouring it onto ice water and the product was extracted into ethyl acetate. The organic phase was washed with water, brine, dried over magnesium sulfate and concentrated under reduced pressure. The residue was purified on SiO₂, using 0% to 20% ethyl acetate in heptane as the eluent to give 1-(4-bromophenyl)butan-1-one (5.6 g) as a solid.

ii) To a solution of the product obtained in the previous step (1.0 g) in a mixture of toluene and CH₂Cl₂ (2 ml, 9:10) was added (trifluoromethyl)trimethylsilane (0.65 mL). To this suspension CsF (67 mg) was added. After a few minutes an exothermic reaction started and the reaction mixture was stirred for another 30 minutes until completion. The reaction mixture was quenched by the addition of water. The organic layer was washed with water, brine, dried over magnesium sulfate and concentrated under reduced pressure. The residue was purified on SiO₂, using 0% to 40% ethyl acetate in heptane as the eluent to give ((2-(4-bromophenyl)-1,1,1-trifluoropentan-2-yl)oxy)trimethylsilane (1.5 g) as a solid.

iii) To a solution of the product obtained in the previous step (1.5 g) in NMP (4 mL) were added Cu₂O (30 mg) and an aqueous NH₄OH solution (4 mL). The reaction mixture was stirred for 15 hours at 80° C. in a microwave. The blue reaction mixture was poured into water and the product was extracted into ethyl acetate. The organic layer was washed with water, brine, dried over magnesium sulfate and concentrated under reduced pressure to give the title compound 2-(4-aminophenyl)-1,1,1-trifluoropentan-2-ol, as a brown oil. The crude product was used without further purification. MS(ES⁺) m/z 234.1 [M+H]⁺.

Following a procedure analogous to that described for Example III-20, the following compounds were prepared.

III-21: 2-(4-aminophenyl)-1,1,1-trifluoropropan-2-ol.

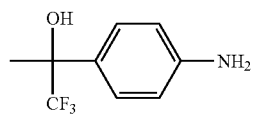

MS(ES⁺) m/z 206.1 [M+H]⁺.

III-22: 2-(4-aminophenyl)-1,1,1-trifluorobutan-2-ol.

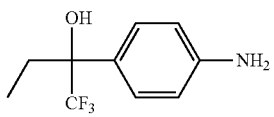

MS(ES⁺) m/z 2120.1 [M+H]⁺.

III-23: 2-(4-aminophenyl)-1,1,1-trifluorohexan-2-ol.

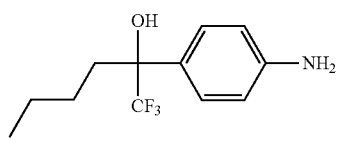 [SMILES: CCCCC(O)(c1ccc(N)cc1)C(F)(F)F]

MS(ES⁺) m/z 248.1 [M+H]⁺.

III-24: 2-(4-aminophenyl)-1,1,1-trifluoro-4-methylpentan-2-ol.

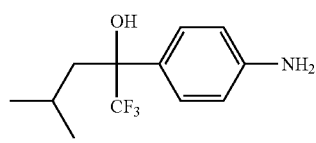 [SMILES: CC(C)CC(O)(c1ccc(N)cc1)C(F)(F)F]

MS(ES⁺) m/z 248.1 [M+H]⁺.

III-25: 2-(4-aminophenyl)-1,1,1-trifluoro-3-methylbutan-2-ol.

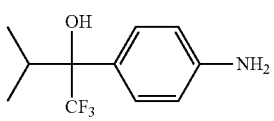 [SMILES: CC(C)C(O)(c1ccc(N)cc1)C(F)(F)F]

MS(ES⁺) m/z 234.1 [M+H]⁺.

III-26: 2-(4-aminophenyl)-1,1,1-trifluoro-3-phenylpropan-2-ol.

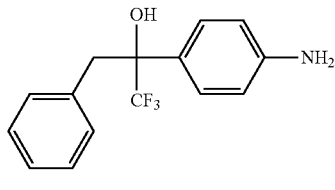 [SMILES: Nc1ccc(C(O)(Cc2ccccc2)C(F)(F)F)cc1]

MS(ES⁺) m/z 282.1 [M+H]⁺.

III-27: 2-(4-aminophenyl)-3-cyclopentyl-1,1,1-trifluoropropan-2-ol.

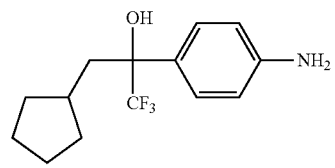 [SMILES: Nc1ccc(C(O)(CC2CCCC2)C(F)(F)F)cc1]

MS(ES⁺) m/z 274.1 [M+H]⁺.

III-28: 2-(4-aminophenyl)-3-cyclohexyl-1,1,1-trifluoropropan-2-ol.

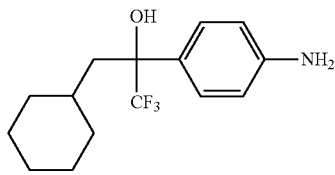 [SMILES: Nc1ccc(C(O)(CC2CCCCC2)C(F)(F)F)cc1]

MS(ES⁺) m/z 288.1 [M+H]⁺.

III-29: 1-(4-aminophenyl)-1-cyclopropyl-2,2,2-trifluoroethanol.

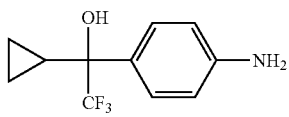 [SMILES: Nc1ccc(C(O)(C2CC2)C(F)(F)F)cc1]

MS(ES⁺) m/z 232.1 [M+H]⁺.

III-30: 1-(4-aminophenyl)-1-cyclopentyl-2,2,2-trifluoroethanol.

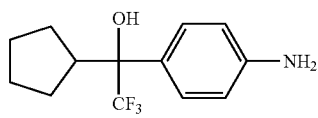 [SMILES: Nc1ccc(C(O)(C2CCCC2)C(F)(F)F)cc1]

MS(ES⁺) m/z 260.1 [M+H]⁺.

III-31: 2-(4-aminophenyl)-1,1,1-trifluoro-4,4-dimethylpentan-2-ol.

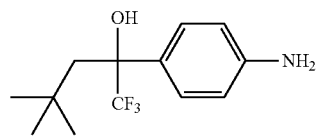

MS(ES⁺) m/z 262.1 [M+H]⁺.

III-32: 2-(4-aminophenyl)-1,1,1-trifluoro-6-methylheptan-2-ol.

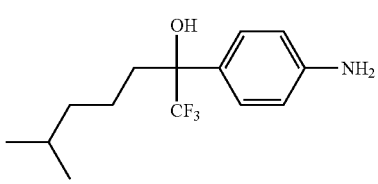 [SMILES: CC(C)CCCC(O)(c1ccc(N)cc1)C(F)(F)F]

MS(ES⁺) m/z 276.1 [M+H]⁺.

Building Blocks III-33 and III-34

III-33: 2-(4-aminophenyl)propan-2-ol.

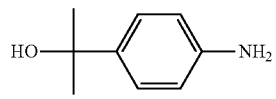

i) A solution of 4-bromoanilin (12.46 g) and di-tert-butyl dicarbonate (18.97 g) in THF (500 mL) was stirred at 80° C. for 24 hours. After cooling to room temperature the solvent was removed under reduced pressure and the remaining solid was transferred to a filter and washed with heptane. The filtrate was concentrated under reduced pressure and the remaining solids were washed with heptanes one more time. The combined solids were dried under reduced pressure at 40° C. to give tert-butyl (4-bromophenyl)carbamate (16.73 g) as a white solid.

ii) The product obtained in the previous step (1 g) was dissolved in dry THF (20 mL) in a dried 3-neck flask under a nitrogen atmosphere. The reaction mixture was cooled to −78° C. and BuLi (5.7 mL, 2.5 N in heptane) was added drop wise. After stirring for 1.5 hours at −78° C., dry acetone (296 uL) was added drop wise. The reaction mixture was allowed to warm to room temperature and stirred for another 17 hours. The reaction mixture was quenched by the addition of a saturated aqueous NH₄Cl solution. The product was extracted into ethyl acetate and the combined organic layers were washed with brine, dried over magnesium sulfate and concentrated under reduced pressure. The residue was purified on SiO₂, using 0% to 40% ethyl acetate in heptane as the eluent to give tert-butyl (4-(2-hydroxypropan-2-yl)phenyl)carbamate (210 mg).

iii) To a solution of the product obtained in the previous step (124 mg) in THF (2.5 mL) was added at room temperature a 1 M solution of TBAF in THF (987 uL). The reaction mixture was stirred at 80° C. for 17 hours. The reaction mixture was quenched by the addition of water and the product was extracted into ethyl acetate. The combined organic layers were washed with a saturated aqueous NaHCO₃ solution, brine, dried over magnesium sulfate and concentrated under reduced pressure. The residue was purified on SiO₂, using 0% to 45% ethyl acetate in heptane as the eluent to give title compound 2-(4-aminophenyl)propan-2-ol (44 mg). MS(ES⁺) m/z 134.1 [(M-18)+H]⁺.

¹H NMR(500 MHz, DMSO-d6): δ 7.12-7.05 (m, 2H), 6.52-6.44 (m, 2H), 4.82 (s, 2H), 4.66 (s, 1H), 1.35 (s, 6H).

Following a procedure analogous to that described for compound III-33, the following compound was prepared.

III-34: (4-aminophenyl)dicyclopropylmethanol.

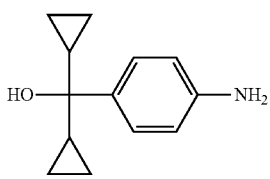

MS(ES⁺) m/z 186.1 [(M-18)+H]⁺.
¹H NMR(500 MHz, CDCl3): δ 7.40-7.34 (m, 2H), 6.67-6.62 (m, 2H), 3.62 (s, 2H), 1.39 (s, 1H), 1.26-1.11 (m, 2H), 0.57-0.45 (m, 4H), 0.39-0.32 (m, 4H).

III-35: 2-(5-aminopyridin-2-yl)-1,1,1,3,3,3-hexafluoropropan-2-ol.

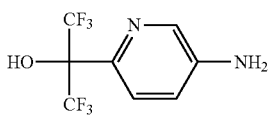

i) To a solution of 2,5-dibromopyridine (500 mg) in dry toluene (11 mL) was added dropwise at −78° C. a solution of n-BuLi in hexane (1.45 mL, 1.6 M). The reaction mixture was stirred at −78° C. for 30 minutes. Hexafluoroacetone gas was bubbled through for about 30 seconds and the reaction mixture was stirred for another 40 minutes at −78° C. After warming up to room temperature, the reaction mixture was washed with an aqueous 5% NH4Cl solution, water, brine, dried over magnesium sulfate and the solvent was removed under reduced pressure to give 2-(5-bromopyridin-2-yl)-1,1,1,3,3,3-hexafluoropropan-2-ol as a yellow oil (532 mg).

ii) To a solution of the product obtained in the previous step (532 mg) in NMP (2 mL) was added an aqueous 28% NH₄OH solution (2 mL) and Cu₂O (12 mg). The reaction mixture was stirred for 15 hours at 80° C. in a sealed tube. After cooling to room temperature, the blue reaction mixture was poured into water en extracted with ethyl acetate. The combined organic phases were washed with water, brine, dried over magnesium sulfate and concentrated under reduced pressure to give the title compound 2-(5-aminopyridin-2-yl)-1,1,1,3,3,3-hexafluoropropan-2-ol (95 mg) as a brown solid. MS(ES⁺) m/z 261.1 [M+H]⁺.

Examples 1-27

1: N-(4-(1,1,1,3,3,3-hexafluoro-2-hydroxypropan-2-yl)phenyl)-2-(4-(methylsulfonyl)phenyl)acetamide

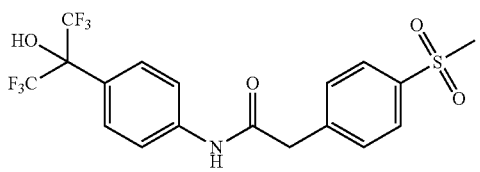 [SMILES: CS(=O)(=O)c1ccc(CC(=O)Nc2ccc(C(O)(C(F)(F)F)C(F)(F)F)cc2)cc1]

i) To a solution of acid II-2 (47 mg) and HATU (84 mg) in DMF (2 ml), were sequentially added DIPEA (79 uL) and aniline III-1 (57 mg) at room temperature. The reaction mixture was stirred at 40° C. for 3 hours. After cooling to room temperature, water was added and the product was extracted into ethyl acetate. The combined organic layers were washed with water, brine, dried over magnesium sulfate and concentrated under reduced pressure. The residue was purified on SiO₂, using 1% to 10% methanol in dichloromethane as the eluent, to give the title compound N-(4-(1,1,1,3,3,3-hexafluoro-2-hydroxypropan-2-yl)phenyl)-2-(4-(methylsulfonyl)phenyl)acetamide (70 mg) as a white solid. MS(ES⁺) m/z 243.2 [M+H]⁺.

¹H NMR(500 MHz, DMSO-d6): δ 10.46 (s, 1H), 8.61 (s, 1H), 7.88-7.86 (m, 2H), 7.71-7.68 (m, 2H), 7.59-7.56 (m, 4H), 3.80 (s, 2H), 3.17 (s, 3H).

Following a procedure analogous to that described for Example 1, using the appropriate building blocks II and III, the following compounds were prepared.

2: 2-(4-(ethylsulfonyl)phenyl)-N-(4-(1,1,1,3,3,3-hexafluoro-2-hydroxypropan-2-yl)phenyl)acetamide

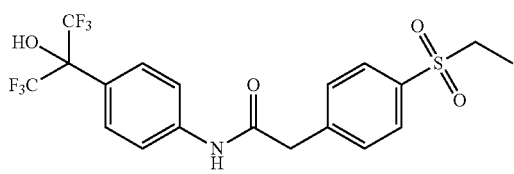 [SMILES: CCS(=O)(=O)c1ccc(CC(=O)Nc2ccc(C(O)(C(F)(F)F)C(F)(F)F)cc2)cc1]

MS(ES⁺) m/z 470.2 [M+H]⁺.

3: N-(4-(1,1,1,3,3,3-hexafluoro-2-hydroxypropan-2-yl)phenyl)-2-(4-(isopropylsulfonyl)phenyl)acetamide

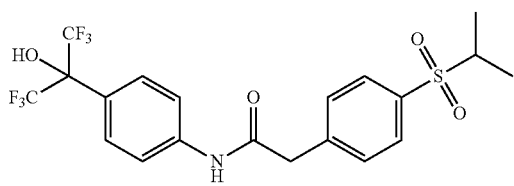 [SMILES: CC(C)S(=O)(=O)c1ccc(CC(=O)Nc2ccc(C(O)(C(F)(F)F)C(F)(F)F)cc2)cc1]

MS(ES⁺) m/z 484.2 [M+H]⁺.

4: N-(4-(1,1,1,3,3,3-hexafluoro-2-hydroxypropan-2-yl)phenyl)-2-(4-(propylsulfonyl)phenyl)acetamide

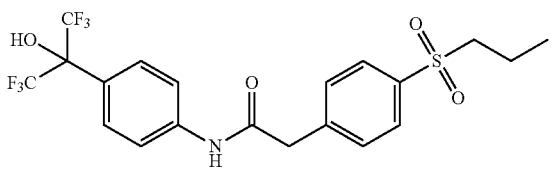 [SMILES: CCCS(=O)(=O)c1ccc(CC(=O)Nc2ccc(C(O)(C(F)(F)F)C(F)(F)F)cc2)cc1]

MS(ES⁺) m/z 484.2 [M+H]⁺.

5: 2-(4-(ethylsulfonyl)phenyl)-N-(4-(1,1,1,3,3,3-hexafluoro-2-hydroxypropan-2-yl)phenyl)propanamide

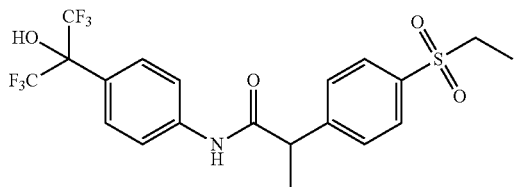 [SMILES: CCS(=O)(=O)c1ccc(C(C)C(=O)Nc2ccc(C(O)(C(F)(F)F)C(F)(F)F)cc2)cc1]

MS(ES⁺) m/z 484.2 [M+H]⁺.

6: N-(4-(1,1,1,3,3,3-hexafluoro-2-hydroxypropan-2-yl)phenyl)-2-(4-(N-methylsulfamoyl)phenyl)acetamide

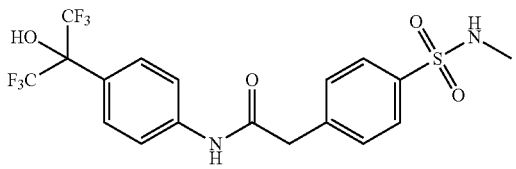 [SMILES: CNS(=O)(=O)c1ccc(CC(=O)Nc2ccc(C(O)(C(F)(F)F)C(F)(F)F)cc2)cc1]

MS(ES⁺) m/z 471.2 [M+H]⁺.

7: N-(4-(1,1,1,3,3,3-hexafluoro-2-hydroxypropan-2-yl)phenyl)-2-(4-(N-isopropylsulfamoyl)phenyl)acetamide

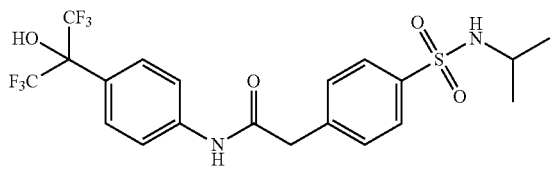 [SMILES: CC(C)NS(=O)(=O)c1ccc(CC(=O)Nc2ccc(C(O)(C(F)(F)F)C(F)(F)F)cc2)cc1]

MS(ES⁺) m/z 499.2 [M+H]⁺.

8: 2-(4-(N-(cyclopropylmethyl)sulfamoyl)phenyl)-N-(4-(1,1,1,3,3,3-hexafluoro-2-hydroxypropan-2-yl)phenyl)acetamide

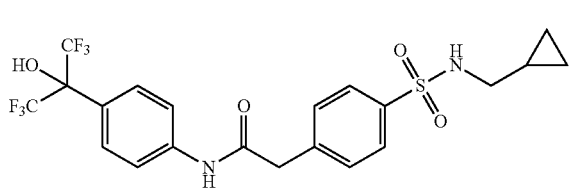 [SMILES: O=C(Cc1ccc(S(=O)(=O)NCC2CC2)cc1)Nc1ccc(C(O)(C(F)(F)F)C(F)(F)F)cc1]

MS(ES⁺) m/z 511.2 [M+H]⁺.

9: 2-(4-(N-cyclopropylsulfamoyl)phenyl)-N-(4-(1,1,1,3,3,3-hexafluoro-2-hydroxypropan-2-yl)phenyl)acetamide

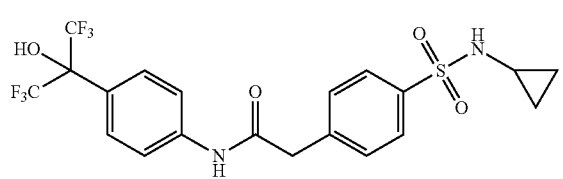 [SMILES: O=C(Cc1ccc(S(=O)(=O)NC2CC2)cc1)Nc1ccc(C(O)(C(F)(F)F)C(F)(F)F)cc1]

MS(ES⁺) m/z 497.2 [M+H]⁺.

10: 2-(4-(N-ethylsulfamoyl)phenyl)-N-(4-(1,1,1,3,3,3-hexafluoro-2-hydroxypropan-2-yl)phenyl)acetamide

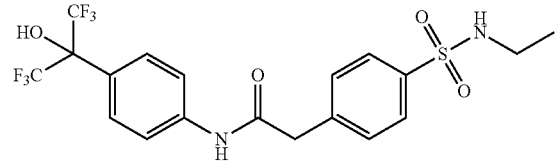 [SMILES: CCNS(=O)(=O)c1ccc(CC(=O)Nc2ccc(C(O)(C(F)(F)F)C(F)(F)F)cc2)cc1]

MS(ES⁺) m/z 485.1 [M+H]⁺.

11: 2-(4-(N,N-dimethylsulfamoyl)phenyl)-N-(4-(1,1,1,3,3,3-hexafluoro-2-hydroxypropan-2-yl)phenyl)acetamide

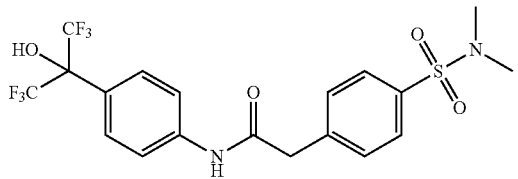 [SMILES: CN(C)S(=O)(=O)c1ccc(CC(=O)Nc2ccc(C(O)(C(F)(F)F)C(F)(F)F)cc2)cc1]

MS(ES⁺) m/z 485.1 [M+H]⁺.

12: 2-(3-(N-cyclopropylsulfamoyl)phenyl)-N-(4-(1,1,1,3,3,3-hexafluoro-2-hydroxypropan-2-yl)phenyl)acetamide

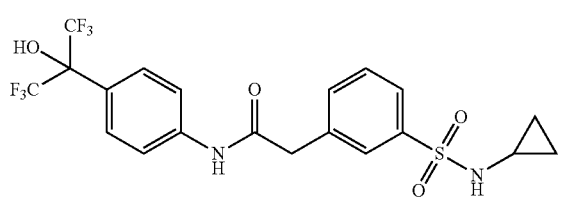 [SMILES: O=C(Cc1cccc(S(=O)(=O)NC2CC2)c1)Nc1ccc(C(O)(C(F)(F)F)C(F)(F)F)cc1]

MS(ES⁺) m/z 497.2 [M+H]⁺.

13: 2-(3-(N-ethylsulfamoyl)phenyl)-N-(4-(1,1,1,3,3,3-hexafluoro-2-hydroxypropan-2-yl)phenyl)acetamide

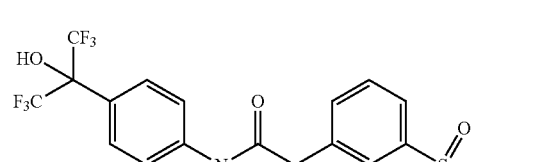

MS(ES⁺) m/z 485.2 [M+H]⁺.

14: 2-(3-(N,N-dimethylsulfamoyl)phenyl)-N-(4-(1,1,1,3,3,3-hexafluoro-2-hydroxypropan-2-yl)phenyl)acetamide

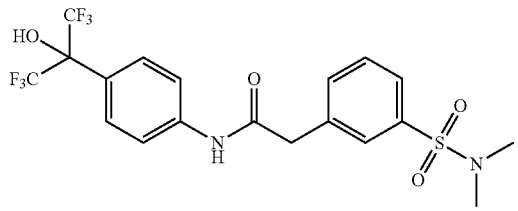 [SMILES: CN(C)S(=O)(=O)c1cccc(CC(=O)Nc2ccc(C(O)(C(F)(F)F)C(F)(F)F)cc2)c1]

MS(ES⁺) m/z 485.2 [M+H]⁺.

15: 2-(4-(ethylsulfonyl)phenyl)-N-(3-fluoro-4-(1,1,1,3,3,3-hexafluoro-2-hydroxypropan-2-yl)-2-methyl-phenyl)acetamide

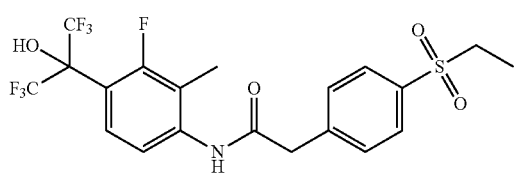 [SMILES: CCS(=O)(=O)c1ccc(CC(=O)Nc2ccc(C(O)(C(F)(F)F)C(F)(F)F)c(F)c2C)cc1]

MS(ES⁺) m/z 502.2 [M+H]⁺.

16: 2-(4-(N-cyclopropylsulfamoyl)phenyl)-N-(4-(1,1,1,3,3,3-hexafluoro-2-hydroxypropan-2-yl)phenyl)-N-methylacetamide

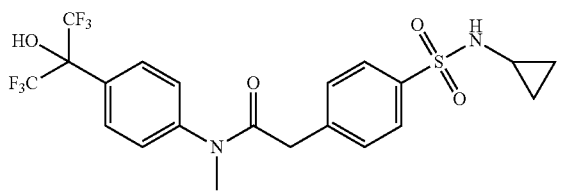 [SMILES: CN(C(=O)Cc1ccc(S(=O)(=O)NC2CC2)cc1)c1ccc(C(O)(C(F)(F)F)C(F)(F)F)cc1]

MS(ES⁺) m/z 511.1 [M+H]⁺.

17: 2-(4-(N-cyclopropylsulfamoyl)phenyl)-N-ethyl-N-(4-(1,1,1,3,3,3-hexafluoro-2-hydroxypropan-2-yl)phenyl)acetamide

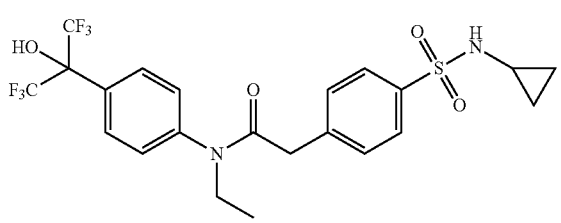 [SMILES: CCN(C(=O)Cc1ccc(S(=O)(=O)NC2CC2)cc1)c1ccc(C(O)(C(F)(F)F)C(F)(F)F)cc1]

MS(ES⁺) m/z 525.2 [M+H]⁺.

18: 2-(3-(N-cyclopropylsulfamoyl)phenyl)-N-(4-(1,1,1,3,3,3-hexafluoro-2-hydroxypropan-2-yl)phenyl)-N-methylacetamide

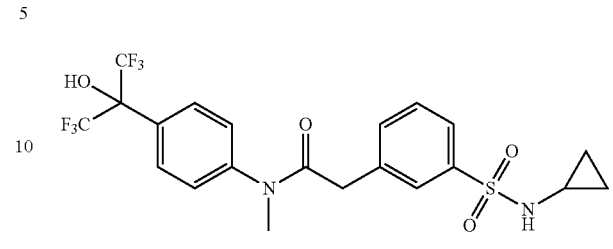

MS(ES⁺) m/z 511.2 [M+H]⁺.

19: N-(4-(1,1,1,3,3,3-hexafluoro-2-hydroxypropan-2-yl)phenyl)-2-(3-(N-methylsulfamoyl)phenyl)acetamide

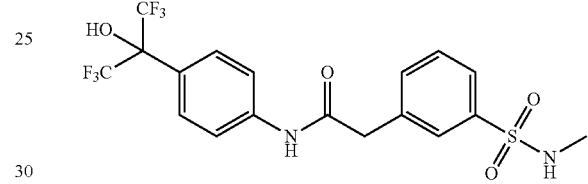

MS(ES⁺) m/z 471.2 [M+H]⁺.

20: 2-(4-(ethylsulfonyl)phenyl)-N-(5-fluoro-4-(1,1,3,3,3-hexafluoro-2-hydroxypropan-2-yl)-2-methoxyphenyl)acetamide

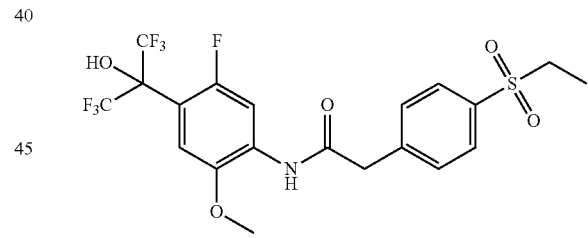

MS(ES⁺) m/z 518.2 [M+H]⁺.

21: 2-(4-(ethylsulfonyl)phenyl)-N-(5-(1,1,1,3,3,3-hexafluoro-2-hydroxypropan-2-yl)pyridin-2-yl)acetamide

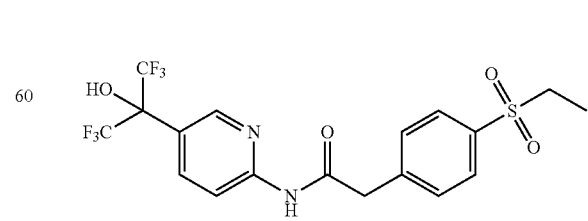

MS(ES⁺) m/z 471.2 [M+H]⁺.

22: N-(5-chloro-4-(1,1,1,3,3,3-hexafluoro-2-hydroxypropan-2-yl)-2-methoxyphenyl)-2-(4-(ethylsulfonyl)phenyl)acetamide

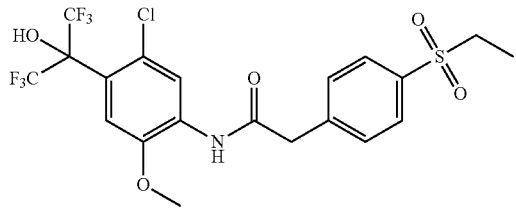 [SMILES: CCS(=O)(=O)c1ccc(CC(=O)Nc2cc(F)c(C(O)(C(F)(F)F)C(F)(F)F)cc2OC)cc1]

MS(ES⁺) m/z 534.2 [M+H]⁺.

23: 2-(4-(ethylsulfonyl)phenyl)-N-(4-(1,1,1,3,3,3-hexafluoro-2-hydroxypropan-2-yl)-2,6-dimethylphenyl)acetamide

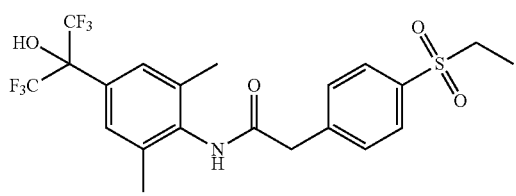 [SMILES: CCS(=O)(=O)c1ccc(CC(=O)Nc2c(C)cc(C(O)(C(F)(F)F)C(F)(F)F)cc2C)cc1]

MS(ES⁺) m/z 488.2 [M+H]⁺.

24: 2-(3-(N-cyclobutylsulfamoyl)phenyl)-N-(4-(1,1,1,3,3,3-hexafluoro-2-hydroxypropan-2-yl)phenyl)acetamide

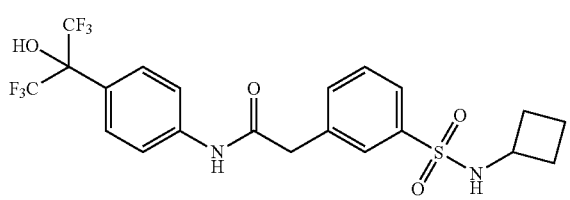 [SMILES: O=C(Cc1cccc(S(=O)(=O)NC2CCC2)c1)Nc1ccc(C(O)(C(F)(F)F)C(F)(F)F)cc1]

MS(ES⁺) m/z 511.2 [M+H]⁺.

25: 2-(4-(N-cyclobutylsulfamoyl)phenyl)-N-(4-(1,1,1,3,3,3-hexafluoro-2-hydroxypropan-2-yl)phenyl)acetamide

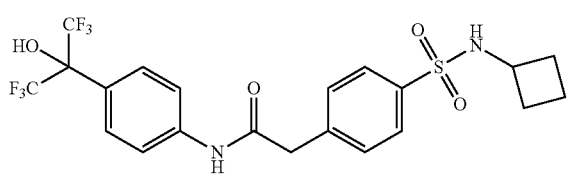 [SMILES: O=C(Cc1ccc(S(=O)(=O)NC2CCC2)cc1)Nc1ccc(C(O)(C(F)(F)F)C(F)(F)F)cc1]

MS(ES⁺) m/z 511.1 [M+H]⁺.

26: 2-(4-(N-cyclopropylsulfamoyl)phenyl)-N-(3-fluoro-4-(1,1,1,3,3,3-hexafluoro-2-hydroxypropan-2-yl)-2-methylphenyl)acetamide

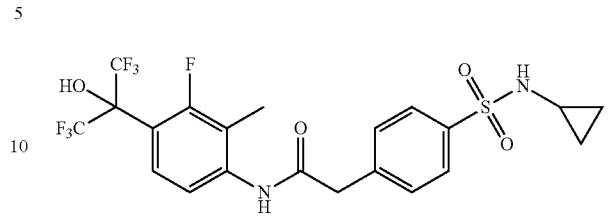

MS(ES⁺) m/z 529.2 [M+H]⁺.

27: N-(4-(1,1,1,3,3,3-hexafluoro-2-hydroxypropan-2-yl)phenyl)-2-(4-(isobutylsulfonyl)phenyl)acetamide

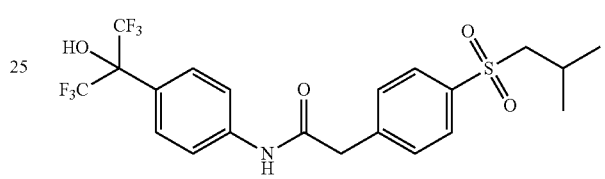

MS(ES⁺) m/z 498.1 [M+H]⁺.

Examples 28-41

28: 2-(4-(ethylsulfonyl)phenyl)-N-(2-fluoro-4-(1,1,1,3,3,3-hexafluoro-2-hydroxypropan-2-yl)phenyl)acetamide

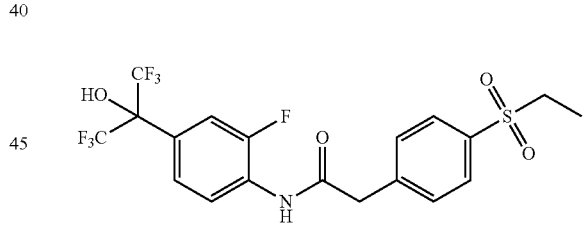

To a solution of 2-(4-amino-3-fluorophenyl)-1,1,1,3,3,3-hexafluoropropan-2-ol, (III-12, 50 mg), 2-(4-(ethanesulfonyl)phenyl)acetic acid, II-3 (41.7 mg) and DMAP (4.9 mg) in $CH_2Cl_2$ (2 ml) was added drop wise at 0° C. a solution of DCC (45.4 mg) in $CH_2Cl_2$ (2 ml). After stirring for 17 hours at room temperature, the reaction mixture was filtered and the solvent was removed under reduced pressure. The residue was purified on $SiO_2$, using 20% ethyl acetate in heptane as the eluent, to give the title compound 2-(4-(ethylsulfonyl)phenyl)-N-(2-fluoro-4-(1,1,3,3,3-hexafluoro-2-hydroxypropan-2-yl) phenyl)acetamide (62 mg) as a white solid. MS(ES⁺) m/z 488 [M+H]⁺.

¹H NMR(500 MHz, DMSO-d6): δ 10.30 (s, 1H), 8.91 (s, 1H), 8.11 (dd, 1H), 7.86 (d, 2H), 7.62 (d, 2H), 7.46-7.52 (m, 2H), 3.94 (s, 2H), 3.28 (q, 2H), 1.11 (t, 3H).

Following a procedure analogous to that described for example 28, the following compounds were prepared.

29: 2-(4-(ethylsulfonyl)phenyl)-N-(4-(1,1,1,3,3,3-hexafluoro-2-hydroxypropan-2-yl)-3-methylphenyl)acetamide

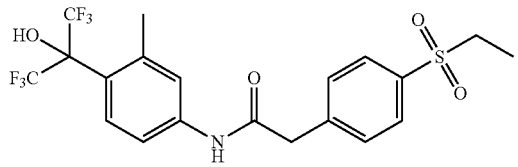 [SMILES: CCS(=O)(=O)c1ccc(CC(=O)Nc2ccc(C(O)(C(F)(F)F)C(F)(F)F)c(C)c2)cc1]

MS(ES+) m/z 484.2 [M+H]+.

30: 2-(4-(ethylsulfonyl)phenyl)-N-(3-fluoro-4-(1,1,1,3,3,3-hexafluoro-2-hydroxypropan-2-yl)phenyl)acetamide

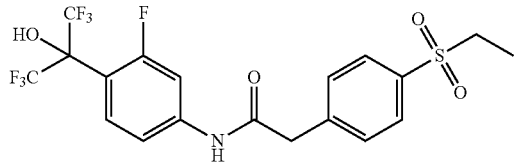 [SMILES: CCS(=O)(=O)c1ccc(CC(=O)Nc2ccc(C(O)(C(F)(F)F)C(F)(F)F)c(F)c2)cc1]

MS(ES+) m/z 488.2 [M+H]+.

31: 2-(4-(ethylsulfonyl)phenyl)-N-(4-(1,1,1,3,3,3-hexafluoro-2-hydroxypropan-2-yl)-2-methylphenyl)acetamide

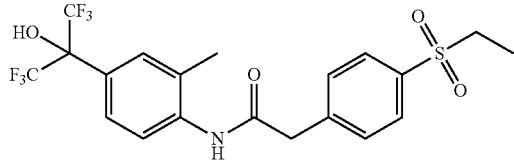 [SMILES: CCS(=O)(=O)c1ccc(CC(=O)Nc2ccc(C(O)(C(F)(F)F)C(F)(F)F)cc2C)cc1]

MS(ES+) m/z 484.2 [M+H]+.

32: 2-(4-(N-cyclopropylsulfamoyl)phenyl)-N-(4-(1,1,1,3,3,3-hexafluoro-2-hydroxypropan-2-yl)-3-methylphenyl)acetamide

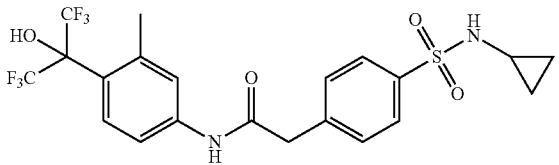 [SMILES: Cc1cc(NC(=O)Cc2ccc(S(=O)(=O)NC3CC3)cc2)ccc1C(O)(C(F)(F)F)C(F)(F)F]

MS(ES+) m/z 511.2 [M+H]+.

33: 2-(4-(N-cyclopropylsulfamoyl)phenyl)-N-(3-fluoro-4-(1,1,1,3,3,3-hexafluoro-2-hydroxypropan-2-yl)phenyl)acetamide

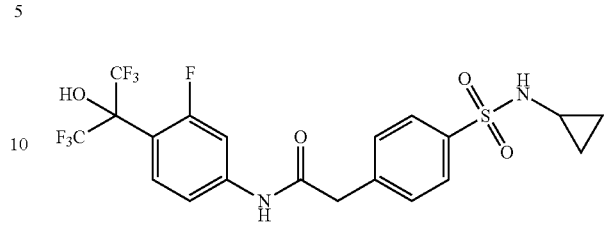

MS(ES+) m/z 515.2 [M+H]+.

34: 2-(4-(N-cyclopropylsulfamoyl)phenyl)-N-(4-(1,1,1,3,3,3-hexafluoro-2-hydroxypropan-2-yl)-2-methylphenyl)acetamide

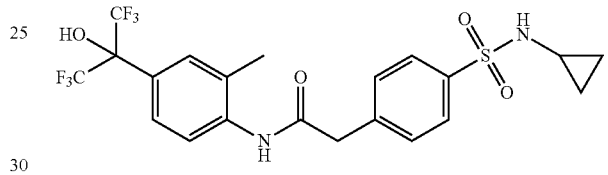

MS(ES+) m/z 511.1 [M+H]+.

35: 2-(4-(N-cyclopropylsulfamoyl)phenyl)-N-(2-fluoro-4-(1,1,1,3,3,3-hexafluoro-2-hydroxypropan-2-yl)phenyl)acetamide

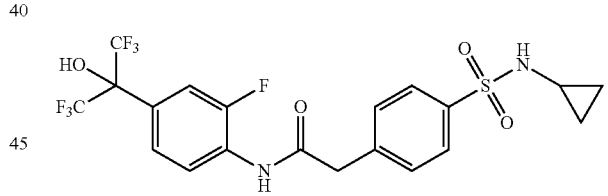

MS(ES+) m/z 515.2 [M+H]+.

36: 2-(3-(N-cyclopropylsulfamoyl)phenyl)-N-(4-(1,1,1,3,3,3-hexafluoro-2-hydroxypropan-2-yl)-3-methylphenyl)acetamide

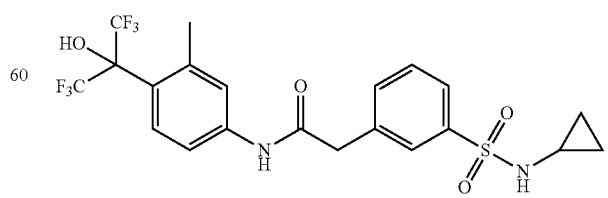

MS(ES+) m/z 511.2 [M+H]+.

37: 2-(4-((cyclopropylmethyl)sulfonyl)phenyl)-N-(4-(1,1,1,3,3,3-hexafluoro-2-hydroxypropan-2-yl)phenyl)acetamide

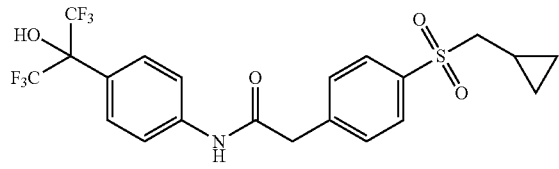 [SMILES: O=C(Cc1ccc(S(=O)(=O)CC2CC2)cc1)Nc1ccc(C(O)(C(F)(F)F)C(F)(F)F)cc1]

MS(ES$^+$) m/z 496.2 [M+H]$^+$.

38: 2-(3-(N-cyclopropylsulfamoyl)phenyl)-N-(3-fluoro-4-(1,1,1,3,3,3-hexafluoro-2-hydroxypropan-2-yl)phenyl)acetamide

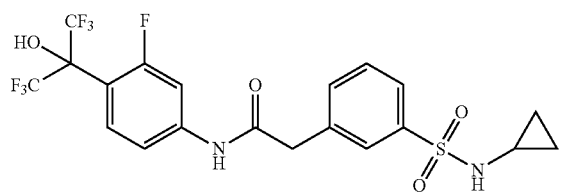 [SMILES: O=C(Cc1cccc(S(=O)(=O)NC2CC2)c1)Nc1ccc(C(O)(C(F)(F)F)C(F)(F)F)c(F)c1]

MS(ES$^+$) m/z 515.2 [M+H]$^+$.

39: 2-(3-(N-cyclopropylsulfamoyl)phenyl)-N-(4-(1,1,1,3,3,3-hexafluoro-2-hydroxypropan-2-yl)-2-methylphenyl)acetamide

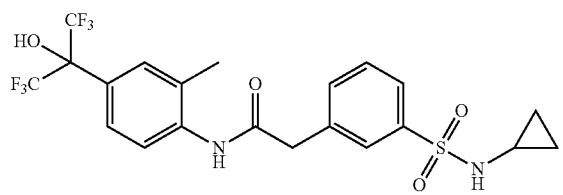 [SMILES: Cc1cc(C(O)(C(F)(F)F)C(F)(F)F)ccc1NC(=O)Cc1cccc(S(=O)(=O)NC2CC2)c1]

MS(ES$^+$) m/z 511.2 [M+H]$^+$.

40: 2-(3-(N-cyclopropylsulfamoyl)phenyl)-N-(2-fluoro-4-(1,1,1,3,3,3-hexafluoro-2-hydroxypropan-2-yl)phenyl)acetamide

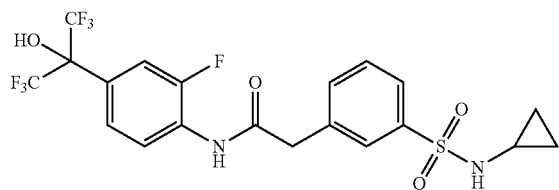 [SMILES: O=C(Cc1cccc(S(=O)(=O)NC2CC2)c1)Nc1ccc(C(O)(C(F)(F)F)C(F)(F)F)cc1F]

MS(ES$^+$) m/z 515.2 [M+H]$^+$.

41: 2-(3-(N-(cyclopropylmethyl)sulfamoyl)phenyl)-N-(4-(1,1,1,3,3,3-hexafluoro-2-hydroxypropan-2-yl)phenyl)acetamide

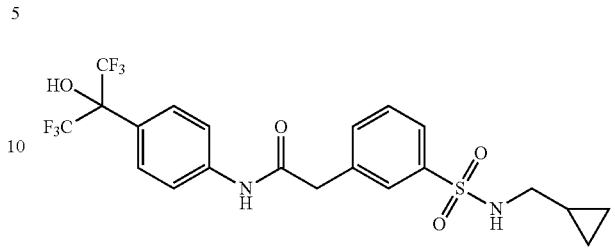

MS(ES$^+$) m/z 511.2 [M+H]$^+$.

Examples 42-111

Following a procedure analogous to that described for example 28, using EDCI instead of DCC, the following compounds were prepared.

42: 2-(4-(ethylsulfonyl)-3-fluorophenyl)-N-(4-(1,1,1,3,3,3-hexafluoro-2-hydroxypropan-2-yl)phenyl)acetamide

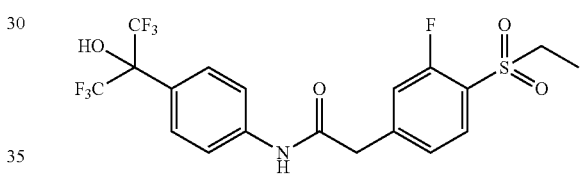

MS(ES$^+$) m/z 488.2 [M+H]$^+$.

43: 2-(4-((cyclopropylmethyl)sulfonyl)phenyl)-N-(4-(1,1,1,3,3,3-hexafluoro-2-hydroxypropan-2-yl)-2-methylphenyl)acetamide

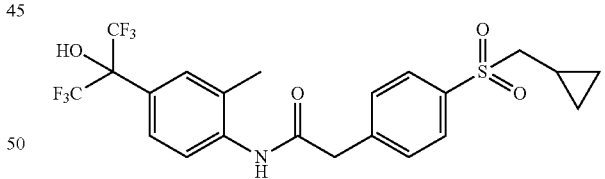

MS(ES$^+$) m/z 510.2 [M+H]$^+$.

44: 2-(4-((cyclopropylmethyl)sulfonyl)phenyl)-N-(4-(1,1,1,3,3,3-hexafluoro-2-hydroxypropan-2-yl)-3-methylphenyl)acetamide

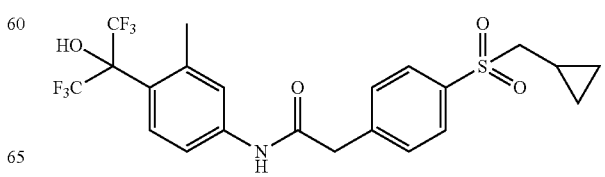

MS(ES$^+$) m/z 510.2 [M+H]$^+$.

45: 2-(4-((cyclopropylmethyl)sulfonyl)phenyl)-N-(3-fluoro-4-(1,1,1,3,3,3-hexafluoro-2-hydroxypropan-2-yl)phenyl)acetamide

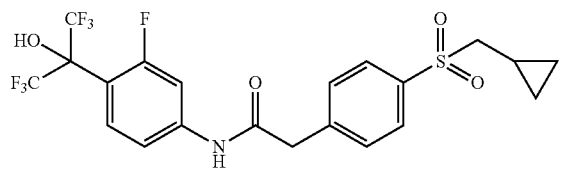

MS(ES$^+$) m/z 514.2 [M+H]$^+$.

46: 2-(4-((cyclopropylmethyl)sulfonyl)phenyl)-N-(2-fluoro-4-(1,1,1,3,3,3-hexafluoro-2-hydroxypropan-2-yl)phenyl)acetamide

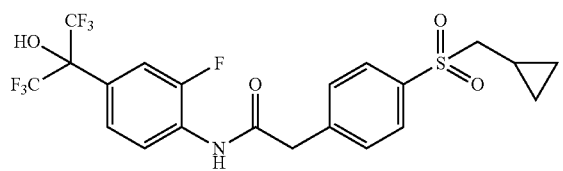 [SMILES: O=C(Cc1ccc(S(=O)(=O)CC2CC2)cc1)Nc1ccc(C(O)(C(F)(F)F)C(F)(F)F)cc1F]

MS(ES$^+$) m/z 514.2 [M+H]$^+$.

47: 2-(4-(ethylsulfonyl)phenyl)-N-(4-(1,1,1,3,3,3-hexafluoro-2-methoxypropan-2-yl)phenyl)acetamide

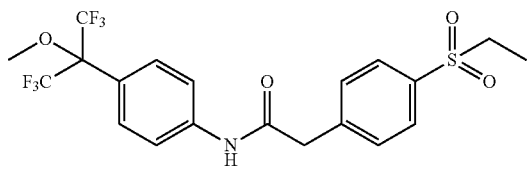 [SMILES: CCS(=O)(=O)c1ccc(CC(=O)Nc2ccc(C(OC)(C(F)(F)F)C(F)(F)F)cc2)cc1]

MS(ES$^+$) m/z 484.1 [M+H]$^+$.

48: N-(4-(2-ethoxy-1,1,1,3,3,3-hexafluoropropan-2-yl)phenyl)-2-(4-(ethylsulfonyl)phenyl)acetamide

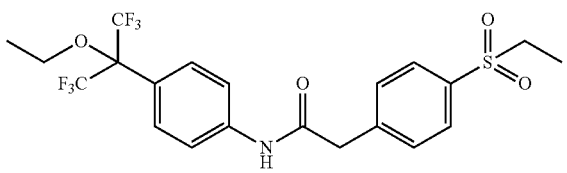 [SMILES: CCOC(c1ccc(NC(=O)Cc2ccc(S(=O)(=O)CC)cc2)cc1)(C(F)(F)F)C(F)(F)F]

MS(ES$^+$) m/z 498.2 [M+H]$^+$.

49: 2-(4-(ethylsulfonyl)phenyl)-N-(4-(1,1,1,3,3,3-hexafluoro-2-propoxypropan-2-yl)phenyl)acetamide

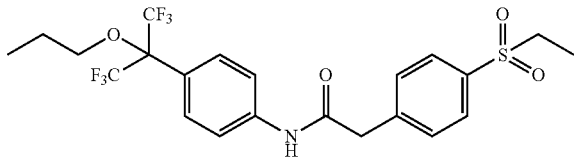 [SMILES: CCCOC(c1ccc(NC(=O)Cc2ccc(S(=O)(=O)CC)cc2)cc1)(C(F)(F)F)C(F)(F)F]

MS(ES$^+$) m/z 512.2 [M+H]$^+$.

50: N-(4-(2-(benzyloxy)-1,1,1,3,3,3-hexafluoropropan-2-yl)phenyl)-2-(4-(ethylsulfonyl)phenyl)acetamide

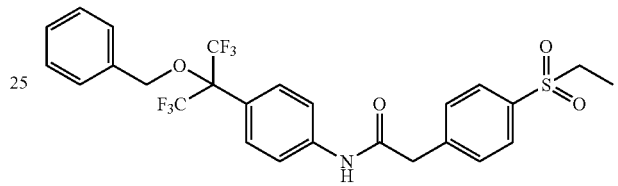

MS(ES$^+$) m/z 560.2 [M+H]$^+$.

51: 2-(4-((cyclopropylmethyl)sulfonyl)phenyl)-N-(4-(1,1,1,3,3,3-hexafluoro-2-isopropoxypropan-2-yl)phenyl)acetamide

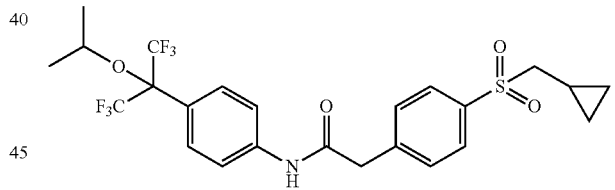

MS(ES$^+$) m/z 538.2 [M+H]$^+$.

52: N-(4-(2-butoxy-1,1,1,3,3,3-hexafluoropropan-2-yl)phenyl)-2-(4-((cyclopropylmethyl)sulfonyl)phenyl)acetamide

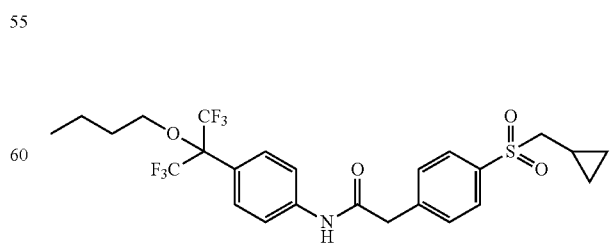

MS(ES$^+$) m/z 552.2 [M+H]$^+$.

53: 2-(4-((cyclopropylmethyl)sulfonyl)phenyl)-N-(4-(2-ethoxy-1,1,1,3,3,3-hexafluoropropan-2-yl)phenyl)acetamide

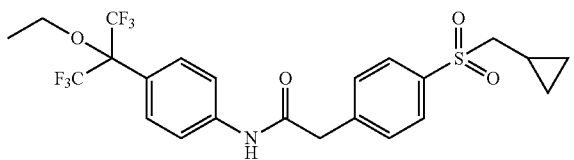 [SMILES: CCOC(c1ccc(NC(=O)Cc2ccc(S(=O)(=O)CC3CC3)cc2)cc1)(C(F)(F)F)C(F)(F)F]

MS(ES$^+$) m/z 524.2 [M+H]$^+$.

54: 2-(4-((cyclopropylmethyl)sulfonyl)phenyl)-N-(4-(1,1,1,3,3,3-hexafluoro-2-methoxypropan-2-yl)phenyl)acetamide

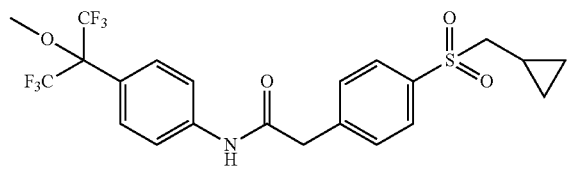 [SMILES: COC(c1ccc(NC(=O)Cc2ccc(S(=O)(=O)CC3CC3)cc2)cc1)(C(F)(F)F)C(F)(F)F]

MS(ES$^+$) m/z 510.2 [M+H]$^+$.

55: 2-(4-((cyclopropylmethyl)sulfonyl)phenyl)-N-(4-(1,1,1,3,3,3-hexafluoro-2-hydroxypropan-2-yl)-2-methoxyphenyl)acetamide

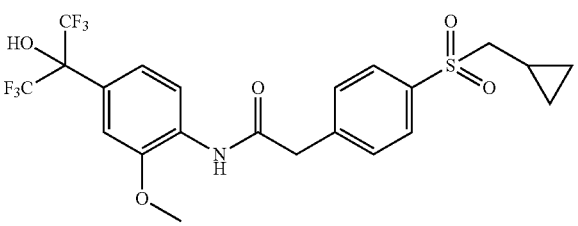 [SMILES: COc1cc(C(O)(C(F)(F)F)C(F)(F)F)ccc1NC(=O)Cc1ccc(S(=O)(=O)CC2CC2)cc1]

MS(ES$^+$) m/z 526.2 [M+H]$^+$.

56: 2-(4-((cyclopropylmethyl)sulfonyl)phenyl)-N-(4-(1,1,1,3,3,3-hexafluoro-2-hydroxypropan-2-yl)-3-methoxyphenyl)acetamide

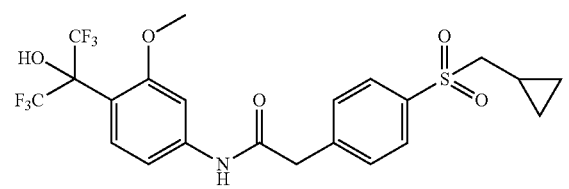 [SMILES: COc1cc(NC(=O)Cc2ccc(S(=O)(=O)CC3CC3)cc2)ccc1C(O)(C(F)(F)F)C(F)(F)F]

MS(ES$^+$) m/z 526.2 [M+H]$^+$,

57: N-(2-amino-4-(1,1,1,3,3,3-hexafluoro-2-hydroxypropan-2-yl)phenyl)-2-(4-((cyclopropylmethyl)sulfonyl)phenyl)acetamide

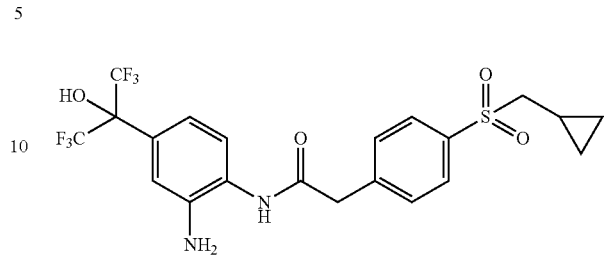

MS(ES$^+$) m/z 511.2 [M+H]$^+$.

58: N-(4-(2-(2-cyclopropylethoxy)-1,1,1,3,3,3-hexafluoropropan-2-yl)phenyl)-2-(4-((cyclopropylmethyl)sulfonyl)phenyl)acetamide

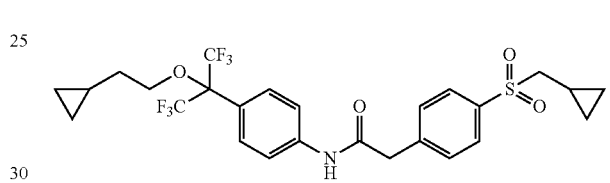

MS(ES$^+$) m/z 564.2 [M+H]$^+$.

59: N-(4-(2-(benzyloxy)-1,1,1,3,3,3-hexafluoropropan-2-yl)phenyl)-2-(4-((cyclopropylmethyl)sulfonyl)phenyl)acetamide

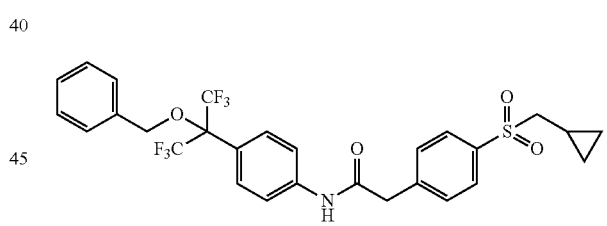

MS(ES$^+$) m/z 586.2 [M+H]$^+$.

60: 2-(4-((cyclopropylmethyl)sulfonyl)phenyl)-N-(4-(1,1,1,3,3,3-hexafluoro-2-propoxypropan-2-yl)phenyl)acetamide

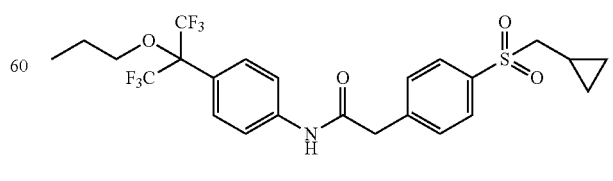

MS(ES$^+$) m/z 538.2 [M+H]$^+$.

61: 2-(4-(N-cyclopropylsulfamoyl)phenyl)-N-(4-(1,1,1,3,3,3-hexafluoro-2-propoxypropan-2-yl)phenyl)acetamide

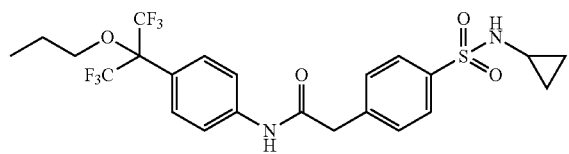 [SMILES: CCCOC(c1ccc(NC(=O)Cc2ccc(S(=O)(=O)NC3CC3)cc2)cc1)(C(F)(F)F)C(F)(F)F]

MS(ES⁺) m/z 539.2 [M+H]⁺.

62: N-(3-chloro-4-(1,1,1,3,3,3-hexafluoro-2-hydroxypropan-2-yl)phenyl)-2-(4-((cyclopropylmethyl)sulfonyl)phenyl)acetamide

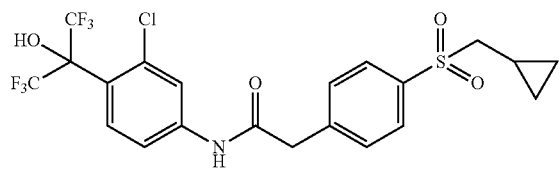

MS(ES⁺) m/z 530.2 [M+H]⁺.

63: 2-(4-(ethylsulfonyl)phenyl)-N-(4-(1,1,1-trifluoro-2-hydroxypentan-2-yl)phenyl)acetamide

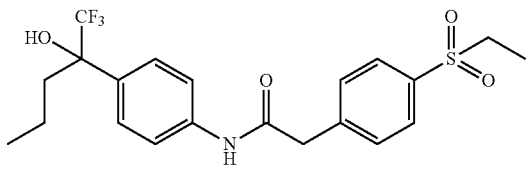 [SMILES: CCCC(O)(c1ccc(NC(=O)Cc2ccc(S(=O)(=O)CC)cc2)cc1)C(F)(F)F]

MS(ES⁺) m/z 444.2 [M+H]⁺.

64: 2-(4-((cyclopropylmethyl)sulfonyl)phenyl)-N-(4-(1,1,1-trifluoro-2-hydroxyhexan-2-yl)phenyl)acetamide

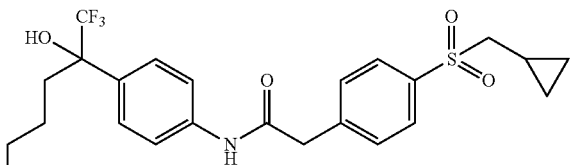

MS(ES⁺) m/z 484.2 [M+H]⁺.

65: 2-(4-(ethylsulfonyl)phenyl)-N-(4-(1,1,1-trifluoro-2-hydroxy-3-methylbutan-2-yl)phenyl)acetamide

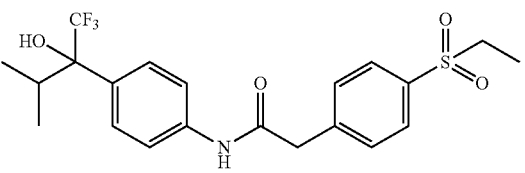 [SMILES: CCS(=O)(=O)c1ccc(CC(=O)Nc2ccc(C(O)(C(C)C)C(F)(F)F)cc2)cc1]

MS(ES⁺) m/z 444.2 [M+H]⁺.

66: 2-(4-(ethylsulfonyl)phenyl)-N-(4-(1,1,1-trifluoro-2-hydroxy-4-methylpentan-2-yl)phenyl)acetamide

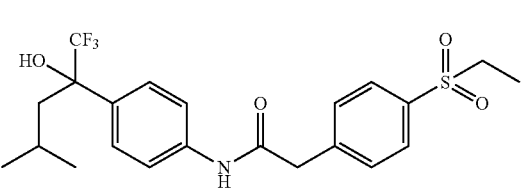 [SMILES: CCS(=O)(=O)c1ccc(CC(=O)Nc2ccc(C(O)(CC(C)C)C(F)(F)F)cc2)cc1]

MS(ES⁺) m/z 458.2 [M+H]⁺.

67: N-(4-(1-cyclopropyl-2,2,2-trifluoro-1-hydroxyethyl)phenyl)-2-(4-((cyclopropylmethyl)sulfonyl)phenyl)acetamide

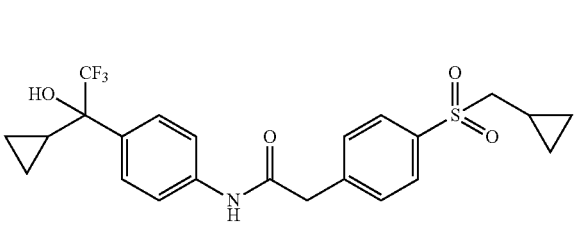 [SMILES: O=C(Cc1ccc(S(=O)(=O)CC2CC2)cc1)Nc1ccc(C(O)(C2CC2)C(F)(F)F)cc1]

MS(ES⁺) m/z 468.2 [M+H]⁺.

68: N-(4-(3-cyclopentyl-1,1,1-trifluoro-2-hydroxypropan-2-yl)phenyl)-2-(4-((cyclopropylmethyl)sulfonyl)phenyl)acetamide

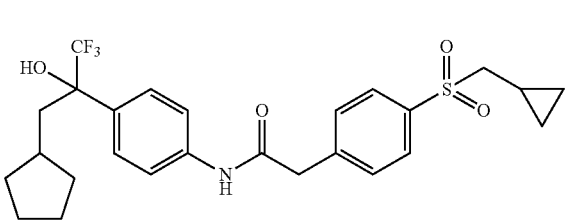 [SMILES: O=C(Cc1ccc(S(=O)(=O)CC2CC2)cc1)Nc1ccc(C(O)(CC2CCCC2)C(F)(F)F)cc1]

MS(ES⁺) m/z 510.2 [M+H]⁺.

69: N-(4-(3-cyclohexyl-1,1,1-trifluoro-2-hydroxy-propan-2-yl)phenyl)-2-(4-((cyclopropylmethyl)sulfonyl)phenyl)acetamide

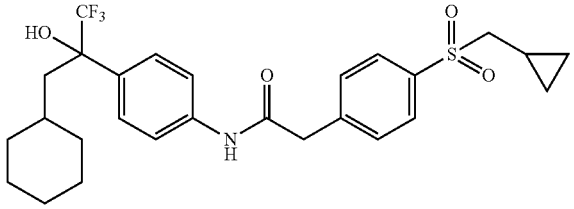 [SMILES: O=C(Cc1ccc(S(=O)(=O)CC2CC2)cc1)Nc1ccc(C(O)(CC2CCCCC2)C(F)(F)F)cc1]

MS(ES$^+$) m/z 524.2 [M+H]$^+$.

70: 2-(4-((cyclopropylmethyl)sulfonyl)phenyl)-N-(4-(2,2,2-trifluoro-1-hydroxyethyl)phenyl)acetamide

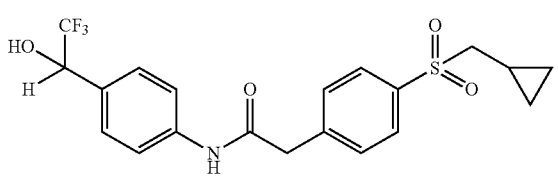 [SMILES: O=C(Cc1ccc(S(=O)(=O)CC2CC2)cc1)Nc1ccc(C(O)C(F)(F)F)cc1]

MS(ES$^+$) m/z 428.2 [M+H]$^+$.

71: 2-(4-((cyclopropylmethyl)sulfonyl)phenyl)-N-(4-(1,1,1-trifluoro-2-hydroxypropan-2-yl)phenyl)acetamide

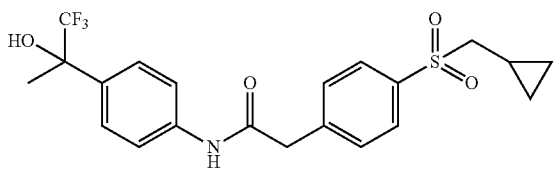 [SMILES: CC(O)(c1ccc(NC(=O)Cc2ccc(S(=O)(=O)CC3CC3)cc2)cc1)C(F)(F)F]

MS(ES$^+$) m/z 473.2 [M+H]$^+$.

72: 2-(4-(ethylsulfonyl)phenyl)-N-(4-(1,1,1-trifluoro-2-hydroxyhexan-2-yl)phenyl)acetamide

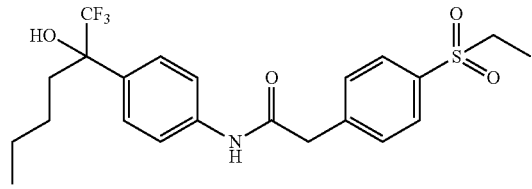 [SMILES: CCCCC(O)(c1ccc(NC(=O)Cc2ccc(S(=O)(=O)CC)cc2)cc1)C(F)(F)F]

MS(ES$^+$) m/z 458.2 [M+H]$^+$.

73: N-(4-(1-cyclopropyl-2,2,2-trifluoro-1-hydroxyethyl)phenyl)-2-(4-(ethylsulfonyl)phenyl)acetamide

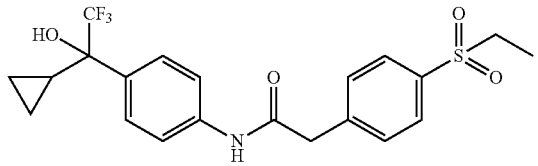 [SMILES: CCS(=O)(=O)c1ccc(CC(=O)Nc2ccc(C(O)(C3CC3)C(F)(F)F)cc2)cc1]

MS(ES$^+$) m/z 442.2 [M+H]$^+$.

74: N-(4-(3-cyclohexyl-1,1,1-trifluoro-2-hydroxy-propan-2-yl)phenyl)-2-(4-(ethylsulfonyl)phenyl)acetamide

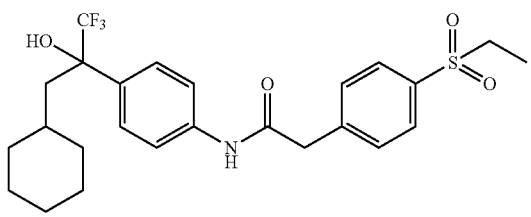 [SMILES: CCS(=O)(=O)c1ccc(CC(=O)Nc2ccc(C(O)(CC3CCCCC3)C(F)(F)F)cc2)cc1]

MS(ES$^+$) m/z 498.2 [M+H]$^+$.

75: N-(4-(1-cyclopentyl-2,2,2-trifluoro-1-hydroxyethyl)phenyl)-2-(4-((cyclopropylmethyl)sulfonyl)phenyl)acetamide

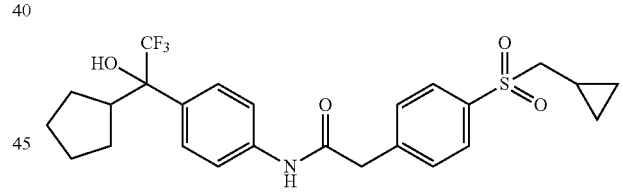

MS(ES$^+$) m/z 496.2 [M+H]$^+$.

76: 2-(4-(N-cyclopropylsulfamoyl)phenyl)-N-(4-(1,1,1-trifluoro-2-hydroxy-4-methylpentan-2-yl)phenyl)acetamide

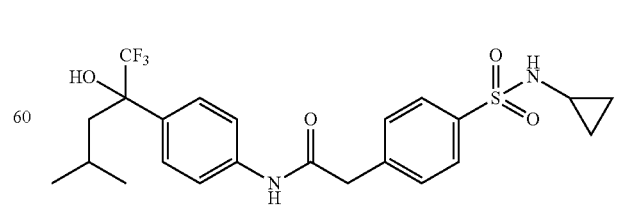

MS(ES$^+$) m/z 485.2 [M+H]$^+$.

77: 2-(3-(N-cyclopropylsulfamoyl)phenyl)-N-(4-(1,1,1-trifluoro-2-hydroxy-4-methylpentan-2-yl)phenyl)acetamide

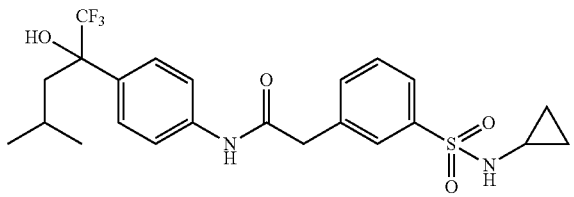 [SMILES: CC(C)CC(O)(c1ccc(NC(=O)Cc2cccc(S(=O)(=O)NC3CC3)c2)cc1)C(F)(F)F]

MS(ES⁺) m/z 485.2 [M+H]⁺.

78: 2-(4-(N-cyclopropylsulfamoyl)phenyl)-N-(4-(1,1,1-trifluoro-2-hydroxypropan-2-yl)phenyl)acetamide

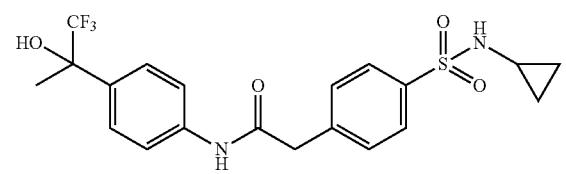 [SMILES: CC(O)(c1ccc(NC(=O)Cc2ccc(S(=O)(=O)NC3CC3)cc2)cc1)C(F)(F)F]

MS(ES⁺) m/z 443.2 [M+H]⁺.

79: 2-(4-(N-cyclopropylsulfamoyl)phenyl)-N-(4-(1,1,1-trifluoro-2-hydroxybutan-2-yl)phenyl)acetamide

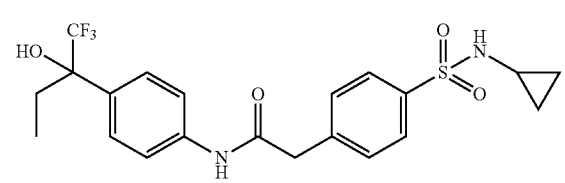 [SMILES: CCC(O)(c1ccc(NC(=O)Cc2ccc(S(=O)(=O)NC3CC3)cc2)cc1)C(F)(F)F]

MS(ES⁺) m/z 457.2 [M+H]⁺.

80: 2-(4-(N-cyclopropylsulfamoyl)phenyl)-N-(4-(1,1,1-trifluoro-2-hydroxypentan-2-yl)phenyl)acetamide

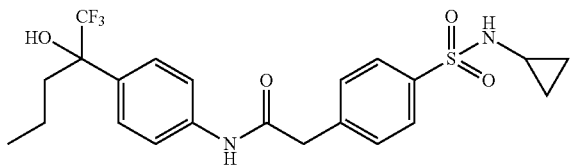 [SMILES: CCCC(O)(c1ccc(NC(=O)Cc2ccc(S(=O)(=O)NC3CC3)cc2)cc1)C(F)(F)F]

MS(ES⁺) m/z 471.2 [M+H]⁺.

81: 2-(3-(N-cyclopropylsulfamoyl)phenyl)-N-(4-(1,1,1-trifluoro-2-hydroxypentan-2-yl)phenyl)acetamide

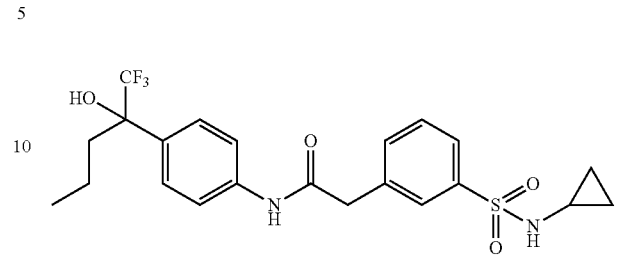

MS(ES⁺) m/z 471.2 [M+H]⁺.

82: 2-(4-((cyclopropylmethyl)sulfonyl)phenyl)-N-(4-(1,1,1-trifluoro-2-hydroxy-4,4-dimethylpentan-2-yl)phenyl)acetamide

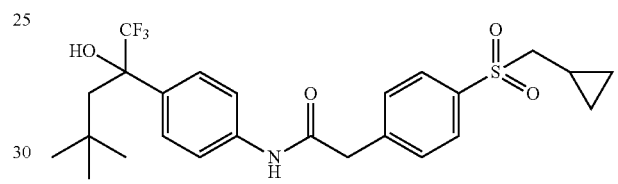

MS(ES⁺) m/z 498.2 [M+H]⁺.

83: 2-(4-((cyclopropylmethyl)sulfonyl)phenyl)-N-(4-(1,1,1-trifluoro-2-hydroxybutan-2-yl)phenyl)acetamide

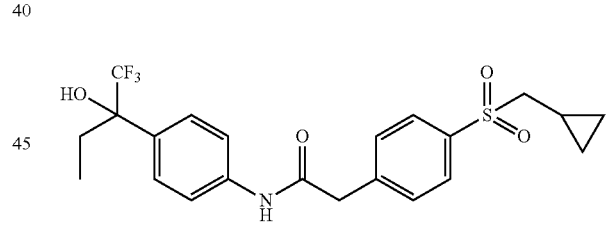

MS(ES⁺) m/z 456.2 [M+H]⁺.

84: N-(3-chloro-4-(1,1,1,3,3,3-hexafluoro-2-hydroxypropan-2-yl)phenyl)-2-(4-(ethylsulfonyl)phenyl)acetamide

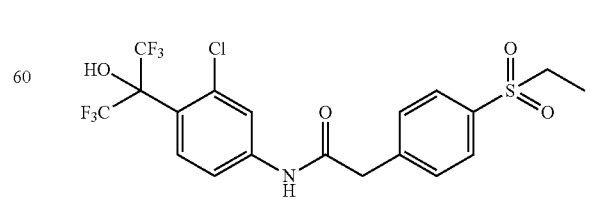

MS(ES⁺) m/z 504.2 [M+H]⁺.

85: N-(4-(1-cyclopentyl-2,2,2-trifluoro-1-hydroxy-ethyl)phenyl)-2-(4-(ethylsulfonyl)phenyl)acetamide

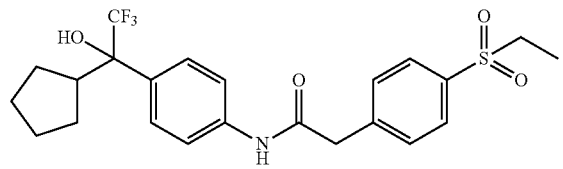 [SMILES: CCS(=O)(=O)c1ccc(CC(=O)Nc2ccc(C(O)(C3CCCC3)C(F)(F)F)cc2)cc1]

MS(ES⁺) m/z 470.2 [M+H]⁺.

86: N-(4-(3-cyclopentyl-1,1,1-trifluoro-2-hydroxy-propan-2-yl)phenyl)-2-(4-(ethylsulfonyl)phenyl) acetamide

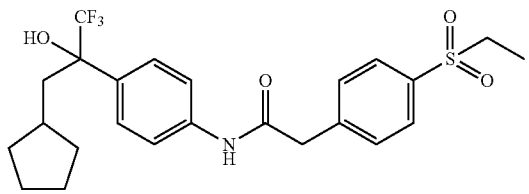 [SMILES: CCS(=O)(=O)c1ccc(CC(=O)Nc2ccc(C(O)(CC3CCCC3)C(F)(F)F)cc2)cc1]

MS(ES⁺) m/z 484.2 [M+H]⁺.

87: 2-(4-cyclopropylmethanesulfonylphenyl)-N-[4-(1,1,1-trifluoro-2-hydroxy-3-phenylpropan-2-yl) phenyl]acetamide

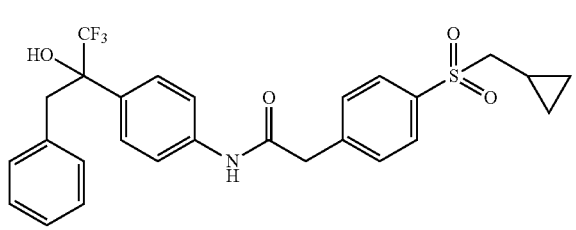 [SMILES: O=C(Cc1ccc(S(=O)(=O)CC2CC2)cc1)Nc1ccc(C(O)(Cc2ccccc2)C(F)(F)F)cc1]

MS(ES⁺) m/z 518.2 [M+H]⁺.

88: 2-(4-((cyclopropylmethyl)sulfonyl)phenyl)-N-(4-(2,2,2-trifluoro-1-hydroxy-1-phenylethyl)phenyl) acetamide

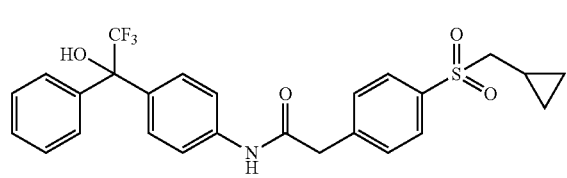 [SMILES: O=C(Cc1ccc(S(=O)(=O)CC2CC2)cc1)Nc1ccc(C(O)(c2ccccc2)C(F)(F)F)cc1]

MS(ES⁺) m/z 504.2 [M+H]⁺.

89: N-(3-chloro-4-(1,1,1,3,3,3-hexafluoro-2-hydroxypropan-2-yl)phenyl)-2-(4-(N-cyclopropylsulfamoyl)phenyl)acetamide

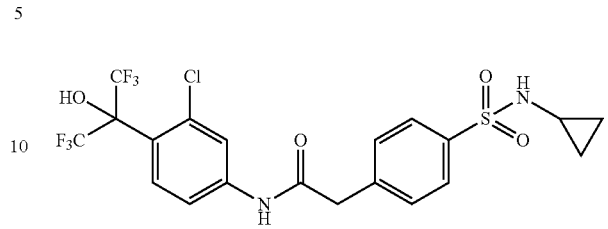

MS(ES⁺) m/z 531.2 [M+H]⁺.

90: N-(4-(1-cyclopentyl-2,2,2-trifluoro-1-hydroxy-ethyl)phenyl)-2-(4-(N-cyclopropylsulfamoyl)phenyl) acetamide

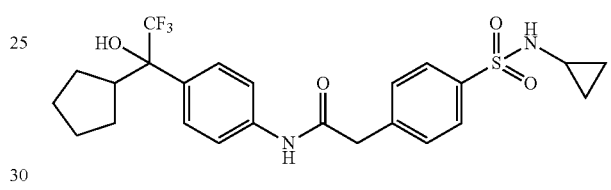

MS(ES⁺) m/z 597.2 [M+H]⁺.

91: N-(3-chloro-4-(1,1,1,3,3,3-hexafluoro-2-hydroxypropan-2-yl)phenyl)-2-(3-(N-cyclopropylsulfamoyl)phenyl)acetamide

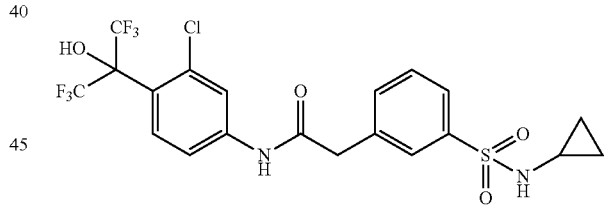

MS(ES⁺) m/z 531.2 [M+H]⁺.

92: N-(4-(1-cyclopentyl-2,2,2-trifluoro-1-hydroxy-ethyl)phenyl)-2-(3-(N-cyclopropylsulfamoyl)phenyl) acetamie

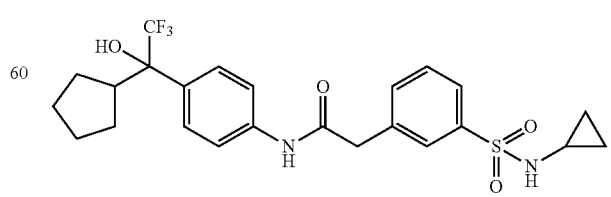

MS(ES⁺) m/z 497.2 [M+H]⁺.

93: 2-(4-((cyclopropylmethyl)sulfonyl)-2-methyl-phenyl)-N-(4-(1,1,1,3,3,3-hexafluoro-2-hydroxypropan-2-yl)phenyl)acetamide

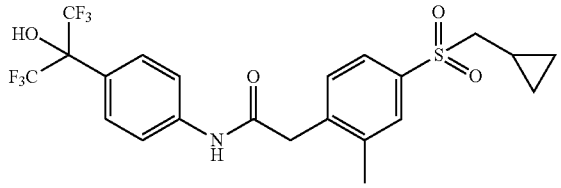 [SMILES: Cc1cc(S(=O)(=O)CC2CC2)ccc1CC(=O)Nc1ccc(C(O)(C(F)(F)F)C(F)(F)F)cc1]

MS(ES$^+$) m/z 510.2 [M+H]$^+$.

94: 2-(4-(N-cyclopropylsulfamoyl)phenyl)-N-(4-(1,1,1-trifluoro-2-hydroxy-4,4-dimethylpentan-2-yl)phenyl)acetamide

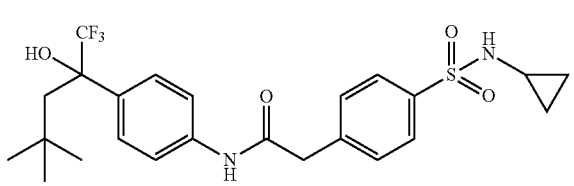 [SMILES: CC(C)(C)CC(O)(c1ccc(NC(=O)Cc2ccc(S(=O)(=O)NC3CC3)cc2)cc1)C(F)(F)F]

MS(ES$^+$) m/z 499.2 [M+H]$^+$.

95: 2-(4-(N-cyclopropylsulfamoyl)phenyl)-N-(4-(1,1,1-trifluoro-2-hydroxy-3-methylbutan-2-yl)phenyl)acetamide

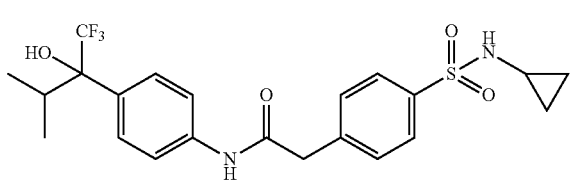 [SMILES: CC(C)C(O)(c1ccc(NC(=O)Cc2ccc(S(=O)(=O)NC3CC3)cc2)cc1)C(F)(F)F]

MS(ES$^+$) m/z 471.2 [M+H]$^+$.

96: 2-(4-(ethylsulfonyl)phenyl)-N-(4-(1,1,1-trifluoro-2-hydroxy-4,4-dimethylpentan-2-yl)phenyl)acetamide

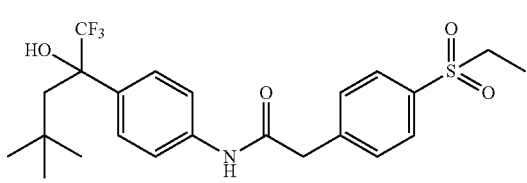 [SMILES: CCS(=O)(=O)c1ccc(CC(=O)Nc2ccc(C(O)(CC(C)(C)C)C(F)(F)F)cc2)cc1]

MS(ES$^+$) m/z 472.2 [M+H]$^+$.

97: 2-(4-(ethylsulfonyl)phenyl)-N-(4-(2,2,2-trifluoro-1-hydroxy-1-phenylethyl)phenyl)acetamide

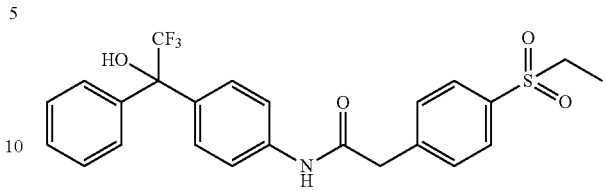

MS(ES$^+$) m/z 478.2 [M+H]$^+$.

98: N-(2-chloro-4-(1,1,1,3,3,3-hexafluoro-2-hydroxypropan-2-yl)phenyl)-2-(4-((cyclopropylmethyl)sulfonyl)phenyl)acetamide

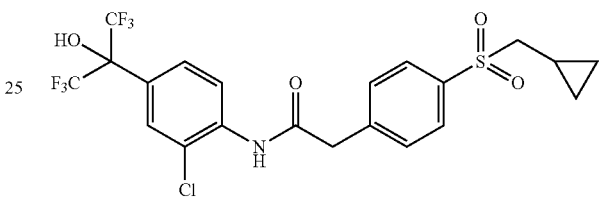

MS(ES$^+$) m/z 530.2 [M+H]$^+$.

99: N-(4-(3-cyclopentyl-1,1,1-trifluoro-2-hydroxypropan-2-yl)phenyl)-2-(4-(N-cyclopropylsulfamoyl)phenyl)acetamide

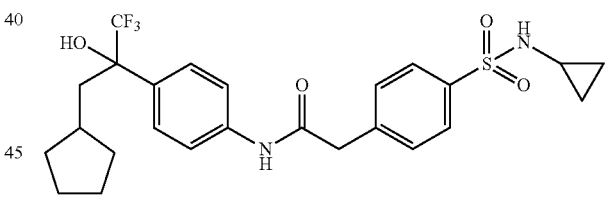

MS(ES$^+$) m/z 511.2 [M+H]$^+$.

100: N-(4-(3-cyclohexyl-1,1,1-trifluoro-2-hydroxypropan-2-yl)phenyl)-2-(4-(N-cyclopropylsulfamoyl)phenyl)acetamide

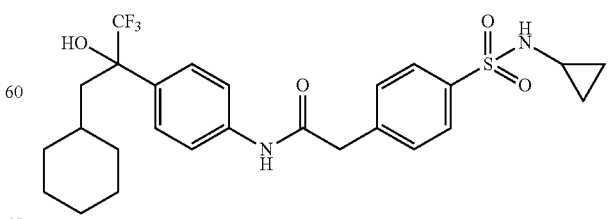

MS(ES$^+$) m/z 525.3 [M+H]$^+$.

101: 2-(4-(N-cyclopropylsulfamoyl)phenyl)-N-(4-(2,2,2-trifluoro-1-hydroxy-1-phenylethyl)phenyl)acetamide

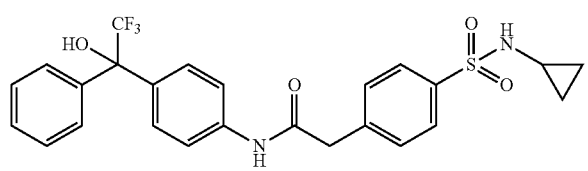 [SMILES: O=C(Cc1ccc(S(=O)(=O)NC2CC2)cc1)Nc1ccc(C(O)(c2ccccc2)C(F)(F)F)cc1]

MS(ES⁺) m/z 505.2 [M+H]⁺.

102: 2-(4-((cyclopropylmethyl)sulfonyl)phenyl)-N-(4-(1,1,1,3,3,3-hexafluoro-2-hydroxypropan-2-yl)phenyl)-2-oxoacetamide

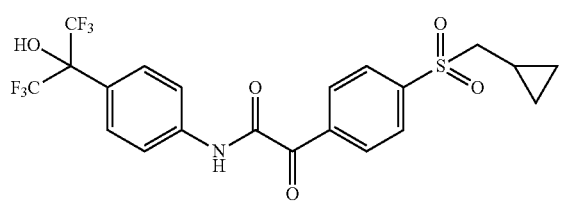 [SMILES: O=C(Nc1ccc(C(O)(C(F)(F)F)C(F)(F)F)cc1)C(=O)c1ccc(S(=O)(=O)CC2CC2)cc1]

MS(ES⁺) m/z 510.1 [M+H]⁺.

103: 2-(4-((cyclopropylmethyl)sulfonyl)phenyl)-N-(4-(2-hydroxypropan-2-yl)phenyl)acetamide

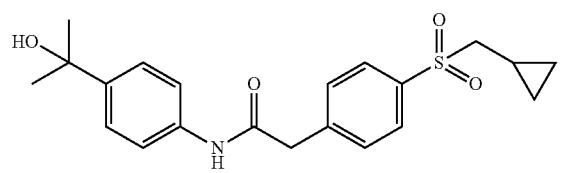 [SMILES: CC(C)(O)c1ccc(NC(=O)Cc2ccc(S(=O)(=O)CC3CC3)cc2)cc1]

MS(ES⁺) m/z 370.2 [(M-1 8)+H]⁺.
¹H NMR(500 MHz, DMSO-d6): δ 10.18 (s, 1H), 7.90-7.81 (m, 2H), 7.63-7.56 (m, 2H), 7.52-7.46 (m, 2H), 7.40-7.32 (m, 2H), 4.92 (s, 1H), 3.78 (s, 2H), 3.24 (d, 2H), 1.39 (s, 6H), 0.86-0.78 (m, 1H), 0.48-0.40 (m, 2H), 0.14-0.08 (m, 2H).

104: 2-(4-((cyclopropylmethyl)sulfonyl)phenyl)-N-(4-(1,1,1-trifluoro-2-hydroxy-5-methylhexan-2-yl)phenyl)acetamide

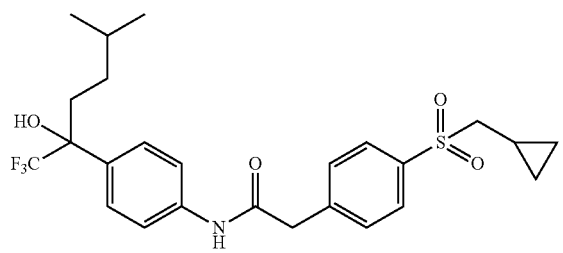 [SMILES: CC(C)CCC(O)(c1ccc(NC(=O)Cc2ccc(S(=O)(=O)CC3CC3)cc2)cc1)C(F)(F)F]

MS(ES⁺) m/z 498.3 [M+H]³⁰.

105: 2-(4-(N-cyclopropylsulfamoyl)phenyl)-N-(5-fluoro-4-(1,1,1,3,3,3-hexafluoro-2-hydroxypropan-2-yl)-2-methoxyphenyl)acetamide

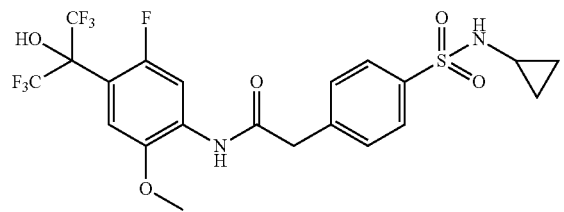 [SMILES: COc1cc(C(O)(C(F)(F)F)C(F)(F)F)c(F)cc1NC(=O)Cc1ccc(S(=O)(=O)NC2CC2)cc1]

MS(ES⁺) m/z 545.1 [M+H]⁺.

106: 2-(4-((cyclopropylmethyl)sulfonyl)phenyl)-N-(4-(dicyclopropyl(hydroxy)methyl)phenyl)acetamide

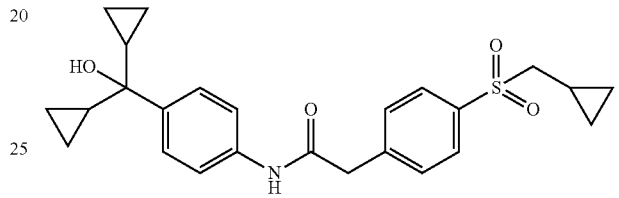

MS(ES⁺) m/z 422.2 [(M-18)+H]⁺.
¹H NMR(500 MHz, DMSO-d6): δ 10.18 (s, 1H), 7.90-7.80 (m, 2H), 7.65-7.55 (m, 2H), 7.50-7.40 (m, 4H), 4.32 (s, 1H), 3.78 (s, 2H), 3.24 (d, 2H), 1.20-1.09 (m, 2H), 0.86-0.78 (m, 1H), 0.55-0.47 (m, 2H), 0.46-0.41 (m, 2H), 0.38-0.30 (m, 2H), 0.29-0.21 (m, 2H), 0.20-0.14 (m, 2H), 0.13-0.09 (m, 2H).

107: 2-(4-((cyclopropylmethyl)sulfonyl)phenyl)-N-(5-(1,1,1,3,3,3-hexafluoro-2-hydroxypropan-2-yl)pyridin-2-yl)acetamide

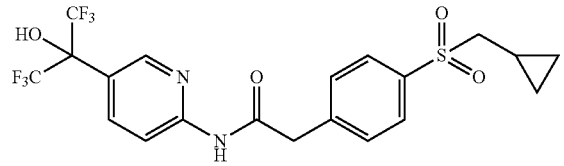

MS(ES⁺) m/z 497.2 [M+H]⁺.

108: 2-(4-((cyclopropylmethyl)sulfonyl)phenyl)-N-(4-(1,1,1-trifluoro-2-hydroxy-6-methylheptan-2-yl)phenyl)acetamide

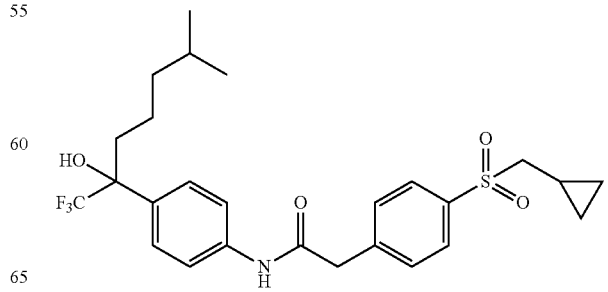

MS(ES⁺) m/z 512.3 [M+H]⁺.

109: 2-(4-((cyclopropylmethyl)sulfonyl)phenyl)-N-(4-(1,1,1,3,3,3-hexafluoro-2-hydroxypropan-2-yl)phenyl)propanamide

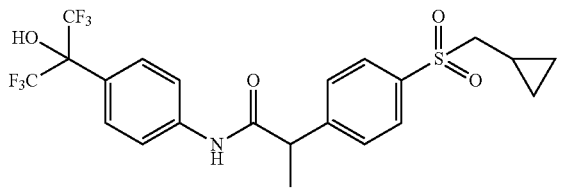 [SMILES: CC(C(=O)Nc1ccc(C(O)(C(F)(F)F)C(F)(F)F)cc1)c1ccc(S(=O)(=O)CC2CC2)cc1]

MS(ES$^+$) m/z 510.2 [M+H]$^+$.

110: 2-(4-((cyclopropylmethyl)sulfonyl)phenyl)-N-(6-(1,1,1,3,3,3-hexafluoro-2-hydroxypropan-2-yl)pyridin-3-yl)acetamide

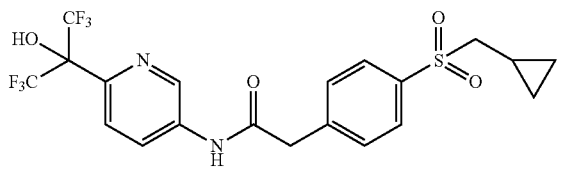 [SMILES: O=C(Cc1ccc(S(=O)(=O)CC2CC2)cc1)Nc1ccc(C(O)(C(F)(F)F)C(F)(F)F)nc1]

MS(ES$^+$) m/z 497.2 [M+H]$^+$.

111: 2-(4-(ethylsulfonyl)phenyl)-N-(6-(1,1,1,3,3,3-hexafluoro-2-hydroxypropan-2-yl)pyridin-3-yl)acetamide

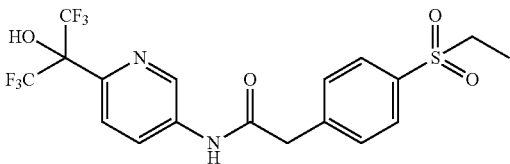 [SMILES: CCS(=O)(=O)c1ccc(CC(=O)Nc2ccc(C(O)(C(F)(F)F)C(F)(F)F)nc2)cc1]

MS(ES$^+$) m/z 471.2 [M+H]$^+$.

Examples 112 and 113

112: 2-(4-(ethylsulfonyl)phenyl)-N-(4-(1,1,1,3,3,3-hexafluoro-2-(2,2,2-trifluoroethoxy)propan-2-yl)phenyl)acetamide

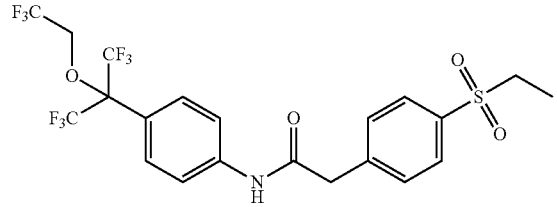 [SMILES: CCS(=O)(=O)c1ccc(CC(=O)Nc2ccc(C(OCC(F)(F)F)(C(F)(F)F)C(F)(F)F)cc2)cc1]

To a suspension of 2-(4-(ethylsulfonyl)phenyl)-N-(4-(1,1,1,3,3,3-hexafluoro-2-hydroxypropan-2-yl)phenyl)acetamide, (example 2) (20 mg) and K$_2$CO$_3$ (9 mg) in CH$_3$CN (1 ml) was added at room temperature 2,2,2-trifluoroethyl-trifluoro methanesulfonate (10 mg). After stirring for 17 hours at 80° C., the reaction mixture was cooled to room temperature and the solvent was removed under reduced pressure. The residue was purified on SiO$_2$, using 20% ethyl acetate in heptane as the eluent, to give the title compound 2-(4-(ethylsulfonyl)phenyl)-N-(4-(1,1,1,3,3,3-hexa fluoro-2-(2,2,2-trifluoro ethoxy) propan-2-yl)phenyl)acetamide (11 mg) as a white solid. MS(ES$^+$) m/z 552.2 [M+H]$^+$.

$^1$H NMR(500 MHz, DMSO-d6): δ 10.62 (s, 1H), 7.88-7.86 (m, 2H), 7.84-7.82 (m, 2H), 7.63-7.61 (m, 2H), 7.55-7.53 (m, 2H), 4.27 (q, 2H), 3.85 (s, 2H), 3.28 (q, 2H), 1.10 (t, 3H).

Following a procedure analogous to that described for example 111, the following compound was prepared.

113: 2-(4-((cyclopropylmethyl)sulfonyl)phenyl)-N-(4-(1,1,1,3,3,3-hexafluoro-2-(2,2,2-trifluoroethoxy)propan-2-yl)phenyl)acetamide

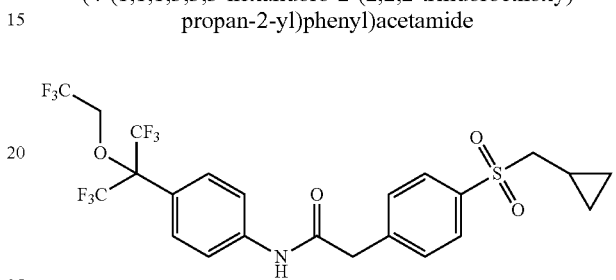

MS(ES$^+$) m/z 578.2 [M+H]$^+$.

114: 2-(4-((cyclopropylmethyl)sulfonyl)phenyl)-N-(4-(1,1,1,3,3,3-hexafluoro-2-hydroxypropan-2-yl)phenyl)-2-hydroxyacetamide

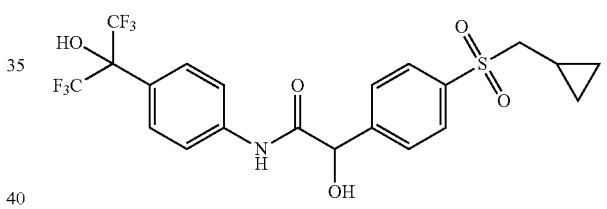

To a solution of 2-(4-((cyclopropylmethyl)sulfonyl)phenyl)-N-(4-(1,1,1,3,3,3-hexafluoro-2-hydroxypropan-2-yl)phenyl)-2-oxoacetamide, (example 101) (25 mg) in methanol (2 mL) was added NaBH4$_4$ (4 mg). After stirring for 1 hour at room temperature, the reaction mixture was concentrated under reduced pressure. To the residue was added an aqueous 1N HCl solution and the product was extracted into ethyl acetate. The combined organic layers were washed with water, brine, dried over magnesium sulfate and concentrated under reduced pressure. The residue was purified on reversed phase semi-prep. HPLC, using 20% to 80% CH$_3$CN in water, as the eluent, to give the title compound 2-(4-((cyclopropylmethyl)sulfonyl)phenyl)-N-(4-(1,1,1,3,3,3-hexafluoro-2-hydroxypropan-2-yl)phenyl)-2-hydroxyacetamide (6 mg) as a white solid. MS(ES$^+$) m/z 512.1 [M+H]$^+$.

Example 115

RORγ GAL4 Reporter Gene Assay

Example inhibitors 1-114 were tested for their ability to inhibit RORγ activity in a RORγ GAL4 reporter gene assay. The assay procedure and results are described below.

RORγ GAL4 Reporter Gene Assay Description

A GAL4 one-hybrid reporter system employing luciferase readout was established to determine inhibition of RORγ in 293FT cells. The RORγ ligand-binding domain (LBD) was fused to the yeast GAL4 DNA binding domain (DBD) and placed under the control of the human cytomegalovirus (CMV) immediate early promoter, using expression vector pFN26A (Promega) and standard recombinant DNA cloning methods. To serve as a control in the assay, a similar vector was generated in which the GAL4-DBD was fused to Herpes simplex virus protein 16 (VP16), a constitutive transcriptional activator.

To monitor the inhibitory effect of compounds on RORγ, a transcriptional reporter construct was used. The pGL4.35 vector (Promega) contains nine copies of the GAL4 Upstream Activator Sequence (UAS). This sequence drives the transcription of the luciferase reporter gene luc2P in response to binding of a fusion protein containing the GAL4 DNA binding domain, as for example expressed by the GAL4-RORγ-LBD and GAL4-VP16 expression vectors described above. To allow a GAL4 fusion protein to drive the expression of the luciferase reporter, the pGL4.35 expression vector and the appropriate GAL4 fusion protein expression vector were bulk transfected in the 293FT cells using standard transfection techniques.

The day after transfection, cells were plated into 96 well plates, test compound was added and the plates were incubated overnight. Subsequently, the firefly luciferase activity was quantified using luciferase detection reagent and luminescence readout.

Detailed Assay Description

293FT cells (Invitrogen) were transfected with a GAL4 fusion protein expression vector (as described above) and the transcriptional reporter construct (pGL4.35, Promega). 60 µL of TransIT-293 transfection reagent (Mirus Bio) was added drop wise to 1500 µl Opti-MEM I Reduced Serum Medium (Invitrogen) and incubated at room temperature (RT) for 5 to 20 minutes. 1500 µL of this reagent mixture was added to 5 µg of GAL4 fusion protein expression vector and 5 µg of the transcriptional reporter construct, and incubated at RT for 20 minutes.

To harvest 293FT cells from a T75 flask, first the culture medium was taken off the cells. Subsequently, the cells were washed with Phosphate Buffered Saline (PBS) (Lonza), after which the PBS was removed. To dissociate the cells, 1 ml of TrypLE Express (Invitrogen) was added to the flask, followed by incubation at RT until the cells visually started to detach. Cells were collected in 5 mL of assay medium (DMEM culture medium (Lonza), 10% dialyzed FBS (Invitrogen) and Pen/Strep (Lonza)) to achieve a single cell suspension. $10 \times 10^6$ cells were spun down and re-suspended in 10 mL of assay medium. Subsequently, the cell suspension was added to the transfection mix tube, and then transferred as a whole to a T75 flask (Greiner), followed by overnight (16-24 hours) incubation at 37° C. and 5% $CO_2$.

For compound screening, the cells were harvested (as described above) and counted. $13 \times 10^6$ cells were spun down, the supernatant was aspirated and the cells were re-suspended in 17.3 mL of assay medium to obtain a cell suspension of $0.75 \times 10^6$ cells/mL. 80 µL of cell suspension (60,000 cells) was plated per well into a white, flat bottom, tissue culture treated, 96 well screening plates (Greiner).

Test compounds were diluted, starting from a 10 mM dimethylsulfoxide (DMSO) stock solution, to serial dilutions in DMSO at 500× the final test concentration. Subsequently, these solutions were diluted to 5× the final test concentration in two 10-fold-dilution steps in assay medium. The final DMSO concentration of the 5× test compound solution was 1%. 20 µL of the 5× test compound solution was added to each test well of the 96 well plate previously plated with 80 µl cell suspension, resulting in the final test concentration with 0.2% DMSO.

The plates were incubated overnight (16-24 hours) at 37° C. and 5% $CO_2$.

For the luciferase readout, the luciferase reagent (Britelite Plus, Perkin Elmer) was brought to RT. To each test well of the screening plates, 100 µL of 2.5-fold diluted Britelite Plus reagent was added, followed by incubation at RT for 10 minutes. The luciferase luminescence signal was measured using a Wallac Victor Microplate Reader (Perkin Elmer).

The half maximum inhibitory concentration ($IC_{50}$) values for the test compounds were calculated from the luciferase signal using GraphPad Prism software (GraphPad Software).

All exemplified compounds of Formula I (Examples 1-114) were found to have mean $pIC_{50}$ values above 5.

Examples 2, 4, 5, 6, 9, 10, 12, 15, 19, 21, 22, 23, 26, 28, 29, 31-38, 40, 42-76, 78 -80, 82-90, 93-99, 102, 104, 106-110, and 112-114 were found to have mean $pIC_{50}$ values above or equal to 6.

Examples 2, 9, 29, 32, 33, 35, 37, 43, 44, 45, 46, 49, 51, 52, 53, 54, 55, 59, 60, 61, 62, 64, 66, 67, 68, 69, 71, 75, 76, 82, 83, 87, 88, 93, 94, 96, 98, 104, 106 107, 108, 109, 113, 114 were found to have mean pIC50 values above or equal to 7.

Examples 37, 44, 45, 46, 60, 64, 75, 82, 83 were found to have mean pIC50 values above or equal to 8.

Example 116

Peripheral Blood Mononuclear Cell (PBMC) IL-17 Assay

Example inhibitors 2, 9, 32, 33, 35, 37, 43, 44, 45, 46, 51, 53, 54, 59, 60, 67, 71, 83, 107, 113, 114 were tested for their ability to inhibit the IL-17A production in anti-CD3/anti-CD28 stimulated peripheral blood mononuclear cells (PBMCs) isolated from human blood. The assay procedure and results are described below.

PBMC IL-17 Assay Description

This assay is designed to measure the levels of IL-17A secreted from anti-CD3/anti-CD28 stimulated PBMCs with the aim of measuring RORγ mediated inhibition of IL-17A production.

The assay medium consists of 90% RPMI 1640 (Lonza), 10% heat inactivated fetal bovin serum (FBS, Lonza) and 100 U/mL penicillin/streptomycin solution.

Assay Description

Anti-CD3 antibody (BD Pharmingen) was diluted to 10 µg/ml in PBS (Lonza). 30 µL of 10 µg/ml anti-CD3 solution was added to the inner 60 wells, excluding any negative control wells, of a 96-well cell culture treated U-bottom plate (Greiner). Plates were incubated overnight (16-24 hours) at 37° C. and 5% $CO_2$.

Peripheral blood mononuclear cells were separated from buffy coats (Sanquin) using Ficoll-Paque PREMIUM separation medium (GE Healthcare Life Sciences) according to manufacturer's protocol and re-suspended in assay medium at 37° C.

Test compounds were diluted, starting from a 10 mM dimethylsulfoxide (DMSO) stock solution, to serial dilutions in DMSO at 200× the final test concentration. Subsequently, these solutions were diluted in two dilution steps in assay medium to 10× the final test concentration. The DMSO concentration of the 10× test compound solution was 5%.

Anti-CD28 antibody (BD Pharmingen) was diluted to 20 µg/mL in PBS. The PBMCs were diluted to a concentration of $2.5 \times 10^6$ cells/mL in assay medium at 37° C.

For compound screening, the anti-CD3 coated plates were washed three times with PBS, the wells were subsequently aspirated using vacuum. To each screening well 80 μL of the PBMC suspension, 10 μL of the anti-CD28 solution and 10 μL of the 10× test compound solution was added, resulting in the final test concentration with 0.5% DMSO. All outer wells were filled with assay medium to prevent evaporation. Plates were incubated for 5 days at 37° C. and 5% $CO_2$.

After incubation the plates were spun down at 1500 rpm for 4 minutes and the supernatant was collected. Subsequently, the IL-17A levels in the supernatants was determined using an IL-17 ELISA kit (human IL-17 DuoSet, R&D systems) according to manufacturer's protocol.

The half maximum inhibitory concentration ($IC_{50}$) values for the test compounds were calculated from the IL-17A signal using GraphPad Prism software (GraphPad Software).

The tested examples 2, 9, 32, 33, 35, 37, 43, 44, 45, 46, 51, 53, 54, 59, 60, 67, 71, 83, 107, 113, 114 were all found to have mean $pIC_{50}$ values above or equal to 6.

Examples 9, 32, 37, 43, 44, 45, 46, 51, 53, 54, 59, 60, 67, 71, 83, 113, 114 were found to have mean $pIC_{50}$ values above or equal to 7.

The invention claimed is:

1. A compound according to Formula I

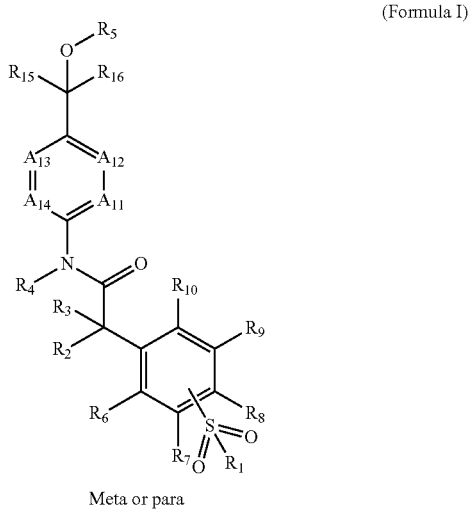

(Formula I)

Meta or para or a pharmaceutically acceptable salt thereof wherein
$A_{11}$-$A_{14}$ are N or $CR_{11}$, $CR_{12}$, $CR_{13}$, $CR_{14}$, respectively, with the proviso that no more than two of the four positions A can be simultaneously N;
$R_1$ is C(1-6)alkyl, C(3-6)cycloalkyl, C(3-6)cycloalkylC(1-3)alkyl, (di)C(1-6)alkylamino, (di)C(3-6)cycloalkylamino or (di)(C(3-6)cycloalkylC(1-3)alkyl)amino, with all carbon atoms of alkyl groups optionally substituted with one or more F and all carbon atoms of cycloalkyl groups optionally substituted with one or more F or methyl;
$R_2$ and $R_3$ are independently H, F, methyl, ethyl, hydroxy, methoxy or $R_2$ and $R_3$ together is carbonyl, all alkyl groups, if present, optionally being substituted with one or more F;
$R_4$ is H or C(1-6)alkyl;
$R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, C(3-6)cycloalkylC(1-3)alkyl, C(2-5)heterocycloalkyl or C(2-5)heterocycloalkylC(1-3)alkyl, all groups optionally substituted with one or more F, Cl, C(1-2)alkyl, C(1-2)alkoxy or cyano;
the sulfonyl group with $R_1$ is represented by one of $R_7$, $R_8$ or $R_9$;
the remaining $R_6$-$R_{14}$ are independently H, halogen, C(1-3)alkoxy, (di)C(1-3)alkylamino or C(1-6)alkyl, all of the alkyl groups optionally being substituted with one or more F; and
$R_{15}$ and $R_{16}$ are independently H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkylC(1-3)alkyl, all groups optionally substituted with one or more F, Cl, C(1-2)alkyl, C(1-2) alkoxy or cyano.

2. The compound according to claim 1 wherein $R_1$ is C(1-2)alkyl, cyclopropyl, C(3-4)cycloalkylC(1-3)alkyl, methylamino or C(3-4)cycloalkylamino.

3. The compound according to claim 2 wherein $R_1$ is ethyl, cyclopropylamino or cyclopropylmethyl.

4. The compound according to claim 3 wherein $R_1$ is cyclopropylamino or cyclopropylmethyl.

5. The compound according to claim 4 wherein $R_1$ is cyclopropylmethyl.

6. The compound according to claim 1 wherein $R_2$ and $R_3$ are independently H, methyl or hydroxy.

7. The compound according to claim 6 wherein $R_2$ and $R_3$ are independently H or methyl.

8. The compound according to claim 1 wherein $R_4$ is H or C(1-2)alkyl.

9. The compound according to claim 1 where $R_5$ is H, hydroxyethyl, methoxyethyl or C(1-6)alkyl, all alkyl groups optionally being substituted with one or more F.

10. The compound according to claim 9 wherein $R_5$ is H or C(1-3)alkyl.

11. The compound according to claim 1 wherein $R_5$ is C(6)arylC(1-3)alkyl or C(3-6)cycloalkylC(1-3)alkyl.

12. The compound according to claim 11 wherein $R_5$ is benzyl.

13. The compound according to claim 1 wherein $R_6$-$R_{10}$ are H with the proviso that one of the groups $R_7$, $R_8$ or $R_9$ is the sulfonyl group with $R_1$.

14. The compound according to claim 13 wherein $R_8$ is the sulfonyl group with $R_1$.

15. The compound according to claim 1 wherein $R_8$ is the sulfonyl group with $R_1$, and wherein $R_{10}$ is methyl, and the remaining $R_6$, $R_7$ and $R_9$ are H.

16. The compound according to claim 1 wherein all of $A_{11}$-$A_{14}$ are carbon.

17. The compound according to claim 1 wherein either $A_{11}$ or $A_{12}$ is nitrogen and the remaining $A_{11}$-$A_{14}$ are carbon.

18. The compound according to claim 1 wherein $R_{11}$-$R_{14}$ are independently H, halogen, methyl or methoxy.

19. The compound according to claim 18 wherein $R_{11}$-$R_{14}$ is H.

20. The compound according to claim 1 wherein $R_{15}$ is $CF_3$ and $R_{16}$ is H, C(1-6)alkyl, C(3-6)cycloalkyl or C(3-6)cycloalkylC(1-3)alkyl.

21. The compound according to claim 20 wherein $R_{15}$ is $CF_3$ and $R_{16}$ is $CF_3$, propyl, isopropyl, 2-methylpropyl, 2,2-dimethylpropyl, cyclopropyl, cyclopentyl or cyclohexylmethyl.

22. The compound according to claim 21 wherein both $R_{15}$ and $R_{16}$ are $CF_3$.

23. The compound selected from claim 1 which is selected from the group of:

N-(4-(1,1,1,3,3,3-hexafluoro-2-hydroxypropan-2-yl)phenyl)-2-(4-(methylsulfonyl)phenyl)acetamide;

2-(4-(ethylsulfonyl)phenyl)-N-(4-(1,1,1,3,3,3-hexafluoro-2-hydroxypropan-2-yl)phenyl)acetamide;

N-(4-(1,1,1,3,3,3-hexafluoro-2-hydroxypropan-2-yl)phenyl)-2-(4-(isopropylsulfonyl)phenyl)acetamide;

N-(4-(1,1,1,3,3,3-hexafluoro-2-hydroxypropan-2-yl)phenyl)-2-(4-(propylsulfonyl)phenyl)acetamide;

2-(4-(ethylsulfonyl)phenyl)-N-(4-(1,1,1,3,3,3-hexafluoro-2-hydroxypropan-2-yl)phenyl)propanamide;

N-(4-(1,1,1,3,3,3-hexafluoro-2-hydroxypropan-2-yl)phenyl)-2-(4-(N-methylsulfamoyl)phenyl)acetamide;

N-(4-(1,1,1,3,3,3-hexafluoro-2-hydroxypropan-2-yl)phenyl)-2-(4-(N-isopropylsulfamoyl)phenyl)acetamide;

2-(4-(N-(cyclopropylmethyl)sulfamoyl)phenyl)-N-(4-(1,1,1,3,3,3-hexafluoro-2-hydroxypropan-2-yl)phenyl)acetamide;

2-(4-(N-cyclopropylsulfamoyl)phenyl)-N-(4-(1,1,1,3,3,3-hexafluoro-2-hydroxypropan-2-yl)phenyl)acetamide;

2-(4-(N-ethylsulfamoyl)phenyl)-N-(4-(1,1,1,3,3,3-hexafluoro-2-hydroxypropan-2-yl)phenyl)acetamide;

2-(4-(N,N-dimethylsulfamoyl)phenyl)-N-(4-(1,1,1,3,3,3-hexafluoro-2-hydroxypropan-2-yl)phenyl)acetamide;

2-(3-(N-cyclopropylsulfamoyl)phenyl)-N-(4-(1,1,1,3,3,3-hexafluoro-2-hydroxypropan-2-yl)phenyl)acetamide;

2-(3-(N-ethylsulfamoyl)phenyl)-N-(4-(1,1,1,3,3,3-hexafluoro-2-hydroxypropan-2-yl)phenyl)acetamide;

2-(3-(N,N-dimethylsulfamoyl)phenyl)-N-(4-(1,1,1,3,3,3-hexafluoro-2-hydroxypropan-2-yl)phenyl)acetamide;

2-(4-(ethylsulfonyl)phenyl)-N-(3-fluoro-4-(1,1,1,3,3,3-hexafluoro-2-hydroxypropan-2-yl)-2-methylphenyl)acetamide;

2-(4-(N-cyclopropylsulfamoyl)phenyl)-N-(4-(1,1,1,3,3,3-hexafluoro-2-hydroxypropan-2-yl)phenyl)-N-methylacetamide;

2-(4-(N-cyclopropylsulfamoyl)phenyl)-N-ethyl-N-(4-(1,1,1,3,3,3-hexafluoro-2-hydroxypropan-2-yl)phenyl)acetamide;

2-(3-(N-cyclopropylsulfamoyl)phenyl)-N-(4-(1,1,1,3,3,3-hexafluoro-2-hydroxypropan-2-yl)phenyl)-N-methylacetamide;

N-(4-(1,1,1,3,3,3-hexafluoro-2-hydroxypropan-2-yl)phenyl)-2-(3-(N-methylsulfamoyl)phenyl)acetamide;

2-(4-(ethylsulfonyl)phenyl)-N-(5-fluoro-4-(1,1,1,3,3,3-hexafluoro-2-hydroxypropan-2-yl)-2-methoxyphenyl)acetamide;

2-(4-(ethylsulfonyl)phenyl)-N-(5-(1,1,1,3,3,3-hexafluoro-2-hydroxypropan-2-yl)pyridin-2-yl)acetamide;

N-(5-chloro-4-(1,1,1,3,3,3-hexafluoro-2-hydroxypropan-2-yl)-2-methoxyphenyl)-2-(4-(ethylsulfonyl)phenyl)acetamide;

2-(4-(ethylsulfonyl)phenyl)-N-(4-(1,1,1,3,3,3-hexafluoro-2-hydroxypropan-2-yl)-2,6-dimethylphenyl)acetamide;

2-(3-(N-cyclobutylsulfamoyl)phenyl)-N-(4-(1,1,1,3,3,3-hexafluoro-2-hydroxypropan-2-yl)phenyl)acetamide;

2-(4-(N-cyclobutylsulfamoyl)phenyl)-N-(4-(1,1,1,3,3,3-hexafluoro-2-hydroxypropan-2-yl)phenyl)acetamide;

2-(4-(N-cyclopropylsulfamoyl)phenyl)-N-(3-fluoro-4-(1,1,1,3,3,3-hexafluoro-2-hydroxypropan-2-yl)-2-methylphenyl)acetamide;

N-(4-(1,1,1,3,3,3-hexafluoro-2-hydroxypropan-2-yl)phenyl)-2-(4-(isobutylsulfonyl)phenyl)acetamide;

2-(4-(ethylsulfonyl)phenyl)-N-(2-fluoro-4-(1,1,1,3,3,3-hexafluoro-2-hydroxypropan-2-yl)phenyl)acetamide;

2-(4-(ethylsulfonyl)phenyl)-N-(4-(1,1,1,3,3,3-hexafluoro-2-hydroxypropan-2-yl)-3-methylphenyl)acetamide;

2-(4-(ethylsulfonyl)phenyl)-N-(3-fluoro-4-(1,1,1,3,3,3-hexafluoro-2-hydroxypropan-2-yl)phenyl)acetamide;

2-(4-(ethylsulfonyl)phenyl)-N-(4-(1,1,1,3,3,3-hexafluoro-2-hydroxypropan-2-yl)-2-methylphenyl)acetamide;

2-(4-(N-cyclopropylsulfamoyl)phenyl)-N-(4-(1,1,1,3,3,3-hexafluoro-2-hydroxypropan-2-yl)-3-methylphenyl)acetamide;

2-(4-(N-cyclopropylsulfamoyl)phenyl)-N-(3-fluoro-4-(1,1,1,3,3,3-hexafluoro-2-hydroxypropan-2-yl)phenyl)acetamide;

2-(4-(N-cyclopropylsulfamoyl)phenyl)-N-(4-(1,1,1,3,3,3-hexafluoro-2-hydroxypropan-2-yl)-2-methylphenyl)acetamide;

2-(4-(N-cyclopropylsulfamoyl)phenyl)-N-(2-fluoro-4-(1,1,1,3,3,3-hexafluoro-2-hydroxypropan-2-yl)phenyl)acetamide;

2-(3-(N-cyclopropylsulfamoyl)phenyl)-N-(4-(1,1,1,3,3,3-hexafluoro-2-hydroxypropan-2-yl)-3-methylphenyl)acetamide;

2-(4-((cyclopropylmethyl)sulfonyl)phenyl)-N-(4-(1,1,1,3,3,3-hexafluoro-2-hydroxypropan-2-yl)phenyl)acetamide;

2-(3-(N-cyclopropylsulfamoyl)phenyl)-N-(3-fluoro-4-(1,1,1,3,3,3-hexafluoro-2-hydroxypropan-2-yl)phenyl)acetamide;

2-(3-(N-cyclopropylsulfamoyl)phenyl)-N-(4-(1,1,1,3,3,3-hexafluoro-2-hydroxypropan-2-yl)-2-methylphenyl)acetamide;

2-(3-(N-cyclopropylsulfamoyl)phenyl)-N-(2-fluoro-4-(1,1,1,3,3,3-hexafluoro-2-hydroxypropan-2-yl)phenyl)acetamide;

2-(3-(N-(cyclopropylmethyl)sulfamoyl)phenyl)-N-(4-(1,1,1,3,3,3-hexafluoro-2-hydroxypropan-2-yl)phenyl)acetamide;

2-(4-(ethylsulfonyl)-3-fluorophenyl)-N-(4-(1,1,1,3,3,3-hexafluoro-2-hydroxypropan-2-yl)phenyl)acetamide;

2-(4-((cyclopropylmethyl)sulfonyl)phenyl)-N-(4-(1,1,1,3,3,3-hexafluoro-2-hydroxypropan-2-yl)-2-methylphenyl)acetamide;

2-(4-((cyclopropylmethyl)sulfonyl)phenyl)-N-(4-(1,1,1,3,3,3-hexafluoro-2-hydroxypropan-2-yl)-3-methylphenyl)acetamide;

2-(4-((cyclopropylmethyl)sulfonyl)phenyl)-N-(3-fluoro-4-(1,1,1,3,3,3-hexafluoro-2-hydroxypropan-2-yl)phenyl)acetamide;

2-(4-((cyclopropylmethyl)sulfonyl)phenyl)-N-(2-fluoro-4-(1,1,1,3,3,3-hexafluoro-2-hydroxypropan-2-yl)phenyl)acetamide;

2-(4-(ethylsulfonyl)phenyl)-N-(4-(1,1,1,3,3,3-hexafluoro-2-methoxypropan-2-yl)phenyl)acetamide;

N-(4-(2-ethoxy-1,1,1,3,3,3-hexafluoropropan-2-yl)phenyl)-2-(4-(ethylsulfonyl)phenyl)acetamide;

2-(4-(ethylsulfonyl)phenyl)-N-(4-(1,1,1,3,3,3-hexafluoro-2-propoxypropan-2-yl)phenyl)acetamide;

N-(4-(2-(benzyloxy)-1,1,1,3,3,3-hexafluoropropan-2-yl)phenyl)-2-(4-(ethylsulfonyl)phenyl)acetamide;

2-(4-((cyclopropylmethyl)sulfonyl)phenyl)-N-(4-(1,1,1,3,3,3-hexafluoro-2-isopropoxypropan-2-yl)phenyl)acetamide;

N-(4-(2-butoxy-1,1,1,3,3,3-hexafluoropropan-2-yl)phenyl)-2-(4-((cyclopropylmethyl)sulfonyl)phenyl)acetamide;

2-(4-((cyclopropylmethyl)sulfonyl)phenyl)-N-(4-(2-ethoxy-1,1,1,3,3,3-hexafluoropropan-2-yl)phenyl)acetamide;

2-(4-((cyclopropylmethyl)sulfonyl)phenyl)-N-(4-(1,1,1,3,3,3-hexafluoro-2-methoxypropan-2-yl)phenyl)acetamide;

2-(4-((cyclopropylmethyl)sulfonyl)phenyl)-N-(4-(1,1,1,3,3,3-hexafluoro-2-hydroxypropan-2-yl)-2-methoxyphenyl)acetamide;

2-(4-((cyclopropylmethyl)sulfonyl)phenyl)-N-(4-(1,1,1,3,3,3-hexafluoro-2-hydroxypropan-2-yl)-3-methoxyphenyl)acetamide;

N-(2-amino-4-(1,1,1,3,3,3-hexafluoro-2-hydroxypropan-2-yl)phenyl)-2-(4-((cyclopropylmethyl)sulfonyl)phenyl)acetamide;

N-(4-(2-(2-cyclopropylethoxy)-1,1,1,3,3,3-hexafluoropropan-2-yl)phenyl)-2-(4-((cyclopropylmethyl)sulfonyl)phenyl)acetamide;

N-(4-(2-(benzyloxy)-1,1,1,3,3,3-hexafluoropropan-2-yl)phenyl)-2-(4-((cyclopropylmethyl)sulfonyl)phenyl)acetamide;

2-(4-((cyclopropylmethyl)sulfonyl)phenyl)-N-(4-(1,1,1,3,3,3-hexafluoro-2-propoxypropan-2-yl)phenyl)acetamide;

2-(4-(N-cyclopropylsulfamoyl)phenyl)-N-(4-(1,1,1,3,3,3-hexafluoro-2-propoxypropan-2-yl)phenyl)acetamide;

N-(3-chloro-4-(1,1,1,3,3,3-hexafluoro-2-hydroxypropan-2-yl)phenyl)-2-(4-((cyclopropylmethyl)sulfonyl)phenyl)acetamide;

2-(4-(ethylsulfonyl)phenyl)-N-(4-(1,1,1-trifluoro-2-hydroxypentan-2-yl)phenyl)acetamide;

2-(4-((cyclopropylmethyl)sulfonyl)phenyl)-N-(4-(1,1,1-trifluoro-2-hydroxyhexan-2-yl)phenyl)acetamide;

2-(4-(ethylsulfonyl)phenyl)-N-(4-(1,1,1-trifluoro-2-hydroxy-3-methylbutan-2-yl)phenyl)acetamide;

2-(4-(ethylsulfonyl)phenyl)-N-(4-(1,1,1-trifluoro-2-hydroxy-4-methylpentan-2-yl)phenyl)acetamide;

N-(4-(1-cyclopropyl-2,2,2-trifluoro-1-hydroxyethyl)phenyl)-2-(4-((cyclopropylmethyl)sulfonyl)phenyl)acetamide;

N-(4-(3-cyclopentyl-1,1,1-trifluoro-2-hydroxypropan-2-yl)phenyl)-2-(4-((cyclopropylmethyl)sulfonyl)phenyl)acetamide;

N-(4-(3-cyclohexyl-1,1,1-trifluoro-2-hydroxypropan-2-yl)phenyl)-2-(4-((cyclopropylmethyl)sulfonyl)phenyl)acetamide;

2-(4-((cyclopropylmethyl)sulfonyl)phenyl)-N-(4-(2,2,2-trifluoro-1-hydroxyethyl)phenyl)acetamide;

2-(4-((cyclopropylmethyl)sulfonyl)phenyl)-N-(4-(1,1,1-trifluoro-2-hydroxypropan-2-yl)phenyl)acetamide;

2-(4-(ethylsulfonyl)phenyl)-N-(4-(1,1,1-trifluoro-2-hydroxyhexan-2-yl)phenyl)acetamide;

N-(4-(1-cyclopropyl-2,2,2-trifluoro-1-hydroxyethyl)phenyl)-2-(4-(ethylsulfonyl)phenyl)acetamide;

N-(4-(3-cyclohexyl-1,1,1-trifluoro-2-hydroxypropan-2-yl)phenyl)-2-(4-(ethylsulfonyl)phenyl)acetamide;

N-(4-(1-cyclopentyl-2,2,2-trifluoro-1-hydroxyethyl)phenyl)-2-(4-((cyclopropylmethyl)sulfonyl)phenyl)acetamide;

2-(4-(N-cyclopropylsulfamoyl)phenyl)-N-(4-(1,1,1-trifluoro-2-hydroxy-4-methylpentan-2-yl)phenyl)acetamide;

2-(3-(N-cyclopropylsulfamoyl)phenyl)-N-(4-(1,1,1-trifluoro-2-hydroxy-4-methylpentan-2-yl)phenyl)acetamide;

2-(4-(N-cyclopropylsulfamoyl)phenyl)-N-(4-(1,1,1-trifluoro-2-hydroxypropan-2-yl)phenyl)acetamide;

2-(4-(N-cyclopropylsulfamoyl)phenyl)-N-(4-(1,1,1-trifluoro-2-hydroxybutan-2-yl)phenyl)acetamide;

2-(4-(N-cyclopropylsulfamoyl)phenyl)-N-(4-(1,1,1-trifluoro-2-hydroxypentan-2-yl)phenyl)acetamide;

2-(3-(N-cyclopropylsulfamoyl)phenyl)-N-(4-(1,1,1-trifluoro-2-hydroxypentan-2-yl)phenyl)acetamide;

2-(4-((cyclopropylmethyl)sulfonyl)phenyl)-N-(4-(1,1,1-trifluoro-2-hydroxy-4,4-dimethylpentan-2-yl)phenyl)acetamide;

2-(4-((cyclopropylmethyl)sulfonyl)phenyl)-N-(4-(1,1,1-trifluoro-2-hydroxybutan-2-yl)phenyl)acetamide;

N-(3-chloro-4-(1,1,1,3,3,3-hexafluoro-2-hydroxypropan-2-yl)phenyl)-2-(4-(ethylsulfonyl)phenyl)acetamide;

N-(4-(1-cyclopentyl-2,2,2-trifluoro-1-hydroxyethyl)phenyl)-2-(4-(ethylsulfonyl)phenyl)acetamide;

N-(4-(3-cyclopentyl-1,1,1-trifluoro-2-hydroxypropan-2-yl)phenyl)-2-(4-(ethylsulfonyl)phenyl)acetamide;

2-(4-cyclopropylmethanesulfonylphenyl)-N-[4-(1,1,1-trifluoro-2-hydroxy-3-phenylpropan-2-yl)phenyl]acetamide;

2-(4-((cyclopropylmethyl)sulfonyl)phenyl)-N-(4-(2,2,2-trifluoro-1-hydroxy-1-phenylethyl)phenyl)acetamide;

N-(3-chloro-4-(1,1,1,3,3,3-hexafluoro-2-hydroxypropan-2-yl)phenyl)-2-(4-(N-cyclopropylsulfamoyl)phenyl)acetamide;

N-(4-(1-cyclopentyl-2,2,2-trifluoro-1-hydroxyethyl)phenyl)-2-(4-(N-cyclopropylsulfamoyl)phenyl)acetamide;

N-(3-chloro-4-(1,1,1,3,3,3-hexafluoro-2-hydroxypropan-2-yl)phenyl)-2-(3-(N-cyclopropylsulfamoyl)phenyl)acetamide;

N-(4-(1-cyclopentyl-2,2,2-trifluoro-1-hydroxyethyl)phenyl)-2-(3-(N-cyclopropylsulfamoyl)phenyl)acetamide;

2-(4-((cyclopropylmethyl)sulfonyl)-2-methylphenyl)-N-(4-(1,1,1,3,3,3-hexafluoro-2-hydroxypropan-2-yl)phenyl)acetamide;

2-(4-(N-cyclopropylsulfamoyl)phenyl)-N-(4-(1,1,1-trifluoro-2-hydroxy-4,4-dimethylpentan-2-yl)phenyl)acetamide;

2-(4-(N-cyclopropylsulfamoyl)phenyl)-N-(4-(1,1,1-trifluoro-2-hydroxy-3-methylbutan-2-yl)phenyl)acetamide;

2-(4-(ethylsulfonyl)phenyl)-N-(4-(1,1,1-trifluoro-2-hydroxy-4,4-dimethylpentan-2-yl)phenyl)acetamide;

2-(4-(ethylsulfonyl)phenyl)-N-(4-(2,2,2-trifluoro-1-hydroxy-1-phenylethyl)phenyl)acetamide;

N-(2-chloro-4-(1,1,1,3,3,3-hexafluoro-2-hydroxypropan-2-yl)phenyl)-2-(4-((cyclopropylmethyl)sulfonyl)phenyl)acetamide;

N-(4-(3-cyclopentyl-1,1,1-trifluoro-2-hydroxypropan-2-yl)phenyl)-2-(4-(N-cyclopropylsulfamoyl)phenyl)acetamide;

N-(4-(3-cyclohexyl-1,1,1-trifluoro-2-hydroxypropan-2-yl)phenyl)-2-(4-(N-cyclopropylsulfamoyl)phenyl)acetamide;

2-(4-(N-cyclopropylsulfamoyl)phenyl)-N-(4-(2,2,2-trifluoro-1-hydroxy-1-phenylethyl)phenyl)acetamide;

2-(4-((cyclopropylmethyl)sulfonyl)phenyl)-N-(4-(1,1,1,3,3,3-hexafluoro-2-hydroxypropan-2-yl)phenyl)-2-oxoacetamide;

2-(4-((cyclopropylmethyl)sulfonyl)phenyl)-N-(4-(2-hydroxypropan-2-yl)phenyl)acetamide;

2-(4-((cyclopropylmethyl)sulfonyl)phenyl)-N-(4-(1,1,1-trifluoro-2-hydroxy-5-methylhexan-2-yl)phenyl)acetamide;

2-(4-(N-cyclopropylsulfamoyl)phenyl)-N-(5-fluoro-4-(1,1,3,3,3-hexafluoro-2-hydroxypropan-2-yl)-2-methoxyphenyl)acetamide;

2-(4-((cyclopropylmethyl)sulfonyl)phenyl)-N-(4-(dicyclopropyl(hydroxy)methyl)phenyl)acetamide;

2-(4-((cyclopropylmethyl)sulfonyl)phenyl)-N-(5-(1,1,1,3,3,3-hexafluoro-2-hydroxypropan-2-yl)pyridin-2-yl)acetamide;

2-(4-((cyclopropylmethyl)sulfonyl)phenyl)-N-(4-(1,1,1-trifluoro-2-hydroxy-6-methylheptan-2-yl)phenyl)acetamide;

2-(4-((cyclopropylmethyl)sulfonyl)phenyl)-N-(4-(1,1,1,3,3,3-hexafluoro-2-hydroxypropan-2-yl)phenyl)propanamide;

2-(4-((cyclopropylmethyl)sulfonyl)phenyl)-N-(6-(1,1,1,3,3,3-hexafluoro-2-hydroxypropan-2-yl)pyridin-3-yl)acetamide;

2-(4-(ethylsulfonyl)phenyl)-N-(6-(1,1,1,3,3,3-hexafluoro-2-hydroxypropan-2-yl) pyridin-3-yl)acetamide;

2-(4-(ethylsulfonyl)phenyl)-N-(4-(1,1,1,3,3,3-hexafluoro-2-(2,2,2-trifluoroethoxy)propan-2-yl)phenyl)acetamide;

2-(4-((cyclopropylmethyl)sulfonyl)phenyl)-N-(4-(1,1,1,3,3,3-hexafluoro-2-(2,2,2-trifluoroethoxy)propan-2-yl)phenyl)acetamide and 2-(4-((cyclopropylmethyl)sulfonyl)phenyl)-N-(4-(1,1,1,3,3,3-hexafluoro-2-hydroxypropan-2-yl)phenyl)-2-hydroxyacetamide.

24. The compound according to claim 23 which is 2-(4-((cyclopropylmethyl)sulfonyl)phenyl)-N-(4-(1,1,1,3,3,3-hexafluoro-2-hydroxy propan-2-yl)phenyl)acetamide.

25. A pharmaceutical composition which comprises a compound of Formula I according to claim 1 or a pharmaceutically acceptable salt thereof and one or more pharmaceutically acceptable excipients.

26. A pharmaceutical composition according to claim 25, which further comprises at least one additional therapeutically active agent.

* * * * *